US006284767B1

(12) United States Patent
Sham et al.

(10) Patent No.: US 6,284,767 B1
(45) Date of Patent: *Sep. 4, 2001

(54) RETROVIRAL PROTEASE INHIBITING COMPOUNDS

(75) Inventors: Hing Leung Sham, Vernon Hills; Daniel W. Norbeck, Grayslake; Dale J. Kempf, Libertyville, all of IL (US); Xiaoqi Chen, San Mateo, CA (US); David A. Betebenner, Lawrenceville, NJ (US); Thomas R. Herrin, Waukegan, IL (US); Gondi N. Kumar, Newbury Park, CA (US); John M. Lipari, Racine, WI (US); Laman Alani, Morris Plains, NJ (US); Soumojeet Ghosh, Lindenhurst, IL (US); Rong R. Gao, Edison; Dilip Kaul, Edison, both of NJ (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 64 days.

(21) Appl. No.: 09/207,873

(22) Filed: Dec. 8, 1998

Related U.S. Application Data

(60) Division of application No. 08/753,201, filed on Nov. 21, 1996, now Pat. No. 5,914,332, which is a continuation-in-part of application No. 08/572,226, filed on Dec. 13, 1995, now abandoned.

(51) Int. Cl.$^7$ .................. A61K 31/4166; A61K 31/506; A61K 31/535
(52) U.S. Cl. .................. 514/274; 514/211.03; 514/218; 514/220; 514/228.8; 514/237.5; 514/253.01; 514/256; 514/307; 514/311; 514/347; 514/365; 514/376; 514/377; 514/392
(58) Field of Search .................. 514/211, 218, 514/220, 228.8, 274, 376, 255, 392, 365, 237.5, 307, 311, 347, 211.03, 253.01, 377

(56) References Cited

U.S. PATENT DOCUMENTS

| | | | |
|---|---|---|---|
| 4,885,292 | 12/1989 | Ryono et al. | 514/211 |
| 5,142,056 | 8/1992 | Kempf et al. | 546/265 |
| 5,196,438 | 3/1993 | Martin et al. | 514/311 |
| 5,354,866 | 10/1994 | Kempf et al. | 546/265 |
| 5,413,999 | 5/1995 | Vaca et al. | 514/231.5 |
| 5,484,926 | 1/1996 | Dressman et al. | 546/114 |
| 5,541,206 | 7/1996 | Kempf et al. | 514/365 |
| 5,635,523 | 6/1997 | Kempf et al. | 514/365 |
| 5,643,878 | 7/1997 | Bold et al. | 514/19 |
| 5,648,497 | 7/1997 | Kempf et al. | 548/204 |
| 5,674,882 | 10/1997 | Kempf et al. | 514/365 |
| 5,750,648 | 5/1998 | Chang et al. | 530/331 |
| 5,846,987 | 12/1998 | Kempf et al. | 514/365 |
| 5,883,252 | * 3/1999 | Tung et al. | 544/71 |
| 5,886,036 | 3/1999 | Kempf et al. | 514/533 |
| 5,945,413 | * 8/1999 | Tung et al. | 514/193 |
| 6,017,928 | 1/2000 | Kempf et al. | 514/314 |
| 6,037,157 | 3/2000 | Norbeck et al. | 435/184 |

FOREIGN PATENT DOCUMENTS

| | | |
|---|---|---|
| 0005689 | 11/1979 | (EP) . |
| 0342541 | 11/1989 | (EP) . |
| 365992 | 5/1990 | (EP) . |
| 428849 | 5/1991 | (EP) . |
| 0490667 | 6/1992 | (EP) . |
| 0532466 | 3/1993 | (EP) . |
| 0560268 | 9/1993 | (EP) . |
| 0580402 | 1/1994 | (EP) . |
| 8910752 | 11/1989 | (WO) . |
| 9208701 | 5/1992 | (WO) . |
| 9307128 | 4/1993 | (WO) . |
| 9323368 | 11/1993 | (WO) . |
| 9405639 | 3/1994 | (WO) . |
| 9530670 | 11/1995 | (WO) . |

OTHER PUBLICATIONS

Tung et al., Chemical Abstracts, vol. 131, abstract 185247, 1999.*
Y. Becker, et al., J. Org. Chem. 45 2145–2151 (1980).
H. Takechi, et al., Chem. Pharm. Bull.34 (8) 3142–3152 (1986).
A. Smith, et al., J. Am. Chem. Soc. 117 11113–11123 (1995).
J. Vacca, et al., Bioorg. Med. Chem. Lett. 4 499–504 (1994).
R. Randad, et al., Bioorg. Med. Chem. Lett. 4 1247–1252 (1994).
Scholz, et al., J. Med. Chem. 37 3079–3089 (1994).
Jindrich, et al., Collect. Czech.Chem. Commun.58 (7) 1645–1667 (1993).

* cited by examiner

*Primary Examiner*—Richard L. Raymond
(74) *Attorney, Agent, or Firm*—Steven R. Crowley

(57) ABSTRACT

A compound of the formula:

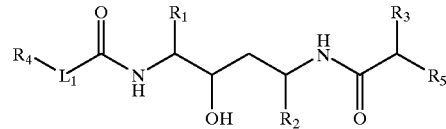

is disclosed as an HIV protease inhibitor. Methods and compositions for inhibiting an HIV infection are also disclosed.

98 Claims, No Drawings

RETROVIRAL PROTEASE INHIBITING COMPOUNDS

This is a division of U.S. patent application Ser. No. 08/753,201, filed Nov. 21, 1996, now U.S. Pat. No. 5,914, 332, which is a continuation-in-part of U.S. patent application Ser. No. 08/572,226, filed Dec. 13, 1995, now abandoned.

TECHNICAL FIELD

The present invention relates to novel compounds and a composition and method for inhibiting retroviral proteases and in particular for inhibiting human immunodeficiency virus (HIV) protease, a composition and method for inhibiting a retroviral infection and in particular an HIV infection, processes for making the compounds and synthetic intermediates employed in the processes.

BACKGROUND OF THE INVENTION

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, human T-cell lymphotrophic viruses 1, 11, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin 11. Inhibitors of renin and ACE are known to reduce high blood pressure in v. An inhibitor of a retroviral protease will provide a therapeutic agent for diseases caused by the retrovirus.

The genomes of retroviruses encode a protease that is responsible for the proteolytic processing of one or more polyprotein precursors such as the and a gene products. See Wellink, Arch. Virol. 98 1 (1988). Retroviral proteases most commonly process the gag precursor into core proteins, and also process the poi precursor into reverse transcriptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido-3'-deoxythymidine (AZT), 2',3'-dideoxycytidine (DDC), 2',3'-dideoxyinosine (DDI), d4T and 3TC and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

Recently the HIV protease inhibitors ritonavir, saquinavir and indinavir have been approved in the U.S. for treatment of HIV infections. However, there is a continuing need for improved HIV protease inhibitors.

DISCLOSURE OF THE INVENTION

In accordance with the present invention, there is a compound of the formula I:

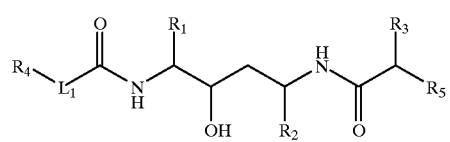

wherein $R_1$ and $R_2$ are independently selected from the group consisting of loweralkyl, cycloalkylalkyl and arylalkyl;

$R_3$ is loweralkyl, hydroxyalkyl or cycloalkylalkyl;

$R_4$ is aryl or heterocyclic;

$R_5$ is a)

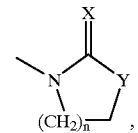

b)

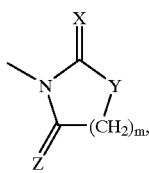

c)

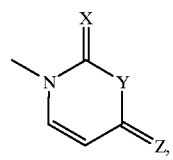

d)

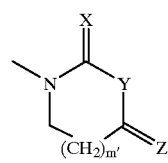

-continued e)
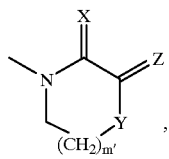

f)
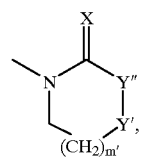

g)
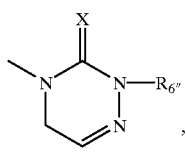

h)
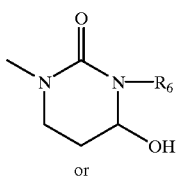

i)
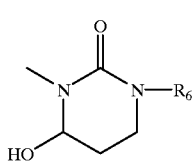

wherein n is 1, 2 or 3, m is 1, 2 or 3, m' is 1 or 2, X is O, S or NH, Y is —CH$_2$—, —O—, —S— or —N(R$_6$)— wherein R$_6$ is hydrogen, loweralkyl, cycloalkyl, cycloalkylalkyl, aryl or arylalkyl, Y" is —CH$_2$— or —N(R$_{6''}$)— wherein R$_{6''}$ is hydrogen, loweralkyl, cycloalkyl, cycloalkylalkyl, aryl or arylalkyl, Y' is —N(R$_{6'}$)— wherein R$_{6'}$ is hydrogen, loweralkyl, cycloalkyl, cycloalkylalkyl, aryl or arylalkyl, and Z is O, S or NH; and L$_1$ is
  a) —O—,
  b) —S—,
  c) —N(R$_7$)— wherein R$_7$ is hydrogen, loweralkyl, cycloalkyl or cycloalkylalkyl,
  d) —O-alkylenyl-,
  e) —S-alkylenyl-
  f) —S(O)-alkylenyl-,
  g) —S(O)$_2$-alkylenyl-,
  h) —N(R$_7$)-alkylenyl— wherein R$_7$ is defined as above,
  i) -alkylenyl-O—,
  j) -alkylenyl-S—,
  k) alkylenyl-N(R$_7$)— wherein R$_7$ is defined as above,
  l) alkylenyl or
  m) alkenylenyl;
or a pharmaceutically acceptable salt, ester or prodrug thereof.

Preferred compounds are compounds of the formula I wherein R$_1$ and R$_2$ are arylalkyl, R$_3$ is loweralkyl, R$_4$ is aryl, R$_5$ is a)
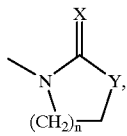

b)
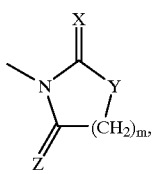

c)
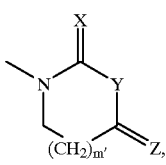

d)
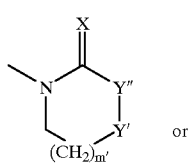

or e)
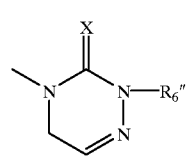

wherein X, Y, Y', Y", Z, R$_{6''}$, n, m and m' are defined as above and L$_1$ is —O-alkylenyl.

More preferred compounds are compounds of the formula I wherein R$_1$ and R$_2$ are benzyl or R$_1$ is benzyl and R$_2$ is loweralkyl, R$_3$ is loweralkyl, R$_4$ is (a) phenyl which is substituted with two loweralkyl groups and which is optionally substituted with a third substituent selected from the group consisting of loweralkyl, hydroxy, amino and halo or (b) pyridyl or pyrimidinyl either of which is substituted with two loweralkyl groups and which is optionally substituted with a third substituent selected from the group consisting of loweralkyl, hydroxy, amino and halo, R$_5$ is a)
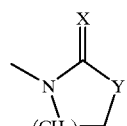

wherein n is 1 or 2, X is O or S and Y is —CH₂ or —NH—, b)
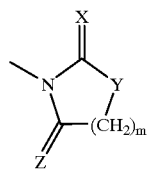

wherein n is 1 or 2, X is O, Y is —CH₂— and Z is O, c)
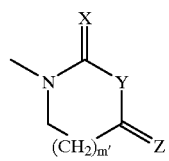

wherein m' is 1, X is O, Z is O and Y is —NH—, d)
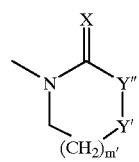

wherein m' is 1, X is O, Y" is —NH— and Y' is —NH— or e)
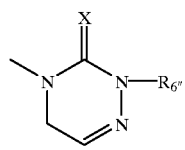

wherein X is O and R₆" is hydrogen and

L₁ is —O—CH₂—.

Even more preferred compounds are compounds of the formula I wherein R₁ and R₂ are benzyl or R₁ is benzyl and R₂ is isopropyl, R₃ is loweralkyl, R₄ is 2,6-dimethylphenyl which is optionally substituted with a third substituent selected from the group consisting of loweralkyl and halo, R₅ is a)
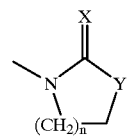

wherein n is 1 or 2, X is O or S and Y is —CH₂ or —NH—, b)
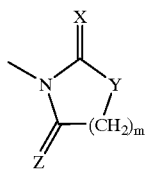

wherein m is 1 or 2, X is O, Y is —CH₂— and Z is O, c)
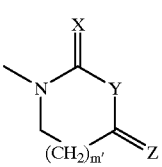

wherein m' is 1, X is O, Z is O and Y is —NH—, d)
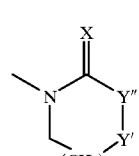

wherein m' is 1, X is O, Y" is —NH— and Y' is —NH— or e)
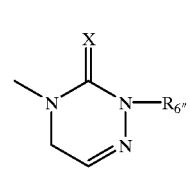

wherein X is O and R₆" is hydrogen and

L₁ is —O—CH₂—.

Most preferred compounds are compounds of the formula I wherein R₁ and R₂ are benzyl or R₁ is benzyl and R₂ is isopropyl, R₃ is loweralkyl, R₄ is 2,6-dimethylphenyl which is optionally substituted with a third substituent selected from the group consisting of loweralkyl and halo, R₅ is a)
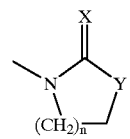

wherein n is 1 or 2, X is O or S and Y is —CH₂ or —NH—, b)
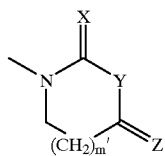

wherein m' is 1, X is O, Z is O and Y is —NH—, c)
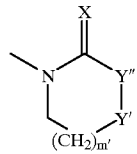

wherein m' is 1, X is O, Y" is —NH— and Y' is —NH— or d)
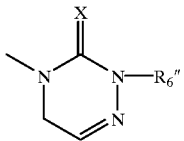

wherein X is O and $R_{6''}$ is hydrogen and
$L_1$ is —O—CH₂—.

Most highly preferred compounds are compounds of the formula I wherein $R_1$ and $R_2$ are benzyl or $R_1$ is benzyl and $R_2$ is isopropyl, $R_3$ is loweralkyl, $R_4$ is 2,6-dimethylphenyl which is optionally substituted with a third substituent selected from the group consisting of loweralkyl and halo, $R_5$ is

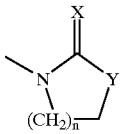

wherein n is 1 or 2, X is O or S and Y is —CH₂ or —NH— and
$L_1$ is —O—CH₂—.

Examples of highly and most highly preferred compounds of the formula I are selected from the group consisting of:

(2S,3S,5S)-2-(2,6-dimethylphenoxyacetyl)amino-3-hydroxy-5-[2S-(1-tetrahydro-pyrimid-2-onyl)-3-methylbutanoyl]amino-1,6-diphenylhexane;

(2S,3S,5S)-2-(2,6-Dimethylphenoxyacetyl)amino-3-hydroxy-5-(2S-(1-imidazolidin-2-onyl)-3,3-dimethylbutanoyl)amino-1,6-diphenylhexane;

(2S,3S,5S)-2-(2,6-dimethylphenoxyacetyl)amino-3-hydroxy-5-(2S-(1-imidazolidin-2-thionyl)-3-methylbutanoyl)amino-1,6-diphenylhexane;

(2S,3S,5S)-2-(2,4,6-trimethylphenoxyacetyl)amino-3-hydroxy-5-(2S-(1-imidazolidin-2-onyl)-3-methylbutanoyl)amino-1,6-diphenylhexane;

(2S,3S,5S)-2-(4-fluoro-2,6-dimethylphenoxyacetyl)amino-3-hydroxy-5-(2S-(1-imidazolidin-2-onyl)-3-methyl-butanoyl)amino-1,6-diphenylhexane;

(2S,3S,5S)-2-(2,6-dimethylphenoxyacetyl)amino-3-hydroxy-5-(2S-(1-pyrrolidin-2-onyl)-3-methyl-butanoyl)amino-1,6-diphenylhexane;

(2S,3S,5S)-2-(2,6-dimethylphenoxyacetyl) amino-3-hydroxy-5-(2S-(1-pyrrolidin-2,5-dionyl)-3-methyl-butanoyl) amino-1,6-diphenylhexane;

(2S,3S,5S)-2-(trans-3-(2,6-dimethylphenyl)propenoyl) amino-3-hydroxy-5-(2S-1-tetrahydropyrimidin-2-onyl)-3-methyl-butanoyl) amino-1,6-diphenylhexane;

(2S,3S,5S)-2-(3-(2,6-dimethylphenyl)propanoyl)amino-3-hydroxy-5-(2S-(1-tetrahydropyrimidin-2-onyl)-3-methyl-butanoyl)amino-1,6-diphenylhexane;

(2S,3S,5S)-2-(2,6-Dimethylphenoxyacetyl)amino-3-hydroxy-5-(2S-(1-tetrahydro-pyrimid-2,4-dionyl)-3-methylbutanoyl)amino-1,6-diphenylhexane;

(2S,3S,5S)-2-(2,6-Dimethylphenoxyacetyl) amino-3-hydroxy-5-(2S-(4-aza-1-tetrahydro-pyrimid-2-onyl)-3-methyl-butanoyl)amino-1,6-diphenylhexane;

(2S,3S,5S)-2-(2,6-Dimethylphenoxyacetyl) amino-3-hydroxy-5-(2S-(1-tetrahydro-pyrimid-2-onyl)-3-methylbutanoyl)amino-1-phenyl-6-methylheptane;

(2S,3S,5S)-2-(2,6-Dimethylphenoxyacetyl)amino-3-hydroxy-5-(2S-(1-tetrahydro-pyrimid-2,4-dionyl)-3-methylbutanoyl)amino-1-phenyl-6-methylheptane; and (2S,3S,5S)-2-(2,6-Dimethylphenoxyacetyl) amino-3-hydroxy-5-(2S-(4-aza-4,5-dehydro-1-pyrimid-2-onyl)-3-methyl-butanoyl)amino-1,6-diphenylhexane;

or a pharmaceutically acceptable salt, ester or prodrug thereof.

The most highly preferred compound of the formula I is (2S,3S,5S)-2-(2,6-Dimethylphenoxyacetyl) amino-3-hydroxy-5-[2S-(1-tetrahydro-pyrimid-2-onyl)-3-methyl butanoyl] amino-1,6-diphenylhexane;

or a pharmaceutically acceptable salt, ester or prodrug thereof.

In some circumstances it is preferred to be able to prepare (2S,3S,5S)-2-(2,6-Dimethylphenoxyacetyl) amino-3-hydroxy-5-[2S-(1-tetrahydro-pyrimid-2-onyl)-3-methylbutanoyl]amino-1,6-diphenylhexane (or a pharmaceutically acceptable salt, ester or prodrug thereof) as an amorphous solid. Such an amorphous solid can be prepared by dissolving (2S,3S,5S)-2-(2,6-Dimethylphenoxyacetyl) amino-3-hydroxy-5-[2S-(1-tetrahydro-pyrimid-2-onyl)-3-methylbutanoyl]amino-1,6-diphenylhexane in an organic solvent (for example, ethanol, isopropanol, acetone, acetonitrile and the like) and then adding the solution to water. Preferably, (2S,3S,5S)-2-(2,6-Dimethylphenoxyacetyl) amino-3-hydroxy-5-[2S-(1-tetrahydro-pyrimid-2-onyl)-3-methylbutanoyl]amino-1,6-diphenylhexane is dissolved in ethanol (from about 2 to about 4 mL/g) and the ethanolic solution is added with stirring to water (from about 10 about 100 mL/g) to provide amorphous (2S,3S,5S)-2-(2,6-Dimethylphenoxyacetyl)amino-3-hydroxy-5-[2S-(1-tetrahydro-pyrimid-2-onyl)-3-methylbutanoyl]amino-1,6-diphenylhexane.

Another embodiment of the present invention comprises an HIV protease inhibiting compound comprising a substituent of the formula II:

II
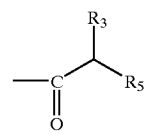

wherein R₃ is loweralkyl, hydroxyalkyl or cycloalkylalkyl; and $R_5$ is a)
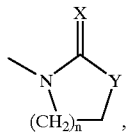

b)
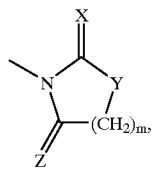

c)
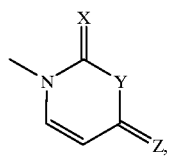

d)
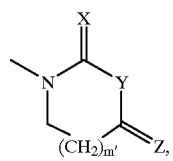

e)
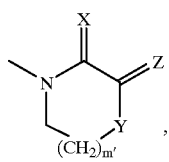

f)
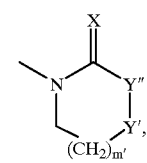

g)
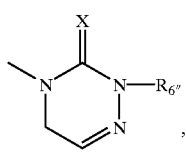

h)
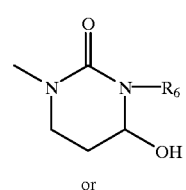

or i)
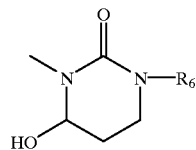

wherein n is 1, 2 or 3, m is 1, 2 or 3, m' is 1 or 2, X is O, S or NH, Y is —CH₂—, —O—, —S— or —N(R₆)— wherein R₆ is hydrogen, loweralkyl, cycloalkyl, cycloalkylalkyl, aryl or arylalkyl, Y" is —CH₂— or —N(R₆″)— wherein R₆″ is hydrogen, loweralkyl, cycloalkyl, cycloalkylalkyl, aryl or arylalkyl, Y' is —N(R₆′)— wherein R₆′ is hydrogen, loweralkyl, cycloalkyl, cycloalkylalkyl, aryl or arylalkyl, and Z is O, S or NH.

Preferred compounds are HIV protease inhibiting compounds comprising a substituent of the formula II wherein R₃ is loweralkyl and R₅ is a)
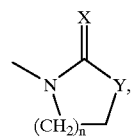

b)
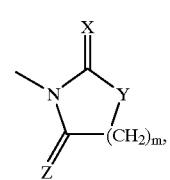

c)
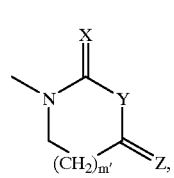

d)
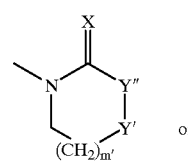

or e)
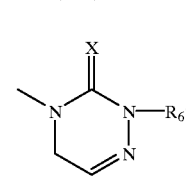

wherein X, Y, Y', Y", Z, R₆″, n, m and m' are defined as above.

More preferred compounds are HIV protease inhibiting compounds comprising a substituent of the formula II wherein R₃ is loweralkyl and R₅ is a)

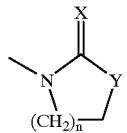

wherein n is 1 or 2, X is O or S and Y is —CH₂ or —NH—, b)

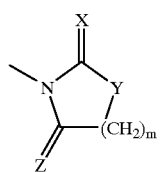

wherein m is 1 or 2, X is O, Y is —CH₂— and Z is O, c)

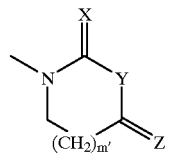

wherein m' is 1, X is O, Z is O and Y is —NH—, d)

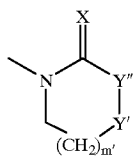

wherein m' is 1, X is O, Y" is —NH— and Y' is —NH— or e)

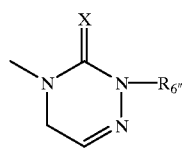

wherein X is O and R₆" is hydrogen.

Even more preferred compounds are HIV protease inhibiting compounds comprising a substituent of the formula II wherein R₃ is isopropyl and R₅ is a)

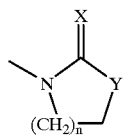

wherein n is 1 or 2, X is O or S and Y is —CH₂ or —NH—, b)

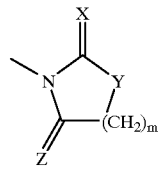

wherein m is 1 or 2, X is O, Y is —CH₂— and Z is O, c)

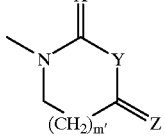

wherein m' is 1, X is O, Z is O and Y is —NH—, d)

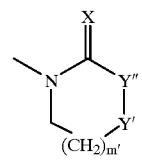

wherein m' is 1, X is O, Y" is —NH— and Y' is —NH— or e)

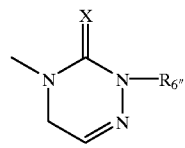

wherein X is O and R₆" is hydrogen.

Most preferred compounds are HIV protease inhibiting compounds comprising a substituent of the formula II wherein R₃ is isopropyl and R₅ is a)

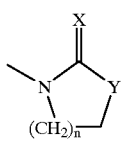

wherein n is 1 or 2, X is O or S and Y is —CH₂ or —NH—, b)

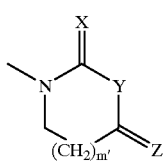

wherein m' is 1, X is O, Z is O and Y is —NH—,

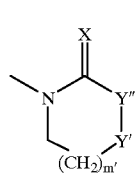

c)

wherein m' is 1, X is O, Y" is —NH— and Y' is —NH— or

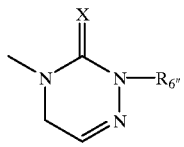

d)

wherein X is O and $R_{6''}$ is hydrogen.

Most highly preferred compounds are HIV protease inhibiting compounds comprising a substituent of the formula II wherein $R_3$ is isopropyl and $R_5$ is

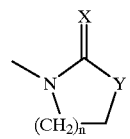

wherein n is 1 or 2, X is O or S and Y is —$CH_2$ or —NH—.

Examples of such HIV protease inhibiting compounds include:

cis-N-tert-butyl-decahydro-2-[2(R)-hydroxy-4-phenyl-3(S)-(2S-(1-tetrahydropyrimid-2-onyl)-3-methylbutanoyl)aminobutyl]-(4aS,8aS)-isoquinoline-3(S)-carboxamide;

cis-N-tert-butyl-decahydro-2-[2(R)-hydroxy-4-thiophenyl-3(S)-(2S-(1-tetrahydropyrimid-2-onyl)-3-methylbutanoyl)aminobutyl]-(4aS,8aS)-isoquinoline-3(S)-carboxamide; and 4-Amino-N-((2syn, 3S)-2-hydroxy-4-phenyl-3-(2S-(1-tetrahydropyrimid-2-onyl)-3-methylbutanoylamino)-butyl)-N-isobutyl-benzenesulfonamide; and the like;

or pharmaceutically acceptable salts thereof.

Such HIV protease inhibiting compounds comprising a substituent of the formula II can be prepared by coupling a suitable intermediate or precursor having an amino group (—$NH_2$ or —NHR* wherein R* is loweralkyl), a hydroxyl group (—OH) or a thiol group (—SH) to the compound of the formula III or a salt or an activated ester derivative thereof:

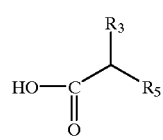

III wherein $R_3$ is loweralkyl, hydroxyalkyl or cycloalkylalkyl; and $R_5$ is

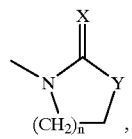

a)

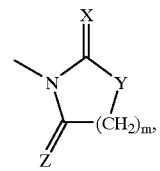

b)

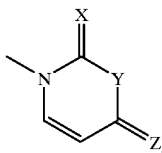

c)

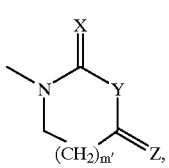

d)

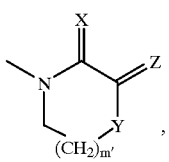

e)

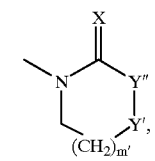

f)

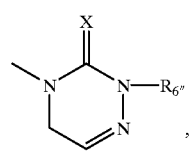

g)

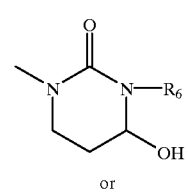

or h)

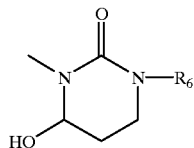

i)

wherein n is 1, 2 or 3, m is 1, 2 or 3, m' is 1 or 2, X is O, S or NH, Y is —CH$_2$—, —O—, —S— or —N(R$_6$)— wherein R$_6$ is hydrogen, loweralkyl, cycloalkyl, cycloalkylalkyl, aryl or arylalkyl, Y" is —CH$_2$— or —N(R$_{6''}$)— wherein R$_{6'}$, is hydrogen, loweralkyl, cycloalkyl, cycloalkylalkyl, aryl or arylalkyl, Y' is —N(R$_{6'}$)— wherein R$_{6'}$ is hydrogen, loweralkyl, cycloalkyl, cycloalkylalkyl, aryl or arylalkyl, and Z is O, S or NH.

Preferred compounds are compounds of the formula III or an activated ester derivative thereof wherein R$_3$ is loweralkyl and R$_5$ is

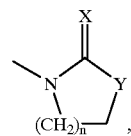

a)

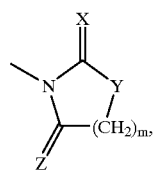

b)

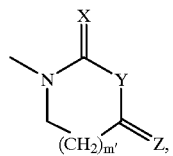

c)

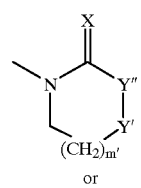

d)

or

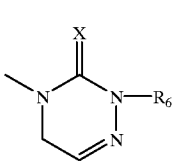

e)

wherein X, Y', Y", Z, R$_{6''}$, n, m and m' are defined as above.

More preferred compounds are compounds of the formula III or an activated ester derivative thereof wherein R$_3$ is loweralkyl and R$_5$ is

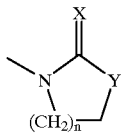

a)

wherein n is 1 or 2, X is O or S and Y is —CH$_2$ or —NH—, b)

wherein m is 1 or 2, X is O, Y is —CH$_2$— and Z is O, c)

wherein m' is 1, X is O, Z is O and Y is —NH—, d)

wherein m' is 1, X is O, Y" is —NH— and Y' is —NH— or

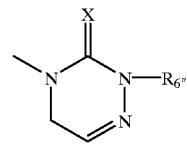

e)

wherein X is O and R$_{6''}$ is hydrogen.

Even more preferred compounds are compounds of the formula III or an activated ester derivative thereof wherein R$_3$ is isopropyl and R$_5$ is

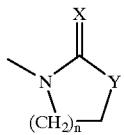

a)

wherein n is 1 or 2, X is O or S and Y is —CH$_2$ or —NH—, b)

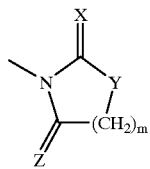

wherein m is 1 or 2, X is O, Y is —CH$_2$— and Z is O, c)

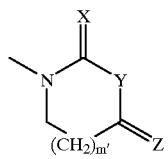

wherein m' is 1, X is O, Z is O and Y is —NH—, d)

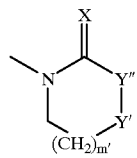

wherein m' is 1, X is O, Y" is —NH— and Y' is —NH— or e)

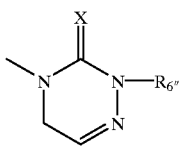

wherein X is O and R$_{6''}$ is hydrogen.

Most preferred compounds are compounds of the formula III or an activated ester derivative thereof wherein R$_3$ is isopropyl and R$_5$ is a)

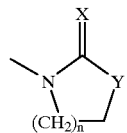

wherein n is 1 or 2, X is O or S and Y is —CH$_2$ or —NH—, b)

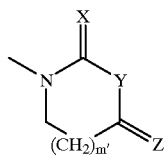

wherein m' is 1, X is O, Z is O and Y is —NH—, c)

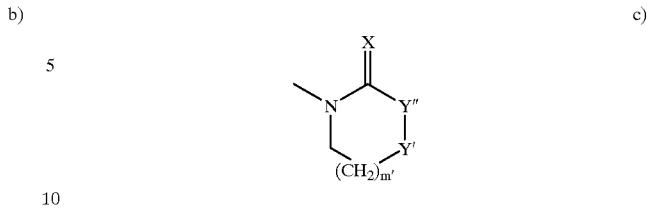

wherein m' is 1, X is O, Y" is —NH— and Y' is —NH— or d)

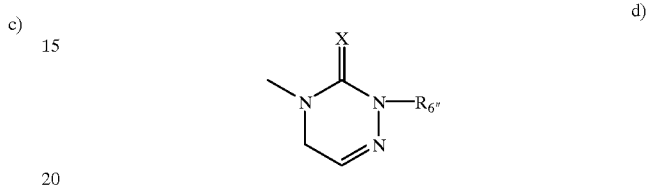

wherein X is O and R$_{6''}$ is hydrogen.

Most highly preferred compounds are compounds of the formula III or an activated ester derivative thereof wherein R$_3$ is isopropyl and R$_5$ is

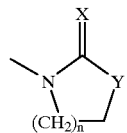

wherein n is 1 or 2, X is O or S and Y is —CH$_2$ or —NH—.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention.

The terms "S" and "R" configuration are as defined by the IUPAC 1974 Recommendations for Section E, Fundamental Stereochemistry, Pure Appl. Chem. (1976) 45, 13–30.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene and Wuts, "Protective Groups In Organic Synthesis," (John Wiley & Sons, New York (1991)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5- dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "activated ester derivative" as used herein refers to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters, thiophenol derived esters, propylphosphonic acid derived anhydrides and the like.

The term "alkanoyl" as used herein refers to $R_1C(O)$— wherein $R_{19}$ is a loweralkyl group.

The term "alkenylenyl" as used herein refers to a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The terms "alkoxy" and "thioalkoxy" as used herein refer to $R^{15}O$— and $R_{15}S$—, respectively, wherein $R_{15}$ is a loweralkyl group.

The term "alkoxyalkoxy" as used herein refers to $R_{22}O$—$R_{23}O$— wherein $R_{22}$ is loweralkyl as defined above and $R_{23}$ is an alkylenyl group. Representative examples of alkoxyalkoxy groups include methoxymethoxy, ethoxymethoxy, t-butoxymethoxy and the like.

The term "alkoxyalkyl" as used herein refers to an alkoxy group appended to a loweralkyl radical.

The term "alkoxycarbonyl" as used herein refers to $R_{20}C(O)$— wherein $R_{20}$ is an alkoxy group.

The term "alkylamino" as used herein refers to —NHR$_{16}$ wherein $R_{16}$ is a loweralkyl group.

The term "alkylaminocarbonyl" as used herein refers to $R_{21}C(O)$— wherein $R_{21}$ is an alkylamino group.

The term "alkylenyl" as used herein refers to a divalent group derived from a straight or branched chain saturated hydrocarbon having from 1 to 10 carbon atoms by the removal of two hydrogen atoms, for example methylene (—CH$_2$—), 1,2-ethylene(—CH$_2$CH$_2$—), 1,1-ethylene=CH—CH$_3$, 1,3-propylene (—CH$_2$CH$_2$CH$_2$—), 2,2-dimethylpropylene (—CH$_2$C(CH$_3$)$_2$CH$_2$—), and the like.

The term "aminocarbonyl" as used herein refers to —C(O)NH$_2$.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, alkoxy, alkoxycarbonyl, thioalkoxy, amino, alkylamino, dialkylamino, aminocarbonyl, mercapto, nitro, carboxaldehyde, carboxy and hydroxy.

The term "arylalkyl" as used herein refers to an aryl group as previously defined, appended to a loweralkyl radical, for example, benzyl and the like.

The term "cycloalkyl" as used herein refers to an aliphatic ring system having 3 to 8 carbon atoms including, but not limited to, cyclopropyl, cyclopentyl, cyclohexyl, and the like.

The term "cycloalkylalkyl" as used herein refers to a cycloalkyl group appended to a loweralkyl radical, including but not limited to cyclohexylmethyl.

The term "dialkylamino" as used herein refers to —NR$_{16}$R$_{17}$ wherein $R_{16}$ and $R_{17}$ are independently selected from loweralkyl groups.

The term "dialkylaminocarbonyl" as used herein refers to $R_{22}C(O)$— wherein $R_{22}$ is a dialkylamino group.

The term "halo" or "halogen" as used herein refers to —Cl, —Br, —I or —F.

The term "haloalkoxy" as used herein refers to $R_{18}O$— wherein $R_{18}$ is a haloalkyl group.

The term "haloalkyl" as used herein refers to a loweralkyl group in which one or more hydrogen atoms are replaced by halogen, for example, chloromethyl, chloroethyl, trifluoromethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl, bistetrahydorfuranyl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyi, furyl, thienyl, tetrahydrofuranyl, tetrahydrothienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

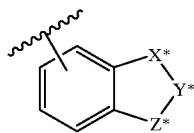

wherein X* is —CH$_2$—, —NH— or —O—, Y* is —C(O)— or [—C(R")$_2$—]$_v$ wherein R" is hydrogen or C$_1$-C$_4$-alkyl and v is 1, 2 or 3 and Z* is —O— or —NH—; such as 1,3-benzodioxolyl, 1,4-benzodioxanyl and the like.

Heterocyclics can be unsubstituted or substituted with one, two, three or four substituents independently selected from the group consisting of hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "hydroxyalkyl" as used herein refers to a loweralkyl radical to which is appended an hydroxy group.

The term "loweralkyl" as used herein refers to a straight or branched chain alkyl radical containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "thioalkoxyalkyl" as used herein refers to a thioalkoxy group appended to a loweralkyl radical.

The compound of the invention of formula I can be prepared as shown in Schemes I–IV. As outlined in Scheme I, intermediates 1 and 2 (wherein P$_1$ is an N-protecting group, for example, t-butyloxycarbonyl) can be coupled using standard peptide coupling reagents and methods, for example, reaction of 1 and 2 in the presence of 1-hydroxybenzotriazole and a diimide such as dicyclohexylcarbodiimide (DCC) or N-ethyl-N'-dimethylaminopropyl carbodiimide (EDAC) and the like to give. Alternatively, a salt or an activated ester derivative of intermediate 1 (for example, the acid chloride, prepared by reaction of the carboxylic acid with thionyl chloride) can be reacted with intermediate 2

Compound 3 can be N-deprotected to give compound 4. N-deprotection of 3 wherein P$_1$ (especially wherein P$_1$ is t-butyloxycarbonyl) is an acid labile N-protecting group can lead to formation of impurities resulting from migration of the acyl group R$_4$—L$_1$—C(O)— from the amino group to the hydroxyl group. The formation of this impurity can be minimized or eliminated by performing the deprotection using (1) trifluoroacetic acid in methylene chloride or (2) concentrated hydrochloric acid (from about 2 molar equivalents to about 6 molar equivalents, preferably, from about 2 molar equivalents to about 4 molar equivalents) in acetic acid at about room temperature. A preferred N-deprotection method comprises reacting compound X (wherein P$_1$ is t-butyloxycarbonyl) with concentrated hydrochloric acid (from about 10 to about 20 molar equivalents) in acetonitrile (from about 2 to about 10 liters/kilogram of compound I) at a temperature of from about 0° C. to about 5° C. Compound S or an activated ester derivative thereof can then be coupled to compound 4 to give the compound of the formula I (i.e., 6).

An alternative process is shown in Scheme IIA. Compound 7 (wherein P$_2$ is an N-protecting group, for example, benzyloxycarbonyl) can be coupled to compound 5, or a salt or an activated ester derivative thereof (for example, the acid chloride, prepared by reaction of the carboxylic acid with thionyl chloride), to give 8. Compound 8 can be N-deprotected to give 9. Compound 9 can be coupled with compound 1, or an activated ester derivative thereof, to give the compound of the formula I (i.e., 6).

Scheme IIB shows a preferred alternative process wherein the N-protected amino alcohol 7a (P$_3$ is hydrogen and P$_4$ is an N-protecting group or both P$_3$ and P$_4$ are N-protecting groups, preferably, P$_3$ and P$_4$ are benzyl) is reacted with from about 1 to about 1.3 molar equivalents of carboxylic acid 5 or a salt or an activated ester derivative thereof (for example, the acid chloride, prepared by reaction of the carboxylic acid with thionyl chloride in ethyl acetate or THF or oxalyl chloride in toluene/DMF and the like) in the presence of from about 1.0 to about 4.0 molar equivalents (preferably, from about 2.5 to about 3.5 molar equivalents) of an organic amine base (for example, imidazole, 1-methylimidazole, 2-methylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine or N-methylmorpholine and the like) or from about 1 to about 20 molar equivalents of an inorganic base (for example, sodium carbonate or sodium bicarbonate and the like) in an inert solvent (for example, ethyl acetate, dimethylformamide, THF, acetonitrile, isopropyl acetate or toluene and the like) at a temperature of from about 0° C. to about 50° C. to provide compound 8a. Preferred organic amine bases include imidazole and 1,2,4-triazole.

N-Debenzylation of 8a (for example, using hydrogen and a hydrogenation catalyst or Pd/C and a formic acid salt (for example, ammonium formate and the like) or Pd/C and formic acid and the like) provides 9. Compound 9 can be advantageously purified by crystallization with an organic carboxylic acid (for example, S-pyroglutamic acid, succinic acid or fumaric acid and the like). A preferred organic carboxylic acid is S-pyroglutamic acid.

Compound 9 (or an organic carboxylic acid salt of compound 9) is reacted with from about 1.0 to about 1.3 molar equivalents of carboxylic acid 1 or a salt or an activated ester derivative thereof (for example, the acid chloride) in the presence of (1) from about 4 to about 8 molar equivalents (preferably, from about 5 to about 7 molar equivalents) of an inorganic base (for example, NaHCO$_3$, Na$_2$CO$_3$, KHCO$_3$, K$_2$CO$_3$, NaOH or KOH and the like) in an inert solvent (for example, 1:1 ethyl acetate/water or isopropyl acetate/water or toluene/water or THF/water and the like) at about room temperature or (2) from about 1.0 to about 4.0 molar equivalents (preferably, from about 2.5 to about 3.5 molar equivalents) of an organic amine base (for example, imidazole, 1-methylimidazole, 2-methylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine or N-methylmorpholine and the like) in an inert solvent (for example, ethyl acetate, isopropyl acetate, THF, toluene, acetonitrile, dimethylformamide and the like) at a temperature of from about 0° C. to about 50° C. to provide compound .

In a preferred embodiment of the invention (shown in Scheme III), intermediate compound a has the formula of compound 10 (R$_3$ is as defined for the compound of formula I and is preferably isopropyl). Compound 10 can be prepared in variety ways as shown in Scheme III. In one method, amino acid 11 (either as the free carboxylic acid or as the carboxylic acid ester (i.e., loweralkyl ester)) is converted to carbamate 12 (R" is phenyl, loweralkyl-substituted phenyl, halo-substituted phenyl, nitro-substituted phenyl, trifluoromethylphenyl and the like) by reaction with the appropriate chloroformate ester and the like. Reaction of carbamate 12 with from about 1.0 to about 1.5 molar equivalents of amine 13 or an acid addition salt thereof (Q is a leaving group, for example, Cl, Br or I, or a sulfonate such as methanesulfonate, triflate, p-toluenesulfonate, benzenesulfonate and the like) in an inert solvent (for example, THF, methyl t-butyl ether, dimethoxyethane, THF/water, dimethoxyethane/water, toluene or heptane and the like) in the presence of a base (for example, LiOH, NaOH, $Li_2CO_3$, $Na_2CO_3$, lithium phenoxide or sodium phenoxide and the like) in the amount of from about 2.5 to about 3.5 molar equivalents provides urea 14. Urea 14 can be isolated and reacted further or can be converted in situ to cyclic urea 10 by reaction in an inert solvent (for example, THF, dimethoxyethane, methyl t-butyl ether, toluene or heptane and the like) with a base (for example, potassium t-butoxide, sodium hydride, potassium hydride or dimethylaminopyridine and the like) in the amount of from about 2.0 to about 5.0 molar equivalents. If the amino acid ester of 11 was the starting material, the ester is then hydrolyzed to provide the carboxylic acid 10.

Alternatively, amino acid 11 (either as the free carboxylic acid or as the carboxylic acid ester) is converted to urea 14 by reaction with from about 1.0 to about 1.5 molar equivalents of isocyanate 15 (Q is a leaving group, for example, Cl, Br or I, or a sulfonate such as methanesulfonate, triflate, p-toluenesulfonate, benzenesulfonate and the like) in an inert solvent (for example, THF, dimethoxyethane, methyl t-butyl ether, toluene or heptane and the like) in the presence of a base.

In yet another alternative, amino acid 11 (either as the free carboxylic acid or as the carboxylic acid ester) is converted to diamine 16 by reaction with from about 1.0 to about 1.5 molar equivalents of amine 13 or an N-protected derivative thereof (Q is a leaving group, for example, Cl, Br or I, or a sulfonate such as methanesulfonate, triflate, p-toluenesulfonate, benzenesulfonate and the like) in an inert solvent (for example, THF, dimethoxyethane, methyl t-butyl ether, toluene or heptane and the like) in the presence of a base (for example, NaH or potassium t-butoxide and the like) in the amount of from about 1.0 to about 4.0 molar equivalents. N-deprotection is required if the N-protected derivative of 13 was used. Reaction of diamine 16 with a carbonyl equivalent 17 (for example, phosgene, carbonyldiimidazole and the like wherein Q' and Q'' are leaving groups such as Cl, Br, I, —O-loweralkyl, —O-aryl or imidazolyl and the like) in an inert solvent (for example, THF, dimethoxyethane, methyl t-butyl ether, toluene or heptane and the like) in the presence of a base (for example, NaH or potassium t-butoxide and the like and the like) in the amount of from about 2.0 to about 4.0 molar equivalents provides cyclic urea 10. If the amino acid ester of 11 was the starting material, the ester is then hydrolyzed to provide the carboxylic acid 10.

In yet another alternative shown in Scheme IV, compound 11 (either as the free carboxylic acid or as the carboxylic acid ester (i.e., loweralkyl ester)) is reacted with acrylonitrile according to J. Am. Chem. Soc. 72, 2599 (1950) to give aminonitrile 18. Alternatively, acrylonitrile can be replaced with 3-chloropropionitrile to provide 18. N-protection of aminonitrile 18 as the carbamate ($R_{30}$ is loweralkyl or phenyl or haloalkyl (for example, 2-chloroethyl, 2-bromoethyl and the like) and the like) using standard conditions (for example, reaction of the amine with the appropriate chloroformate ester (ClC(O)$OR_{30}$ wherein $R_{30}$ is loweralkyl, phenyl, haloalkyl and the like) neat or in an inert solvent (for example, water, THF and the like) in the presence of an inorganic base (for example, NaOH, KOH, $K_2CO_3$ and the like) or an organic base (for example, an alkylamine or dialkylamine and the like) and the like) provides compound 19. Hydrogenation of 1 in the presence of a catalyst (for example, Ni—Al alloy (basic) or Raney nickel (neutral or basic) or $PtO_2$ (acidic) and the like) in an inert solvent (for example, water or methanol or ethanol or THF and the like) provides cyclic urea 10. In a preferred process, compound 19 is hydrogenated in the presence of a Ni—Al alloy catalyst in an inert solvent (for example, water or methanol or ethanol or THF and the like) in the presence of a base (for example, KOH or NaCH or LiOH or an organic amine base and the like) in the amount of from about 1.1 to about 5 molar equivalents to provide cyclic urea 10. If the amino acid ester of 11 was the starting material, the ester is then hydrolyzed to provide the carboxylic acid 10.

Alternatively, hydrogenation of compound 18 (as described above for compound 19) provides diamine 16 which can be converted to compound 10 as previously described. If the amino acid ester of 11 was the starting material, the ester is then hydrolyzed to provide the carboxylic acid 10.

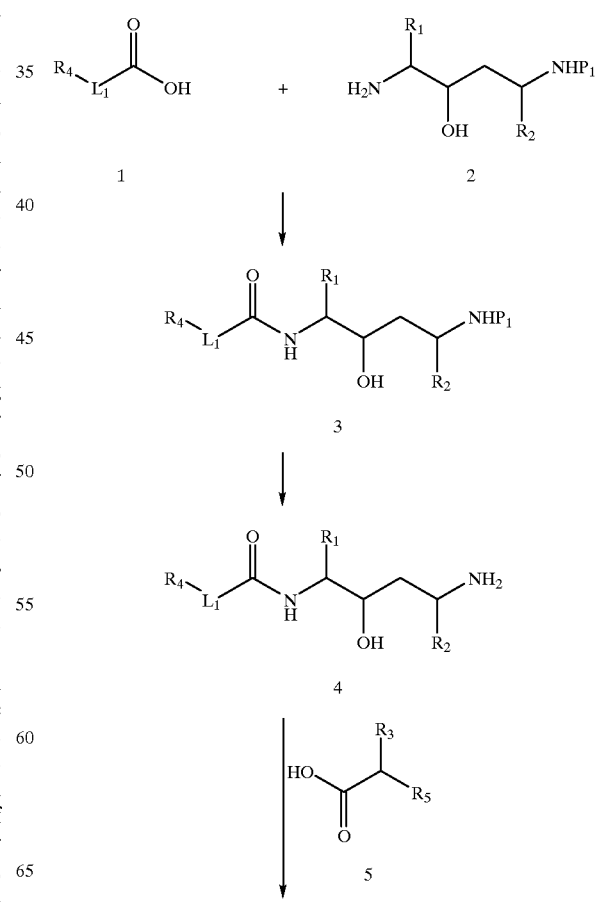

Scheme I

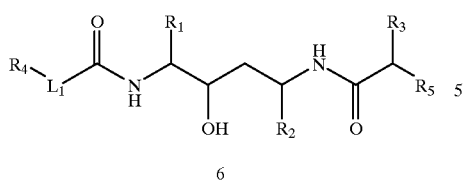
6
Scheme IIA
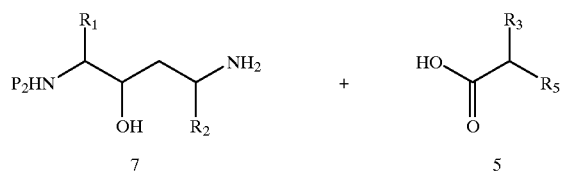
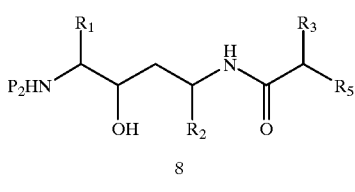
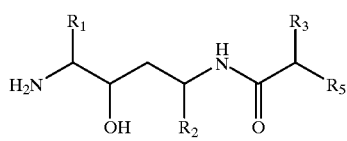
6
Scheme IIB
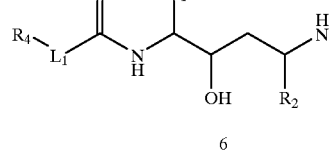
$P_3 = P_4 = \text{benzyl}$
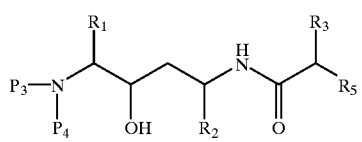
8a
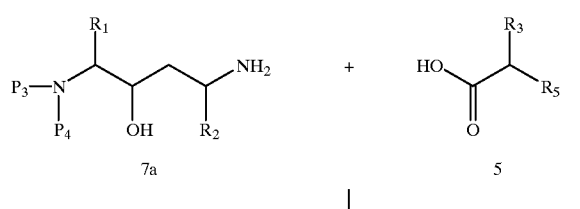
6
Scheme III
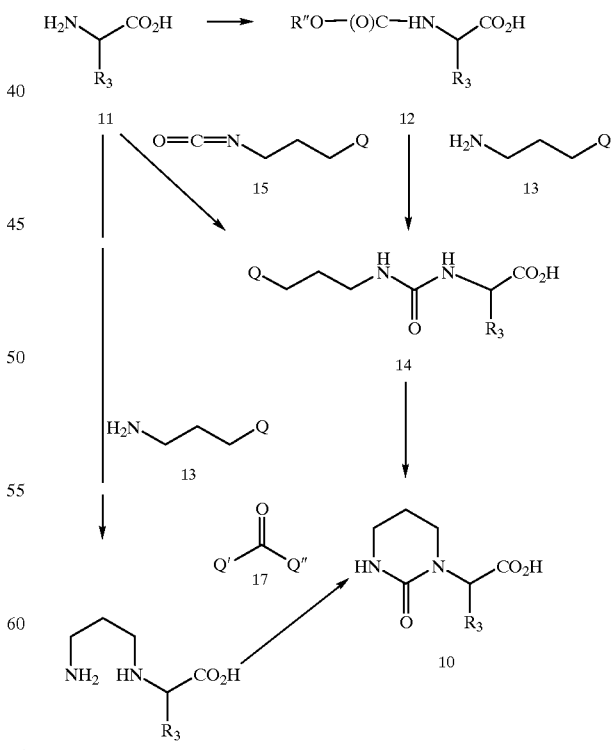

Scheme IV

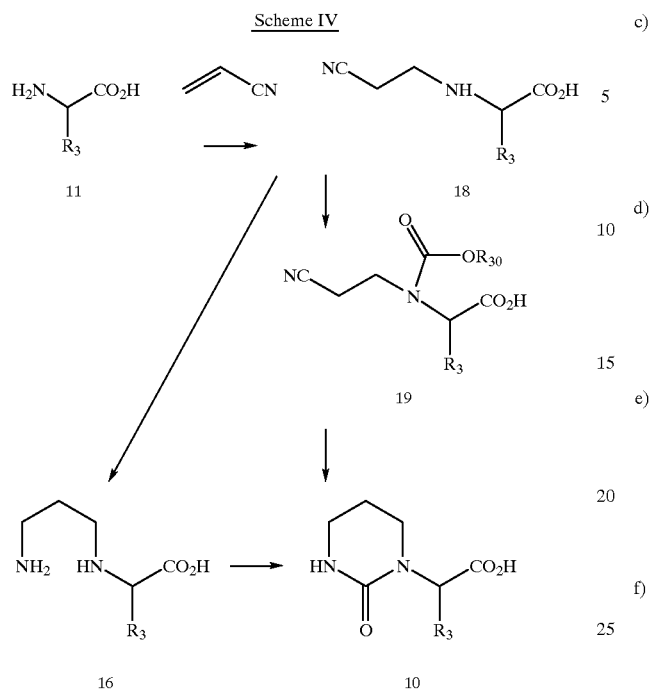

Key intermediates for the preparation of the compounds of the invention include compounds of the formula III as described above and compounds of the formula IV:

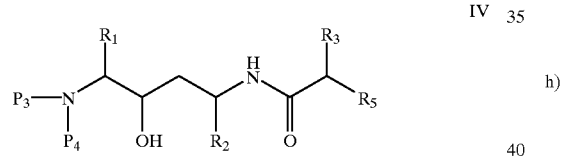   IV or a salt thereof, wherein $P_3$ and $P_4$ are independently selected from hydrogen or an N-protecting group;
$R_1$ and $R_2$ are independently selected from the group consisting of loweralkyl, cycloalkylalkyl and arylalkyl;
$R_3$ is loweralkyl, hydroxyalkyl or cycloalkylalkyl; and
$R_5$ is a) 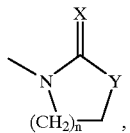

b) 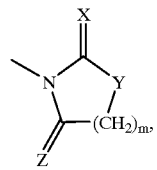

c) 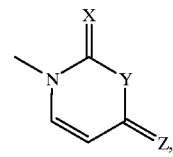

d) 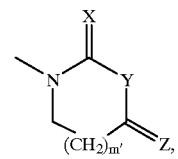

e) 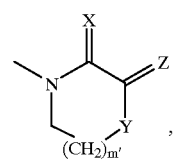

f) 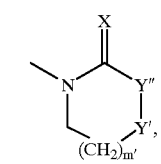

g) 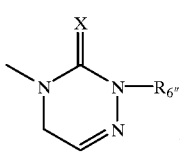

h) 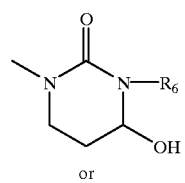

or i) 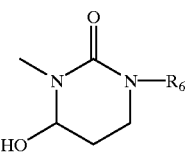

wherein n is 1, 2 or 3, m is 1, 2 or 3, m' is 1 or 2, X is O, S or NH, Y is —$CH_2$—, —O—, —S—or —N($R_6$)— wherein $R_6$ is hydrogen, loweralkyl, cycloalkyl, cycloalkylalkyl, aryl or arylalkyl, Y" is —$CH_2$— or —N($R_{6''}$)— wherein $R_{6''}$ is hydrogen, loweralkyl, cycloalkyl, cycloalkylalkyl, aryl or arylalkyl, Y' is —N($R_{6'}$)— wherein $R_{6'}$ is hydrogen, loweralkyl, cycloalkyl, cycloalkylalkyl, aryl or arylalkyl, and Z is O, S or NH.

Preferred compounds are compounds of the formula IV wherein $P_3$ and $P_4$ are hydrogen or benzyl, $R_1$ and $R_2$ are arylalkyl, $R_3$ is loweralkyl and $R_5$ is a)

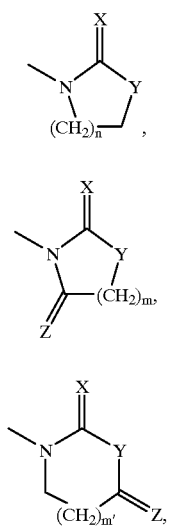

b)

c)

d)

e)

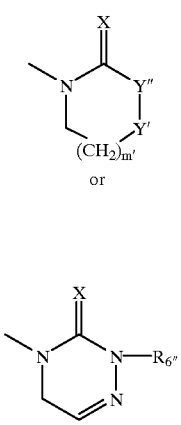

or

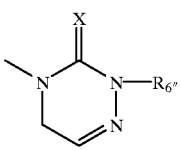

wherein X, Y, Y', Y", Z, R$_6$", n, m and m' are defined as above.

More preferred compounds are compounds of the formula IV wherein R$_1$ and R$_2$ are benzyl or R$_1$ is benzyl and R$_2$ is loweralkyl, R$_3$ is loweralkyl and R$_5$ is a)

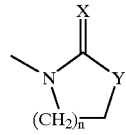

wherein n is 1 or 2, X is O or S and Y is —CH$_2$ or —NH—, b)

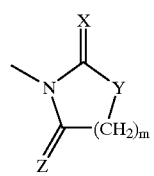

wherein m is 1 or 2, X is O, Y is —CH$_2$— and Z is O, c)

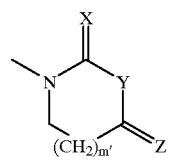

wherein m' is 1, X is O, Z is N and Y is —NH—, d)

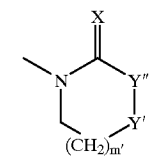

wherein m' is 1, X is O, Y" is —NH— and Y' is —NH— or e)

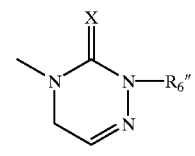

wherein X is O and R$_6$' is hydrogen.

Even more preferred compounds are compounds of the formula IV wherein R$_1$ and R$_2$ are benzyl or R$_1$ is benzyl and R$_2$ is isopropyl, R$_3$ is loweralkyl and R$_5$ is a)

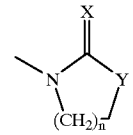

wherein n is 1 or 2, X is O or S and Y is —CH$_2$ or —NH—, b)

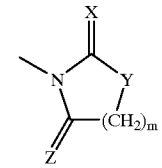

wherein m is 1 or 2, X is O, Y is —CH$_2$— and Z is O, c)

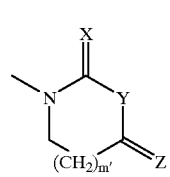

wherein m' is 1, X is O, Z is O and Y is —NH—,

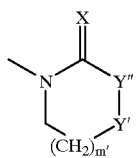

d)

wherein m' is 1, X is O, Y" is —NH— and Y' is —NH— or

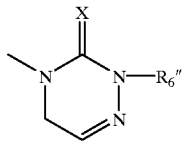

e)

wherein X is O and $R_6'$ is hydrogen.

Most preferred compounds are compounds of the formula IV wherein $R_1$ and $R_2$ are benzyl or $R_1$ is benzyl and $R_2$ is isopropyl, $R_3$ is loweralkyl and $R_5$ is

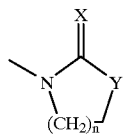

a)

wherein n is 1 or 2, X is O or S and Y is —CH$_2$ or —NH—,

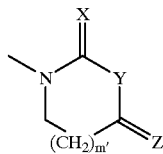

b)

wherein m' is 1, X is O, Z is O and Y is —NH—,

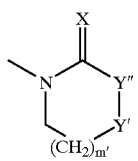

c)

wherein m' is 1, X is O, Y" is —NH— and Y' is —NH— or

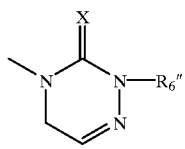

d)

wherein X is O and $R_6''$ is hydrogen.

Most highly preferred compounds are compounds of the formula IV wherein $R_1$ and $R_2$ are benzyl or $R_1$ is benzyl and $R_2$ is isopropyl, $R_3$ is loweralkyl and $R_5$ is

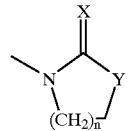

wherein n is 1 or 2, X is O or S and Y is —CH$_2$ or —NH—.

Preferred salts of the compound of formula IV are organic carboxylic acid salts, especially the (S)-pyroglutamic acid salt.

The following examples will serve to further illustrate the preparation of the novel compounds of the invention.

EXAMPLE 1

(2S,3S,5S)-2-(2,6-dimethylphenoxyacetyl)amino-3-hydroxy-5-[2S-(1-imidazolidin-2-onyl)-3-methyl-butanoyl]amino-1,6-diphenylhexane A. N,N-Dibenzyl-(L)-phenylalanine Benzyl Ester.

A solution containing L-phenylalanine (161 kg, 975 moles), potassium carbonate (445 kg, 3220 moles), water (675 L), ethanol (340 L), and benzyl chloride (415 kg, 3275 moles) was heated to 90±15° C. for 10–24 hours. The reaction mixture was cooled to 60° C. and the lower aqueous layer was removed. Heptane (850 L) and water (385 L) were added to the organics, stirred, and the layers separated. The organics were then washed once with a water/methanol mixture (150 L/50 L). The organics were then stripped to give the desired product as an oil, which was carried on in the next step without purification.

IR (neat) 3090, 3050, 3030, 1730, 1495, 1450, 1160 cm$^{-1}$, $^1$H NMR (300 MHz, CDCl$_3$) δ 7.5–7.0 (m, 20H), 5.3 (d, 1H, J=13.5 Hz), 5.2 (d, 1H, J=13.5 Hz), 4.0 (d, 2H, J=15 Hz), 3.8 (t, 2H, J=8.4 Hz), 3.6 (d, 2H, J=15 Hz), 3.2 (dd, 1H, J=8.4, 14.4 Hz), $^{13}$C NMR (300 MHz, CDCl$_3$) δ 172.0, 139.2, 138.0, 135.98.2, 128.1, 128.1, 126.9, 126.2, 66.0, 62.3, 54.3, 35.6.

$[\alpha]_D$ -79° (c=0.9, DMF).

B. (4S)-4-(N,N-Dibenzylamino)-3-oxo-5-phenyl-pentanonitrile

A solution containing the product of Example 1 A (i.e., benzyl ester) (approx. 0.45 moles) in 520 mL tetrahydrofuran and 420 mL acetonitrile was cooled to –40° C. under nitrogen. A second solution containing sodium amide (48.7 g, 1.25 moles) in 850 mL tetrahydrofuran was cooled to -40° C. To the sodium amide solution was slowly added 75 mL acetonitrile and the resulting solution was stirred at –40° C. for more than 15 minutes. The sodium amide/acetonitrile solution was then slowly added to the benzyl ester solution at –40° C. The combined solution was stirred at -40° C. for one hour and then quenched with 1150 mL of a 25% (w/v) citric acid solution. The resulting slurry was warmed to ambient temperature and the organics separated. The organics were then washed with 350 mL of a 25% (w/v) sodium chloride solution, then diluted with 900 mL heptane. The organics were then washed three times with 900 mL of a 5% (w/v) sodium chloride solution, two times with 900 mL of a 10% methanolic water solution, one time with 900 mL of a 15% methanolic water solution, and then one time with 900 mL of a 20% methanolic water solution. The organics were stripped and the resulting material dissolved into 700 mL of hot ethanol. Upon cooling to room temperature, the desired product precipitated. Filtration gave the desired product in 59% yield from the L-phenylalanine.

IR (CHCl$_3$) 3090, 3050, 3030, 2250, 1735, 1600, 1490, 1450, 1370, 1300, 1215 cm$^{-1}$, $^1$H NMR (CDCl$_3$) 37.3 (m, 15H), 3.9 (d, 1H, J=19.5 Hz), 3.8 (d, 2H, J=13.5 Hz), 3.6 (d, 2H, J=13.5 Hz), 3.5 (dd, 1H, J=4.0, 10.5 Hz), 3.2 (dd, 1H, J=10.5, 13.5 Hz), 3.0 (dd, 1H, J=4.0, 13.5 Hz), 3.0 (d, 1H, J=19.5 Hz), $^{13}$C NMR (300 MHz, CDCl$_3$) δ 197.0, 138.4, 138.0, 129.5, 129.0, 128.8, 128.6, 127.8, 126.4, 68.6, 54.8, 30.0, 28.4. [α]$_D$ −95° (c=0.5, DMF).

C. (5S)-2-Amino-5-(N,N-dibenzylamino)-4-oxo-1,6-diphenylhex-2-ene.

To a −5° C. solution of the nitrile product of Example 1 B (90 Kg, 244 moles) in tetrahydrofuran (288 L), was added benzylmagnesium chloride (378 Kg, 2M in THF, 708 moles). The solution was warmed to ambient temperature and stirred until analysis showed no starting material. The solution was then recooled to 5° C. and slowly transferred to a solution of 15% citric acid (465 kg). Additional tetrahydrofuran (85 L) was used to rinse out the original container and the rinse was added to the citric acid quench container. The organics were separated and washed with 10% sodium chloride (235 kg) and stripped to a solid. The product was stripped again from ethanol (289 L) and then dissolved in 80° C. ethanol (581 L)). After cooling to room temperature and stirring for 12 hours, the resulting product was filtered and dried in a vacuum oven at 30° C. to give approx. 95 kg of the desired product. mp 101–102° C., IR (CDCl$_3$) 3630, 3500, 3110, 3060, 3030, 2230, 1620, 1595, 1520, 1495, 1450 cm$^{-1}$, $^1$H NMR (300 MHZ, CDCl$_3$) d 9.8 (br s, 1H), 7.2 (m, 20H), 5.1 (s, 1H), 4.9 (br s, 1H), 3.8 (d, 2H, J=14.7 Hz), 3.6 (d, 2H, J=14.7 Hz), 3.5 (m, 3H), 3.2 (dd, 1H, J=7.5, 14.4 Hz), 3.0 (dd, 1H, J=6.6, 14.4 Hz), $^{13}$C NMR (CDCl$_3$) d 198.0, 162.8, 140.2, 140.1, 136.0, 129.5, 129.3, 128.9, 128.7, 128.1, 128.0, 127.3, 126.7, 125.6, 96.9, 66.5, 54.3, 42.3, 32.4. [α]$_D$ −147° (c=0.5, DMF).

D. (2S,3S,5S)-5-Amino-2-(N,N-dibenzylamino)-3-hydroxy-1,6-diphenyl-hexane i) A suspension of sodium borohydride (6.6 kg, 175 moles) in tetrahydrofuran (157 L) was cooled to less than −10±5° C. Methanesulfonic acid (41.6 kg, 433 moles) was slowly added and the temperature kept below 0° C. during the addition. Once the addition was complete, a solution of water (6 L, 333 moles), the product of Example 1C (20 kg, 43 moles) and tetrahydrofuran (61 L) was slowly added while maintaining the temperature below 0° C. during the addition. The mixture was stirred for not less than 19h at 0±5° C.

ii) To a separate flask was added sodium borohydride (6.6 kg, 175 moles) and tetrahydrofuran (157 L). After cooling to −5±5° C., trifluoroacetic acid (24.8 kg, 218 moles) was added while maintaining the temperature below 15° C. The solution was stirred 30 min at 15±5° C. and was then added to the reaction mixture resulting from step i, keeping the temperature at less than 20° C. This was stirred at 20±5° C. until reaction was complete. The solution was then cooled to 10±5° C. and quenched with 3N NaOH (195 kg). After agitating with tert-butyl methyl ether (162 L), the organic layer was separated and washed one time with 0.5N NaOH (200 kg), one time with 20% w/v aqueous ammonium chloride (195 kg), and two times with 25% aqueous sodium chloride (160 kg). The organics were stripped to give the desired product as an oil which was used directly in the next step.

IR (CHCl$_3$) 3510, 3400, 3110, 3060, 3030, 1630, $^1$H NMR (300 MHz, CDCl$_3$) 37.2 (m, 20H), 4.1 (d, 2H, J=13.5 Hz), 3.65 (m, 1H), 3.5 (d, 2H, J=13.5 Hz), 3.1 (m, 2H), 2.8 (m, 1H), 2.65 (m, 3H), 1.55 (m, 1H), 1.30 (m, 1H), $^{13}$C NMR (300 MHz, CDCl$_3$) δ 140.8, 140.1, 138.2, 129.4, 129.4, 128.6, 128.4, 128.3, 128.2, 126.8, 126.3, 125.7, 72.0, 63.6, 54.9, 53.3, 46.2, 40.1, 30.2.

E. (2S,3S,5S)-2-(N,N-Dibenzylamino)-3-hydroxy-5-(t-butyloxycarbonylamino)-1,6-diphenylhexane To a solution of the [2S,3S,5S]-2-N,N-dibenzylamino-3-hydroxy-5-amino-1,6-diphenylhexane (approx. 105 kg, 226 moles) in MTBE (1096 L), was added BOC Anhydride (65 kg, 373 moles) and 10% potassium carbonate (550 kg). This mixture was stirred until reaction was complete (approx. 1 hour). The bottom layer was removed and the organics were washed with water (665 L). The solution was then stripped to give the desired product as an oil. 300 MHz $^1$H NMR (CDCl$_3$) δ 1.40 (s, 9H), 1.58 (s, 2H), 2.45–2.85 (m, 4H), 3.05 (m, 1H), 3.38 (d, 2H), 3.6 (m, 1H), 3.79 (m, 1H), 3.87 (d, 2H), 4.35 (s, 1H), 4.85 (s, broad, 1H), 7.0–7.38 (m, 20H).

F-1. (2S,3S,5S)-2-Amino-3-hydroxy-5-(t-butyloxycarbonylamino)—1,6-diphenylhexane To a stirred solution of [2S,3S,5S]-2-N,N-dibenzylamino-3-hydroxy-5-t-butyloxycarbonylamino-1,6-diphenylhexane (12 g, 21.3 mmol) in methanol (350 mL) was charged ammonium formate (8.05 g, 128 mmol, 6.0 eq) and 10% palladium on carbon (2.4 g). The solution was stirred under nitrogen at 60 ° C. for three hours and then at 75° C. for 12 hours. An additional amount of ammonium formate (6 g) and 10% palladium on carbon (1.5 g) was added as well as 1 mL of glacial acetic acid. The reaction was driven to completion within 2 hours at a reflux temperature. The reaction mixture was then cooled to room temperature and then filtered through a bed of celite. The filter cake was washed with methanol (75 mL) and the combined filtrates were concentrated under reduced pressure. The residue was taken up in 1 N NaOH (300 mL) and extracted into methylene chloride (2×200 mL). The combined organic layers were washed with brine (250 mL) and dried over sodium sulfate. Concentration of the solution under reduced pressure provided the desired product as a light colored oil which slowly crystallized upon standing (5 g). Further purification of the product could be accomplished by flash chromatography (silica gel, 5% methanol in methylene chloride). 300 MHz $^1$H NMR (CDCl$_3$) δ 1.42 (s, 9H), 1.58 (m, 1H), 1.70 (m, 1H), 2.20 (s, broad, 2H), 2.52 (m, 1H), 2.76–2.95 (m, 4H), 3.50 (m, 1H), 3.95 (m, 1H), 4.80 (d, broad, 1H), 7.15–7.30 (m, 1OH).

F-2. [2S,3S,5S]-2-Amino-3-hydroxy-5-t-butyloxycarbonylamino-1,6-diphenylhexane succinate salt To a solution of [2S,3S,5S]-2-N,N-dibenzylamino-3-hydroxy-5-t-butyloxycarbonylamino-1,6-diphenylhexane (approx. 127 kg, 225 moles) in methanol (437 L), was added a methanolic (285 L) slurry of 5% palladium on carbon (24 kg). To this was added a solution of ammonium formate (84 kg, 1332 moles) in methanol (361 L). The solution was heated to 75° C. for 6–12 hours and then cooled to room temperature. Solids were filtered from the reaction mixture using a filter coated with filteraid (Celite) and the methanol was stripped from the reaction mixture using heat and vacuum (up to 70° C.). The residue was dissolved in isopropyl acetate (4400 kg) with heat (40° C.) and then washed with a 10% sodium carbonate solution (725 kg), and finally with water (665 L). Both of the washes were performed at 40° C. to keep the product in solution. The solvent was removed under vacuum with heat (up to 70° C.). Isopropyl alcohol (475 L) was then added and stripped off to remove residual solvents. Isopropanol (1200 L) was added to the residue and stirred until homogeneous. To this solution was added a solution of succinic acid (15–40 kg) in isopropanol (1200 L). The solution jacket was heated to 70° C. to dissolve all of the solids and then allowed to slowly cool to room temperature and stir for 6 hours. The solution was then filtered to give the desired product as a white solid (55–80 kg).

mp: 145–146° C. $^1$H NMR: (Me$_2$SO-d$_6$, 300 MHz) δ 0.97 (d, 3H, IPA), 1.20 (s, 9H), 1.57 (t, 2H), 2.20 (s, 2H, succinic acid), 2.55 (m, 2H), 2.66 (m, 2H), 2.98 (m, 1H), 3.42 (m, 1H), 3.70 (m, 1H), 3.72 (m, 1H, IPA), 6.60 (d, 1H, amide NH), 7.0–7.3 (m, 1OH).

$^1$H NMR: (CD$_3$OD, 300 MHz) δ 1.11 (d, 3H, J=7 Hz, IPA), 1.29 (s, 9H), 1.70 (m, 2H), 2.47 (s, 2H, succinic acid), 2.65 (m, 2H), 2.85 (m, 2H), 3.22 (m, 1H), 3.64 (m, 1H), 3.84 (m, 1H), 7.05–7.35 (m, 1OH).

G. Ethyl 2,6-dimethylphenoxy Acetate

To a solution of 2,6-dimethylphenol (8.0 g, 66 mmole) in dioxane (600 ml) was added ethyl bromoacetate (18.2 ml, 164 mmole) and cesium carbonate (58 g, 176 mmole). The reaction mixture was heated at reflux for 18 h, cooled to room temperature, filtered and concentrated in vacuo. Purification by silica gel column chromatography (5% to 20% ether in hexane) provided the desired compound (80%). 300 MHz 1H NMR (CDCl$_3$) δ 1.35 (t, J=7.5 Hz, 3H), 2.30 (s, 6H), 4.31 (q, J=7.5 Hz, 2H), 4.40 (s, 2H), 7.0 (m, 3H).

H. 2,6-Dimethylphenoxy Acetic Acid

To a solution of the compound from Example of G (5.15 g, 24.7 mmole) in m ethanol (170 ml) and water (56 ml) was added 5.3 1 of lithium hydroxide at 0° C., the solution was stirred for 1.5 h at RT and concentrated in vacuo. The residue was acidified with 0.5M HCl and extracted with ethyl acetate (300 ml). The organic layer was dried and concentrated to give a white solid (4.05 g, 91%). 300 MHz $^1$7H NMR (CDCl$_3$) 2.30 (s, 6H), 4.48 (s, 2H), 7.0 (m, 3H).

I. (2S,3S,5S)-2-(2,6-Dimemethylphenoxyacetyl) amino-3-hydroxy-5-(t-butyloxycarbonylamino)-6-diphenylhexane Coupling of the amine from Ex ample 1 F with the acid from Example 1H using standard EDAC coupling procedure provided the desired compound (78%). 300 MHz $^1$H NMR (CDCl$_3$) δ 1.40 (s, 9H), 1.65 (m, 3H), 2.18 (s, 6H), 2.78 (m, 2H), 2.98 (d, J=9 Hz, 2H), 3.75 (m, 2H), 3.90 (m, 1H), 4.15 (m, 1H), 4.20 (s, 2H), 4.60 (m, 1H), 7.0 (m, 3H), 7.25 (m, 1 OH). Mass spectrum: (M=H)$^+$=547.

J. 2-N-(Benzyloxycarbonyl)amino-acetaldehyde.

To a solution of 1.45 ml of DMSO in 20 ml of CH$_2$Cl$_2$ at −78° C. was added dropwise 1.34 ml of oxalyl chloride. After 15 minutes at −78° C., a solution of N-Cbz-aminoethanol in 40 ml of CH$_2$Cl$_2$ was added. After 15 minutes at −78° C. and 2 minutes at 0° C., the solution was cooled to -78° C. and triethylamine (6.14 ml) was added dropwise. The solution was stirred at −78° C. for 30 minutes and poured into 50 ml of cold 10% aq. citric acid and extracted with ether (150 ml). The combined organic layer was washed with brine and dried with anhydrous Na$_2$SO$_4$; filtered and concentrated in vacuo. Purification of the crude product by silica gel column chromatography (10% EtOAc/CH$_2$Cl$_2$) provided the desired compound (42%). 300 MHz $^1$H NMR (CDCl$_3$) δ 4.17 (d, J=6 Hz, 2H), 5.15 (s, 2H), 5.40 (br s, 1H), 7.36 (m, 5H), 9.66 (s, 1H). Mass spectrum: (M+NH$_4$)$^+$=211.

K. N-(Benzyloxycarbonylamino)-ethyl Valine Methyl Ester

To a solution of the aldehyde from Example 1J (0.829 g, 4.29 mmole) in 17 ml of methanol was added valine methyl ester hydrochloride (0.72 g, 4.29 mmole), sodium acetate (0.7 g, 8.58 mmole), and sodium cyanoborohydride (0.54 g, 8.58 mmole. The mixture was stirred at RT overnight and the solvent was evaporated in vacuo. The residue was taken up in ethyl acetate (100 ml) and washed with satd. NaHCO$_3$ (10 ml) and the aq. layer was extracted with ethyl acetate (2×50 ml). The combined organic layer was washed with brine and dried with any sodium sulfate, filtered and concentrated in vacuo. The residue was purified by silica gel column chromatography (20% EtOAc/CH$_2$Cl$_2$) to provide the desired compound (60%). 300 MHz 1H NMR (CDCl$_3$) δ 0.91 (d, J=3 Hz, 3H), 0.94 (d, J=3 Hz, 3H), 1.90 (m, 1H), 2.55 (m, 1H), 2.80 (m, 1H), 2.98 (d, J=6 Hz, 1H), 3.20 (m, 1H), 3.30 (m, 1H), 3.71 (s, 3H), 5.10 (s, 2H), 5.27 (br s, 1H), 7;.37 (m, 5H). Mass spectrum: (M+H)$^+$=309.

L. 2S-(1-imidazolidin-2-onyl)-3-methyl butanoic acid methyl ester

The Cbz-protecting of the compound in Example 1 K was removed by hydrogenolysis and the crude product was treated with one equivalent of 1,1,-carbonyldiimidazole in CH$_2$Cl$_2$ to provide the desired compound (64%), 300 MHz 1H NMR (CDCl$_3$) δ 0.95 (d, J=7.5 Hz, 3H), 0.98 (d, J=7.5 Hz, 3H), 2.15 (m, 1H), 3.47 (m, 3H), 3.71 (s, 3H), 3.73 (m, 1H), 4.23 (d, J=10.5 Hz, 1H), 4.81 (br s, 1H), Mass spectrum: (M+H)$^+$=201.

M. 2S-(1-Imidazolidin-2-onyl)-3-methyl Butanoic Acid

To a solution of the compound from Example 1 L (151 mg, 0.75 mmole) in 2.5 ml of water and 5 ml of dioxane was added at 0° C. lithium hydroxide monohydrate (2.0 eq.). The solution was stirred at 0° C. for 1.5 h and RT for 1 h. Acidification with 1 N HCl, extraction with EtOAc (100 ml +2×50 ml), dried with sodium sulfate and evaporation of the filtered solution in vacuo provided the desired compound (88%). 300 MHz 1H NMR (DMSO-d$_6$) δ 0.85 (d, J=12 Hz, 3H), 0.92 (d, J=12 Hz, 3H), 2.05 (m, 1H), 3.25 (m, 2H), 3.30 (m, 1H), 3.50 (m, 1H), 3.90 (d, J=15 Hz, 1H), 6.40 (br s, 1H), 12.60 (br s, 1H). Mass spectrum: (M+H)$^+$=187.

N. (2S,3S,5S)-2-(2,6-Dimethylphenoxyacetyl) amino-3-hydroxy-5-amino-1,6-diphenylhexane.

To 4.5 g of the compound from Example 1I was added 40 ml each of CH$_2$Cl$_2$ and trifluoroacetic acid. The solution was left at RT for 1 h. Concentration of the solution in vacuo provided the desired compound (100%). 300 MHz 1H NMR (CDCl$_3$) δ 1.48 (m, 1H), 1.62 (m, 1H), 2.05 (m, 1H), 2.24 (s, 6H), 2.50 (m, 1H), 2.80 (m, 1H), 3.0–3.10 (m, 4H), 3.90

O. (2S,3S,5S)-2-(2,6-Dimethylphenoxyacetyl) amino-3-hydroxy-5-[2S-(1-imidazolidin-2-onyl-3-methyl-butanoyl]amino-1,6-diphenylhexane Coupling of the amino compound from Example 1N with the acid from Example 1M using standard coupling procedure [1-(3-dimethylaminopropyl)-3-ethylcarbodiimide in DMF] provided the desired compound. (80%). 300 MHz 1H NMR (CDCl$_3$) δ 0.83 (d, J=6 Hz, 3H), 0.86 (d, J=6 Hz, 3H), 1.75 (m, 2H), 2.16 (m, 1H), 2.18 (s, 6H), 2.76 (m, 2H), 2.97 (d, J=7.5 Hz, 2H), 3.14 (m, 2H), 3.30 (m, 2H), 3.70 (d, J=1-Hz, 1H), 3.75 (m, 1H), 4.20 (m, 4H), 4.50 (br s, 1H), 6.70 (d, J=7.5 Hz, 1H), 7.0 (m, 3H), 7.25 (m, 1OH). Mass Spectrum: (M+H)$^+$=615.

EXAMPLE 2

(2S,3S,5S)-2-(2,6-Dimethylphenoxyacetyl) amino-3-hydroxy-5-[2S-(1-tetrahydro-pyrimid-2-onyl)-3-methylbutanoyl]amino-1,6-diphenylhexane A. 2S-(1-Tetrahydro-pyrimid-2-onyl)-3-methyl butanoic Acid Using the procedures described in Examples 1J to 1M, but replacing the N-Cbz-aminoethanol in Example 1J with N-Cbz-3-aminopropanol provided the desired compound. 300 MHz $^1$H NMR (DMSO-d$_6$) δ 0.82 (d, J=7 Hz, 3H), 0.93 (d, J=7 Hz, 3H), 1.77 (m, 2H), 2.10 (m, 1H), 3.10–3.23 (m, 4H), 4.42 (d, J=10.5 Hz, 1H), 6.37 (br s, 1H). Mass spectrum: (M+H)$^+$=201.

B. (2S,3S,5S)-2-(2,6-Dimethylphenoxyacetyl) amino-3-hydroxy-5-[2S-(1-tetrahydro-pyrimid-2-onyl)-3-methyl butanoyl]amino-1,6-diphenylhexane Coupling of the amino compound from Example 1 N with the acid from Example 2A using standard procedure (EDAC in DMF) provided the desired compound (70%). 300 MHz 1H NMR (CDCl$_3$) δ 0.80 (d, J=4.5 Hz, 3H), 0.83 (d, J=4.5 Hz, 3H), 1.50 (m, 1H), 1.65–1.72 (m, 6H), 2.20 (s, 6H), 2.68 (m, 1H), 2.82 (m, 2H), 3.0 (d, J=7.5 Hz, 1H), 3.05 (m, 4H), 3.77 (m, 1H), 4.07 (d, J=4.5 Hz, 1H), 4.20 (m, 4H), 4.50 (br s, 1H), 6.78 (br d, 1H), 7.0 (m, 3H), 7.25 (m, 1 OH). Mass spectrum: (M+H)$^+$=629.

EXAMPLE 3

(2S,3S,5S)-2-(2,6-Dimethylphenoxyacetyl)amino-3-hydroxy-5-[2S-(3-oxazolidin-2-onyl)-3-methyl-butanoyl]amino-1,6-diphenylhexane A. 2S-(3-Oxazolidin-2-onyl)-3-methyl-butanoic Acid Methyl Ester To a solution of L-valine methyl ester hydrochloride (7.6 mmole) was added a solution of ethylene oxide in ethanol (1.5 equivalent). The solution was kept at 0° C. for 0.5 h and then at RT for 18 h, at which time 0.01 equivalent of BF$_3$.Et$_2$O was added. Fresh ethylene oxide was bubbled directly into the solution for 3 to 4 minutes. After 8 h the solution was concentrated to dryness and the residue was dissolved in CH$_2$Cl$_2$ and cooled to 0° C. To this solution was added 1.2 equivalents of triethylamine and 1.0 equivalent of triphosgene. After 1 h, the solvent was removed in vacuo and the residue was washed with water (30 ml) and extracted with CH$_2$Cl$_2$ (3×50 ml), dried and concentrated. Purification of the crude product by silica gel column chromatography (5% EtOAc/CH$_2$Cl$_2$) provided the desired compound (42%, 2 steps). 300 MHz 1H NMR (CDCl$_3$) δ 0.98 (d, J=4.0 Hz, 3H), 1.0 (d, J=4.0 Hz, 3H), 2.16 (m, 1H), 3.60 (m, 2H), 3.73 (s, 3H), 4.20 (d, J=10 Hz, 1H), 4.37 (m, 2H). Mass spectrum: (M+H)$^+$=202.

B. 2S-(3-Oxazolidin-2-onyl)-3-methyl-butanoic Acid

Hydrolysis of the methyl ester from Example 3A, using the procedure described in Example 1 M provided the desired compound. 300 MHz $^1$H NMR (DMSO-d$_6$) δ 0.90 (d, J=6 Hz, 3H), 0.95 (d, J=6 Hz, 3H), 2.1 (m, 1H), 3.55 (m, 1H), 3.70 (m, 1H), 3.88 (d, J=9 Hz, 1H), 4.30 (m, 2H), 13.0 (br s, 1H). Mass spectrum: (M+NH$_4$)$^+$=205.

C. (2S,3S,5S-2-(2,6-Dimethylphenoxyacetyl)amino-3-hydroxy-5-[2s-(3-oxazolidin-2-onyl)-3-methyl-butanoyl] amino-1,6-diphenylhexane Coupling of the amine from Example 1 N with the acid from Example 3B using standard coupling procedures (EDAC in DMF) provided the desired compound. 300 MHz 1H NMR (CDCl$_3$) δ 0.83 (d, J=4.5 Hz, 3H), 0.87 (d, J=4.5 Hz, 3H), 1.75 (m, 1H), 2.10 (m, 1H), 2.20 (s, 6H), 2.65 (m, 1H), 2.85 (m, 1H), 3.0 (m, 3H), 3.30 (m, 1H), 3.60 (m, 2H), 3.77 (m, 1H), 4.20 (m, 4H), 6.25 (br d, J=6 Hz, 1H), 7.0 (m, 3H), 7.25 (m, 10H). Mass spectrum: (M+H)$^+$=616.

EXAMPLE 4

(2S,3S,5S)-2-[(3R,3aS,6aR)-Bis-tetrahydrofuranyloxy]amino-3-hydroxy-5-[2S-(3-methyl-1-imidazolidin-2-onyl)-3-methylbutanoyl]amino-1,6-diphenylhexane A. 2S-(3-Methyl-1-imidazolidin-2-onyl)-3-methyl Butanoic Acid Methyl Ester To a suspension of 45 mg (60% oil dispersion) of sodium hydride in 0.5 ml of DMF was added a solution of 150 mg of the compound from Example 1 L in 4.5 ml of DMF. After 20 minutes at RT, (1.5 equivalent, 0.07 ml) methyl iodide was added. Reaction was complete in 1 h. The reaction was quenched with satd. NH$_4$Cl solution and extracted with ether (100 ml+50 ml×2), dried and concentrated in vacuo. The crude product was purified by silica gel column chromatography (20% EtOAc/CH$_2$Cl$_2$) to provide the desired compound (61%). 300 MHz $^1$H NMR (CDCl$_3$) δ 0.95 (d, J=6 Hz, 3H), 0.97 (d, J=6 Hz, 3H, 2.15 (m, 1H), 2.80 (s, 3H), 3.32 (m, 3H), 3.60 (m, 1H), 3.70 (s, 3H), 4.25 (d, J=10.5 Hz, 1H). Mass spectrum: (M+H)$^+$=215.

B. 2S—(3-Methyl-1-imidazolidin-2-onyl)-3-Methyl Butanoic Acid

Hydrolysis of the methyl ester from Example 4A using the procedure described in Example 1M provided the desired compound. 300 MHz $^1$H NMR (DMSO-d$_6$) δ 0.85 (d, J=6 Hz, 3H), 0.92 (d, J=6 Hz, 3H), 2.05 (m, 1H), 2.65 (s, 3H), 3.25 (m, 3H), 3.42 (m, 1H), 3.90 (d, J=10 Hz,1H). Mass spectrum: (M+H)$^+$=201.

C. (3R,3aS,6aR)-Bis-tetrahydrofuranyl-(4-nitrophenyl)carbonate

To a solution of 3R-hydroxy-(3aS,6aR)-bis-tetrahydrofuran [J. Med. Chem. 37, 2506–2508 (1994)](200 mg, 1.54 mmole) in 10 ml of CH$_2$Cl$_2$ was added triethylamine (0.26 ml, 1.85 mmole), and p-nitrophenyl chloroformate (341 mg, 1.69 mmole). The solution was kept at RT for 3 days, diluted with CH$_2$Cl$_2$ (100 ml) and washed with satd. NaHCO$_3$ (15 ml). The organic layer was dried and concentrated in vacuo. Purification by silica gel column chromatography (5% EtOAc/CH$_2$Cl$_2$) provided the desired compound (42%). 300 MHz $^1$H NMR (CDCl$_3$) δ 2.0 (m, 1H), 2.20 (m, 1H), 3.18 (m, 1H), 4.0 (m, 3H), 4.17 (m, 1H), 5.27 (m, 1H), 5.80 (d, J=6 Hz), 7.40 (d, J=7.5 Hz, 2H), 8.30 (d, J=7.5 Hz, 2H). Mass spectrum: (M+NH$_4$)$^+$=313.

D. (2S,3S,5S)-2-[(3R,3aS,6aR)-Bis-tetrahydrofuranyloxy]amino-3-hydroxy-5-(t-butyloxycarbonyl)amino-1,6-diphenylhexane To a solution of the carbonate from Example 4C (100 mg, 0.34 mmole) in 3.4 ml of DMF was added the compound from Example 1F (130 mg, 0.34 mmole). The solution was kept at RT overnight and then concentrated in vacuo. Purification of the crude product by silica gel column chromatography (2% to 5% MeOH/CH$_2$Cl$_2$) provided the desired compound (93%). 300 MHz $^1$H NMR (CDCl$_3$) δ 1.40 (s, 9H), 1.64 (m, 3H), 2.76 (m, 2H), 2.87 (m, 2H), 3.66–4.0 (m, 7H), 4.53 (m, 1H), 5.06 (m, 2H), 5.68 (d, J=6 HZ, 1H), 7.10–7.28 (m, 1OH). Mass spectrum: (M+NH$_4$)$^+$=558.

E. (2S,3S,5S)-2-[(3R,3aS,6aR)-Bis-tetrahydrofuranyloxyl]amino-3-hydroxy-5-amino-1,6-diphenylhexane To a solution of the compound from Example 4D (170 mg, 0.31 mmole) in 5 ml of CH$_2$Cl$_2$ was added 5 ml of trifluoroacetic acid. After 0.25 h, the solvent was removed in vacuo. The residue was dissolved in 100 ml of EtOAc and washed with satd. NaHCO$_3$ and then brine, dried and concentrated to provide the desired compound (91%). 300 MHz $^1$H NMR (CDCl$_3$) 31.27–1.60 (m, 4H), 1.75 (m, 2H), 2.47 (m, 1H), 2.80 (m, 1H), 2.88 (m, 2H), 3.0 (m, 2H),3.80 (m, 4H), 4.0 (m, 1H), 5.10 (m, 1H), 5.30 (d, J=10.5 Hz, 1H), 5.70 (d, J=6 Hz, 1H), 7.05-7.25 (m, 1 OH). Mass spectrum: (M+H)$^+$=441.

F. (2S,3S,5S)-2-[(3R. 3aS,6aR)-Bis-tetrahydrofuranyloxy]amino-3-hydroxy-5-[2S-(3-methyl-1-imidazolidin-2-onyl)-3-methylbutanoyl]amino-1,6-diphenylhexane Coupling of the carboxylic acid from Example 4B with the amino compound from Example 4E using standard procedure (EDAC in DMF) provided the desired compound. 300 MHz 1H NMR (CDCl$_3$) δ 0.82 (d, J=3H, 3H), 0.85 (d, J=Hz, 3H), 1.65 (m, 1H), 2.77 (s, 3H), 2.85 (m, 3H), 3.17 (m, 2H) 3.47 (m, 1H), 3.60 (m, 2H), 3.75 (m, 1H), 3.87 (m, 1H), 4.0 (m, 1H), 4.20 (m, 1H), 5.05 (m, 2H), 5.68 (d, J=6 Hz, 1H), 6.45 (br d, J=7.5 Hz, 1H), 7.20 (m, 1 OH). Mass spectrum: (M+H)$^+$=623.

EXAMPLE 5

(2S,3S,5S)-2-[(3R,3aS,6aR)-Bis-tetrahydrofuranyloxyl]amino-3-hydroxy-5-[2S-(1-imidazolidin-2-onyl)-3-methylbutanoyl]amino-1,6-diphenylhexane Coupling of the amino compound from Example 4E with the carboxylic acid from Example 1 M using standard procedure (EDAC/DMF) provided the desired compound. 300 MHz 1H NMR (CDCl$_3$) δ 0.85 (d, J=7 Hz, 3H), 0.88 (d, J=Hz, 3H), 1.70 (m, 2H, 2.18 (m, 1H), 2.80 (m, 3H), 2.95 (m, 1H), 3.20 (m, 4H), 3.60 (m, 3H), 3.75 (m, 2H), 4.0 (m, 1H), 4.20 (m, 1H), 4.45 (s, 1H), 5.10 (m, 2H), 5.67 (d, J=6 Hz, 1H) 6.60 (d, J=7.5 Hz, 1H), 7.20 (m, 1 OH). Mass spectrum: (M+H)$^+$=609.

EXAMPLE 6

(2S,3S,5S)-2-(N-((5-Thiazolyl)methoxycarbonyl)amino)-5-((2S-(1-imidazolidin-2-onyl)-3-methylbutanoyl)-amino)-3-hydroxy-1,6-diphenylhexane

A. Ethyl 2-Chloro-2-formylacetate.

To a three neck 2 L round bottom flask charged with potassium t-butoxide (0.5 mol, 500 mL of a 1 M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over NaSO$_4$, and concentrated in vacuo. The crude desired compound was stored at −30° C. and used without further purification.

B. Ethyl Thiazole-5-carboxylate

To a round bottom flask was added 250 mL of dry acetone, 7.5 g (0.123 mol) of thioformamide, and 18.54 g (0.123 mol) of ethyl 2-chloro-2-formylacetate. The reaction was heated at reflux for 2 hours. The solvent was removed in vacuo, and the residue was purified by chromatography (SiO$_2$, 6 cm o.d. column, 100% CHCl$_3$, Rf=0.25) to provide 11.6 g (60%) of the desired compound as a light yellow oil. NMR (CDCl$_3$ δ 1.39 (t, J=7 Hz, 3H), 4.38 (q, J=7 Hz, 2H), 8.50 (s, 1H), 8.95 (s, 1H).

C. 5-(Hydroxymethylthiazole

To a precooled (ice bath) three neck 500 mL flask containing lithium aluminum hydride (2.89 g, 76 mmol) in 250 mL of THF was added ethyl thiazole-5-carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the filtrate set aside. The crude salts were heated at reflux in 100 mL of ethyl acetate for 30 minutes. The resulting mixture was filtered, and the two filtrates were combined, dried over Na$_2$SO$_4$, and concentrated in vacuo. The product was purified by silica gel chromatography eluting sequentially with 0%–2%–4% methanol in chloroform, to provide the desired compound, Rf—0.3 (4% methanol in chloroform), which solidified upon standing in 75% yield. NMR (CDCl$_3$) δ 4.92 (s, 2H), 7.78 (s, 1H), 8.77 (s, 1H). Mass spectrum: (M+H)$^+$=116.

D. ((5-Thiazolyl)methyl)-(4-nitrophenyl)carbonate

A solution of 3.11 g (27 mmol) of 5-(hydroxymethyl)thiazole and excess N-methyl morpholine in 100 ml of methylene chloride was cooled to 0° C. and treated with 8.2 g (41 mmol) of 4-nitrophenyl chloroformate. After being stirred for 1 h, the reaction mixture was diluted with CHCl$_3$, washed successively with 1 N HCl, saturated aqueous NaHCO$_3$, and saturated brine, dried over NaSO$_4$, and concentrated in vacuo. The residue was purified by silica gel chromatography (SiO$_2$, 1–2% MeOH/CHCl$_3$, Rf=0.5 in 4% MeOH/CHCl$_3$) to yield 5.9 g (78%) of the desired compound as a yellow solid. NMR (CDCl$_3$) 5 5.53 (s, 2H), 7.39 (dt, J=9, 3 Hz, 2H), 8.01 (s, 1H), 8.29 (dt, J=9, 3 Hz, 2H), 8.90 (s, 1H). Mass spectrum: (M+H)$^+$=281.

E. (2S,3S,5S)-5-Amino-2-(N-((5-thiazolyl)-methoxycarbonyl)amino)-3-hydroxy-1,6-diphenylhexane Coupling of the amino compound from Example 1F with the carbonate from Example 6D using the procedure from Example 4D, followed by removal of the Boc-protecting group using TFA/CH$_2$Cl$_2$ provided the desired compound. 300 MHz $^1$H NMR (CDCl$_3$) 31.3–1.6 (m, 2H), 2.40 (dd, J=14,8 Hz, 1H), 2.78 (dd, J=5 Hz, 1H), 2.88 (d, J=7 Hz, 2H), 3.01 (m, 1H), 3.72 (br q, 1H), 3.81 (br d, J=10 Hz, 1H), 5.28 (s, 2H), 5.34 (br d, J=9 Hz, 1H), 7.07 (br d, J=7 Hz, 2H), 7.15–7.35 (m, 8H), 7.87 (s, 1H), 8.80 (s, 1H). Mass spectrum: (M+H)$^+$=426.

F. (2S,3S,5S)-2-(N-((5-thiazolyl)methoxycarbonyl)amino)-5-((2S-(1-imidazolidin-2-onyl)-3-methyl-butanoyl)-amino)-3-hydroxy-1,6-diphenylhexane Coupling of the amino compound from Example 6E with the carboxylic acid from Example 1 M using standard procedure (EDAC in DMF) provided the desired compound (52%). 300 MHz 1H NMR (CDCl$_3$) δ 0.82 (d, J=7.5 Hz, 3H), 0.85 (d, J=7.5 Hz, 3H), 1.65 (m, 2H), 2.15 (m, 1H), 2.70 (m, 3H), 2.85 (d, 7.5 Hz, 2H), 3.08 (m, 1H), 3.18 (m, 1H), 3.30 (M, 2H), 3.60 (m, 3H), 3.80 (m, 1H), 4.16 (m, 1H), 4.40 (s, 1H), 5.16 (d, J=9 Hz, 1H), 5.24 (s, 2H), 6.60 (d, J=9 Hz, 1H), 7.20 (m, 1 OH), 7.83 (s, 1H), 8.80 (s, 1H). Mass spectrum: (M+H)$^+$=594.

EXAMPLE 7

(2S,3S,5S)-2-(N-((5-Thiazolyl)-methoxycarbonyl)amino)-3-hydroxy-5-(2S-(1-imidazolidin-2-onyl)-3,3-dimethyl butanoyl)amino-1,6-diphenylhexane A. 2S-(1-Imidazolidin-2-onyl)-3,3-dimethylbutanoic Acid Using the procedures described in Example 1J to 1M, but replacing L-valine methyl ester with L-t-butyl-leucine methyl ester provided the desired compound. 300 MHz 1H NMR (DMSO-d$_6$) δ 1.0 (s, 9H), 3.22 (t, J=7.5 Hz, 2H), 3.55 (q, J=7.5 Hz, 1H), 3.65 (q, J=7.5 Hz, 1H), 4.14 (s, 1H), 6.40 (s, 1H), 12.62 (br s, 1H). Mass spectrum: (M+H)$^+$=201.

B. (2S,3S,5S)-2-(N-((5-Thiazolyl)-methoxycarbonyl)amino)-3-hydroxy-5-(2S-(1-imidazolidin-2-onyl)-3,3-dimethyl butanoyl)amino-1,6-diphenylhexane.

Coupling of the amino compound from Example 6E with the carboxylic acid from Example 7A using standard procedure (EDAC in DMF) provided the desired compound (77%). 300 MHz 1H NMR (CDCl$_3$) δ 1.0 (s, 9H), 1.68 (m, 2H), 2.60–2.80 (m, 3H), 2.85 (d, J=7.5 Hz, 1H), 3.10 (m, 1H), 3.30 (m, 1H), 3.50 (m, 1H), 4.56 (s, 1H), 5.15 (d, J=7.5 Hz, 1H), 5.25 (ABq, 1H), 6.50 (d, J=7 Hz, 1H), 7.20 (m, 1OH), 7.83 (s, 1H), 8.80 (s, 1H). Mass spectrum: (M+H)$^+$= 609.

EXAMPLE 8

(2S,3S,5S)-2-(2,6-Dimethylphenoxyacetyl)amino-3-hydroxy-5-(2S-(1-imidazolidin-2-onyl)-3,3-dimethyl butanoyl)amino-1,6-diphenylhexane Coupling of the amino compound from Example 1N with the carboxylic acid from Example 7A using standard procedure (EDAC in DMF) provided the desired compound (80%). 300 MHz $^1$H NMR (CDCl$_3$) δ 1.0 (s, 9H), 2.18 (s, 6H), 2.68 (m, 1H), 2.80 (m, 1H), 2.98 (m, 3H), 3.10 (m, 1H), 3.27 (q, J=7 Hz, 1H), 3.53 (m, 1H), 3.77 (m, 1H), 4.0 (s, 1H), 4.20 (m, 4H), 6.72 (m, 1H), 7.0 (m, 3H), 7.10–7.25 (m, 1OH). Mass spectrum: (M+H)$^+$=629.

EXAMPLE 9

(2S,3S,5S)-2-(2,6-Dimethylphenoxyacetyl)amino-3-hydroxy-5-(2S-(1-imidazolidin-2-thionyl)-3-methyl butanoyl)amino-1,6-diphenylhexane A. 2S-(1-Imidazolidin-2-thionyl)-3-methyl Butanoic Acid Using the same procedures described in Example 1J to IM, but replacing 1,1-carbonyl-diimidazole with 1,1,-thiocarbonyldiimidazole provided the desired compound. 300 MHz 1H NMR (DMSO-d$_6$) δ 0.87 (d, J=6 Hz, 3H), 0.96 (d, J=6 Hz, 3H), 2.11 (m, 1H), 3.45 (m, 2H), 3.62 (m, 1H), 3.80 (q, J=9 Hz, 1H), 4.80 (d, J=10 Hz, 1H), 8.30 (s, 1H), 12.75 (br s, 1H).

B. (2S,3S,5S)-2-(2,6-Dimethylphenoxyacetyl)amino-3-hydroxy-5-(2S-(1-imidazolidin-2-thionyl)-3-methylbutanoyl)amino-1,6-diphenylhexane Coupling of the amino compound from Example 1 N with the carboxylic acid from Example 9A using standard procedure (EDAC in DMF) provided the. desired compound (53%). 300 MHz 1H NMR (CDCl$_3$) δ 0.82 (d, J=6 Hz, 3H), 0.93 (d, J=6 Hz, 3H), 1.75 (m, 1H), 2.20 (s, 6H), 2.65 (m, 1H), 2.84 (m, 1H), 3.0 (m, 3H), 3.25 (m, 1H), 3.40 (m, 2H), 3.54 (d, J=Hz, 1H), 3.78 (m, 1H), 4.22 (m, 4H), 4.56 (d, J=10.5 Hz, 1H), 5.65 (s, 1H), 6.60 (d, J=Hz, 1H), 7.0 (m, 3H), 7.25 (m, 1OH). Mass spectrum: (M+H)$^+$=631.

EXAMPLE 10

(2S,3S,5S)-2-(4-Amino-2,6-dimethylphenoxyacetyl)amino-3-hydroxy-5-(2S-(1-imidazolidin-2-onyl)-3-methyl-butanoyl)amino-1,6-diphenylhexane A. 2,6-Dimethyl-4-nitro Phenoxyacetic Acid Ethyl Ester To a solution of 10.5 g (54.6 mmole) of ethyl 2,6-dimethylphenoxy acetate and 7.5 g (109 mmole) of sodium nitrite in 100 ml of methylene chloride was added 50 ml of trifluoroacetic acid slowly. The reaction mixture became solid after addition. Additional 35 ml of trifluoroacetic acid was added. After the reaction mixture was stirred at room temperature for 3 h, it was carefully partitioned between saturated sodium bicarbonate solution and methylene chloride. The combined organic extracts were washed with brine and dried over anhydrous sodium sulfate, filtered and evaporated to dryness under reduced pressure. The residue was recrystalized in 30% ethyl acetate and hexanes to give 4.75 g (36%) of ethyl 2,6-dimethyl-4-nitro phenoxyacetate as light yellow prisms. 300 MHz 1H NMR (CDCl$_3$) δ 1.34 (3H, t, J=7.5 Hz), 2.39 (6H, s), 4.31 (2H, q, J=7.5 Hz), 7.93 (2H, s).

B. 2,6-Dimethyl-4-nitro-phenoxyacetic Acid

To a solution of 0.962 g (4.06 mmole) of ethyl 2,6-dimethyl-4-nitro phenoxy acetate in 10 ml of methanol was added 1 ml of 3 N sodium hydroxide. After the reaction mixture was stirred at room temperature for 30 minutes it was acidified with 3 N HCl and partitioned between water and methylene chloride. The combined organic extracts were washed with brine and dried over anhydrous sodium sulfate, filtered and evaporated to dryness under reecduced pressure to give 0.82 g (97%) of 2,6-dimethyl-4-nitro phenoxy acetic acid as light yellow solid. 300 MHz 1H NMR (d$_3$-DMSO) δ 2.35 (6H, s), 4.55 (2H, s) 7.97 (2H, s), 13.02 (1H, bs).

C. (2S,3S,5S)-2-(t-Butyloxycarbonyl) amino-3-hydroxy-5-(2S-(1-imidazolidin-2-only)-3-methyl-butanoyl)amino-1,6-diphenylhexane Coupling of (2S,3S,5S)-2-(t-butyloxycarbonyl)amino-3-hydroxy-5-amino-1,6-diphenylhexane with the carboxylic acid from Example 1 M using standard procedure (EDAC in DMF) provided the desired compound (100%). 300 MHz $^1$H NMR (CDCl$_3$) δ 0.83 (d, J=6 Hz, 3H), 0.87 (d, J=6 Hz, 3H), 1.40 (s, 9H), 1.70 (m, 2H), 2.16 (m, 1H), 2.58–2.80 (m, 4H), 3.10–3.30 (m, 4H), 3.65 (m, 2H), 4.20 (m, 1H), 4.38 (s, 1H), 4,83 (d, J=Hz, 1H), 6.53 (d, J=9 Hz, 1H), 7.20 (m, 1OH). Mass spectrum: (M+H)$^+$=553.

D. (2S,3S,5S)-2-Amino-3-hydroxy-5-(2S-(1-imidazolidin-2-onyl)-3-methyl-butanoyl)amino-1,6-diphenylhexane Deprotection of the Boc-protecting group of the compound from Example 1° C. by standard procedure (TFA/CH$_2$Cl$_2$) provided the desired compound. 300 MHz 1H NMR (CDCl$_3$) δ 0.87 (d, J=6 Hz, 3H), 0.90 (d, J=6 Hz, 3H), 1.33 (dd, J=4.5, 9.0 Hz, 1H) 2.18 (m, 1H), 2.50 (m, 1H), 2.80 (m, 5H), 3.20 (m, 4H) 3.72 (d, J=10 Hz, 1H), 4.30 (m, 1H), 4.50 (s, 1H), 6.67 (d, J=7 Hz, 1H), 7.20 (m, 1 OH). Mass spectrum: (M+H)$^+$=453.

E. (2S,3S,5S)-2-(4-Nitro-2,6-dimethylphenoxyacetyl) amino-3-hydroxy-5-(2S-(1-imidazolidin-2-onyl)-3-methyl-butanoyl) amino-1,6-diphenylhexane Coupling of the amino compound from Example 1D with the carboxylic acid from Example 10B using standard procedure (EDAC in DMF) provided the desired compound. 300 MHz 1H NMR (CDCl$_3$) δ 0.83 (d, 7 =Hz, 3H), 0.86 (d, J=7 Hz, 3H), 1.70 (m, 3H), 2.18 (m, 2H), 2.28 (s, 6H) 2.75 (m, 3H), 2.95–3.30 (m, 6H), 3.67 (d, J=10.5 Hz, 1H), 3.75 (m, 1H), 3.82 (d, J=4 Hz, 1H), 4.25 (m, 5H), 6.55 (d, J=7 Hz, 1H), 7.20 (m, 1OH), 7.92 (s, 2H). Mass spectrum: (M+H)$^+$= 660.

F. (2S,3S,5S)-2-(4-Amino-2,6-dimethylphenoxyacetyl)amino-3-hydroxy-5-(2S-(1-imidazolidin-2-onyl)-3-methyl-butanoyl)amino-1,6-diphenylhexane To a suspension of 7 mg of 10% Pd/C in 5 ml of methanol was added a solution of 69 mg of the compound from Example 10E. The reaction mixture was stirred vigorously under a hydrogen atmosphere (balloon filled with hydrogen attached to a 3-way stopcock). After 1 h, reaction was complete by TLC analysis; the catalyst was filtered off and the filtrate was concentrated in vacuo. The crude product was purified by silica gel column chromatography (2% to 5% MeOH/CH$_2$Cl$_2$) to provide the desired compound (65%). 300 MHz 1H NMR (CDCl$_3$) δ 0.82 (d, J=Hz, 3H), 0.87 (d, J=6 Hz, 3H), 1.70 (m, 2H), 2.10 (s, 6H), 2.15 (m, 2H), 2.72 (m, 2H), 2.97 (d, J=7.5 Hz, 2H), 3.08 (m, 1H), 3.15 (m, 1H), 3.30 (m, 2H), 3.45 (br s, 2H), 3.66 (d, J=10 Hz, 1H), 3.72 (m, 1H), 3.90 (d, J=3 Hz, 1H), 4.10–4.20 (m, 4H), 4.30 (s, 1H), 6.33 (s, 2H), 6.57 (d, J=9 Hz, 1H), 7.20 (m, 1 OH). Mass spectrum: (M+H)$^+$=630.

EXAMPLE 11

(2S,3S,5S)-2-(2,4,6-Trimethylphenoxyacetyl) amino-3-hydroxy-5-(2S-(1-imidazolidin-2-onyl)-3-methylbutanoyl)amino-1,6-diphenylhexane

A. 2,4,6-Trimethylphenoxyacetic Acid

Using the procedures from Example 1 G and 1H, but replacing 2,6-dimethylphenol with 2,4,6-trimethylphenol provided the desired compound. 300 MHz $^1$H NMR (CDCl$_3$) δ 2.25 (s, 9H), 4.43 (s, 2H), 6.84 (s, 2H). Mass spectrum: (M+H)$^+$=195.

B. (2S,3S,5S)-2-(2,4,6-Trimethylphenoxyacetyl) amino-3-hydroxy-5-(2S-(1-imidazolidin-2-onyl)-3-methylbutanoyl) amino-1,6-diphenylhexane Coupling of the amino compound from Example 10D with the carboxylic acid from Example 1 1A using standard procedure (EDAC in DMF) provided the desired compound (51%). 300 MHz 1H NMR (CDCl$_3$) δ 0.82 (d, J=6 Hz, 3H), 0.85 (d, J=6 Hz, 3H), 1.70 (m, 4H), 2.13 (s, 6H), 2.25 (s, 3H), 2.75 (m, 2H), 2.97 (d, J=7 Hz, 1H), 3.13 (m, 2H), 3.28 (m, 2H), 3.68 (d, J=10 Hz, 1H), 3.72 (m, 1H), 4.16 (m, 4H), 4.40 (br s, 1H), 6.67 (d, J=8 Hz, 1H), 6.80 (s, 2H), 7.20 (m, 1OH). Mass spectrum: (M+H)$^+$=629.

EXAMPLE 12

(2S,3S,5S)-2-(4-Fluoro-2,6-dimethylphenoxyacetyl) amino-3-hydroxy-5-(2S-(1-imidazolidin-2-onyl)-3-methyl-butanoyl)amino-1,6-diphenylhexane

A. 4-Fluoro-2,6-dimethylphenoxyacetic Acid

Using the procedure from Example 1 G and 1H, but replacing 2,6-dimethylphenol with 4-fluoro-2,6-dimethylphenol provided the desired compound. 300 MHz 1H NMR (CD$_3$OD) δ 2.26 (s, 6H), 4.37 (s, 2H), 6.73 (d, J=9 Hz, 2H). Mass spectrum: M+=198.

B. (2S,3S,5S)-2-(4-Fluoro-2,6-dimethylphenoxyacetyl) amino-3-hydroxy-5-(2S-(1-imidazolidin-2-onyl)-3-methyl-butanoyl) amino-1,6-diphenylhexane Coupling of the amino compound from Example 1OD with the carboxylic acid from Example 1 2A provided the desired compound. 300 MHz 1H NMR (CDCl$_3$) δ 0.83 (d, J=6 Hz, 3H), 0.86 (d, J=6 Hz, 3H), 1.72 (m, 2H), 2.15 (s, 6H), 2.20 (m, 1H), 2.76 (m, 2H), 2.98 (d, J=7 Hz, 2H), 3.12 (m, 2H), 3.30 (m, 2H), 3.67 (d, J=10 Hz, 1H), 3.72 (m, 1H), 4.13 (AB q, J=8, 9 Hz, 2H), 4.20 (m, 2H), 4.37 (s, 1H), 6.64 (d, J=9 Hz, 1H), 6.70 (d, J=Hz, 2H), 7.20 (m, 1 OH). Mass spectrum: (M+H)$^+$=633.

EXAMPLE 13

(2S,3S,5S)-2-(4.6-Dimethyl pyrimidin-5-oxy-acetyl) amino-3-hydroxy-5-(2S-(1-imidazolidin-2-onyl)-3-methyl-butanoyl)amino-1,6-diphenylhexane

A. 4.6-Dimethylpyrimidin-5-oxy-acetic Acid

Using the procedures from Example 1G and 1H, but replacing 2,6-dimethylphenol with 5-hydroxy-4,6- dimethylpyrimidine (prepared according to Chem. Ber. 93 pg. 1998, 1960) provided the desired compound. 300 MHz $^1$H NMR (DMSO-d$_6$) δ 2.45 (s, 6H), 4.55 (s, 2H), 8.50 (s, 1H). Mass spectrum: (M+H)$^+$=183.

B. (2S,3S,5S)-2-(4,6-Dimethylpyrimidin-5-oxy-acetyl) amino-3-hydroxy-5-(2S-(1-imidazolidin-2-onyl)-3-methyl-butanoyl)amino-1,6-diphenylhexane Coupling of the amino compound from Example 10D with the carboxylic acid from Example 13A provided the desired compound. 300 MHz $^1$H NMR (CDCl$_3$) δ 0.82 (d, J=6 Hz, 3H), 0.85 (d, J=6 Hz, 3H), 1.70 (m, 2H), 2.15 (m, 1H), 2.40 (s, 6H), 2.75 (m, 2H), 2.97 (d, J=7 Hz, 2H), 3.12 (m, 2H), 3.30 (m, 2H), 3.66 (d, J=10 Hz, 1H), 3.74 (m, 1H), 3.88 (d, J=Hz, 1H), 4.20 (m, 4H, 6.62 (d, J=9 Hz, 1H), 7.0 (d, J=9 Hz, 1H), 7.20 (m, 10H), 8.70 (s, 1H). Mass spectrum: (M+H)$^+$=617.

EXAMPLE 14

D. (2S,3S,5S)-2-(2,4-Dimethyl-pyridin-3-oxy-acetyl) amino-3-hydroxy-5-(2S-(1-imidazolidin-2-onyl)-3,3-dimethyl butanoyl) amino-1,6-diphenylhexane.

A. 2,4-Dimethyl-pyridin-3-oxy-acetic Acid

Using the procedures from Example 1 G and 1H, but replacing 2,6-dimethylphenol with 2,4 dimethyl-3-hydroxypyridine (prepared according to J. Med. Chem. 35, pg. 3667–3671, 1992) provided the desired compound. 300 MHz 1H NMR (DMSO-d$_6$) δ 2.26 (s, 3H), 2.42 (s, 3H), 4.44 (s, 2H), 7.08 (d, J=5 Hz, 1H), 8.07 (d, J=5 Hz, 1H). Mass spectrum: (M+H)$^+$=182.

B. (2S,3S,5S)-2-(2,4-Dimethyl-pyridin-3-oxy-acetyl)amino-3-hydroxy-5-(t-butyloxycarbonyl) amino-1,6-diphenylhexane Coupling of the amino compound from Example 1F with the carboxylic acid from Example 14A using standard procedure (EDAC in DMF) provided the desired compound. 300 MHz 1H NMR (CDCl$_3$) δ 1.40 (s, 9H), 1.70 (m, 2H), 2.18 (s, 3H), 2.40 (s, 3H), 2.77 (m, 2H), 2.98 (d, J=7 Hz, 2H), 3.75–3.95 (m, 3H), 4.20 (s, 2H), 4.22 (m, 1H), 4.60 (br d, 1H), 7.0 (d, J=5H, 1H), 7.10 (m, 3H), 7.25 (m, 7H), 8.16 (d, J=5 Hz, 1H). Mass spectrum: (M+H)$^+$=548.

C. (2S,3S,5S)-2-(2,4-Dimethyl-pyridin-3-oxy-acetyl) amino-3-hydroxy-5-amino-1,6-diphenylhexane Deprotection of the Boc-group in the compound from Example 14B using standard procedure (TFA/CH$_2$Cl$_2$) provided the desired compound. 300 MHz 1H NMR (CDCl$_3$) S 1.45 (m, 1H), 1.62 (m, 1H), 2.23 (s, 3H), 2.45 (s, 3H), 2.50 (m, 1H), 2.80 (m, 1H), 3.0 (m, 2H), 3.12 (m, 1H), 3.90 (m, 1H), 4.18 (m, 1H), 4.25 (ABq, J=9, 12 Hz, 2H), 6.98 (d, J=5 Hz, 1H), 7.10 (m, 2H), 7.30 (m, 8H), 8.17 (d, J=5 Hz, 1H). Mass spectrum: (M+H)$^+$=448.

D. (2S,3S,5S)-2-(2,4-Dimethyl-pyridin-3-oxy-acetyl)amino-3-hydroxy-5-(2S-(1-imidazolidin-2-onyl)-3,3-dimethylbutanoyl)amino-1,6-diphenylhexane Coupling of the amino compound from Example 14C with the carboxylic acid from Example 7A using standard procedure (EDAC in DMF) provided the desired compound. 300 MHz $^1$H NMR (CDCl$_3$) 61.0 (s, 9H), 1.70 (m, 3H), 2.18 (s, 3H), 2.42 (s, 3H), 2.75 (m, 2H), 3.0 (m, 4H), 3.30 (m, 1H), 3.55 (m, 1H), 3.80 (m, 1H), 4.05 (s, 1H), 4.20 (m, 4H), 4.60 (s, 1H), 6.70 (d, J=7 Hz, 1H), 6.97 (d, J=5 Hz, 1H), 7.15 (m, 3H), 7.25 (m, 7H), 8.17 (d, J=Hz, 1H), Mass spectrum: (M+H)$^+$=630.

EXAMPLE 15

(2S,3S,5S)-2-(2,4-Dimethyl-pyridin-3-oxy-acetyl) amino-3-hydroxy-5-(2S-(1-imidazolidin-2-onyl)-3-methyl-butanoyl)amino-1,6-diphenylhexane Coupling of the amino compound from Example 14C with the carboxylic acid from Example 1 M using standard procedure (EDAC in DMF) provided the desired compound. 300 MHz 1H NMR (CDCl$_3$) δ 0.82 (d, J=6 Hz, 3H), 0.86 (d, J=6 Hz, 3H), 1.75 (m, 3H), 2.15 (m, 1H), 2.18 (s, 3H), 2.40 (s, 3H), 2.75 (m, 2H), 2.97 (d, J=7.5 Hz, 2H), 3.20 (m, 4H), 3.70 (d, J=10 Hz, 1H), 3.75 (m, 1H), 4.20 (m, 6H), 4.52 (s, 1H), 3.75 (m, 1H), 4.20 (m, 6H), 4.52 (s, 1H), 6.80 (d, J=7 Hz, 1H), 6.96 (d, J=4.5 Hz, 1H), 7.20 (m, 10H), 8.17 (d, J=4.5 Hz, 1H). Mass spectrum: (M+H)$^+$=616.

EXAMPLE 16

(2S,3S,5S)-2-(2,6-Dimethylthiophenoxyacetyl) amino-3-hydroxy-5(2S-(1-imidazolidin-2-onyl)-3-methyl-butanoyl)amino-1,6-diphenylhexane A. 2,6-Dimethylthiophenoxy Acetic Acid Using the procedures from Example 1 G and 1H, but replacing 2,6-dimethylphenol with 2,6-dimethylthiophenol provided the desired compound. 300 MHz $^1$H NMR (CDCl$_3$) 62.56 (s, 6H), 3.40 (s, 2H), 7.10 (m, 3H). Mass spectrum: (M+H)$^+$=197.

B. (2S,3S,5S)-2-(2,6-Dimethylthiophenoxyacetyl) amino-3-hydroxy-5-(2S-(1-imidazolidin-2-onyl)-3-methyl-butanoyl) amino-1,6-diphenylhexane Coupling of the carboxylic acid from Example 16A with the amino compound from Example 10D provided the desired compound. 300 MHz 1H NMR (CDCl$_3$) δ 0.82 (d, J=6 Hz, 3H), 0.86 (d, J=6 Hz, 3H), 2.15 (m, 1H), 2.52 (s, 6H), 2.70 (m, 4H), 3.10 (m, 2H), 3.30 (m, 4H), 3.60 (m, 2H), 4.0 (m, 1H), 4.10 (m, 1H), 4.22 (s, 1H), 6.39 (d, J=7 Hz, 1H), 6.58 (d, J=9 Hz, 1H), 7.20 (m, 13H). Mass spectrum: (M+H)$^+$=631.

EXAMPLE 17

(2S,3S,5S)-2-(2,6-Dimethylphenoxyacetyl)amino-3-hydroxy-5-(2S-(1-pyrrolidin-2-onyl)-3-methyl-butanoyl)amino-1,6-diphenylhexane A. 4-Bromobutanoyl-L-valine Methyl Ester To a solution of 1.08 g (8.4 mmole) of L-valine methyl ester in 30 ml of CH$_2$Cl$_2$ was added 1.36 ml (16.8 mmole) of pyridine, cooled to 0° C. and 1.55 9 (8.4 mmole) of 4-bromobutanoyl chloride added. The solution was stirred at 0° C. for 40 minutes and at RT for 1 h. The solution was washed with satd. NaHCO$_3$, brine and dried with anhy. Na$_2$SO$_4$; filtered and concentrated in vacuo. The crude product was purified by silica gel column chromatography (5% EtOAc/CH$_2$Cl$_2$) to provide 1.82 g (77%) of desired product. 300 MHz 1H NMR (CDCl$_3$) δ 0.92 (d, J=6 Hz, 3H), 0.96 (d, J=6 Hz, 3H) 2.20 (m, 3H), 2.46 (m, 2H), 3.50 (m, 2H), 3.76 (s, 3H), 4.58 (dd, J=4,7 Hz, 1H), 5.97 (br d, J=7 Hz, 1H). Mass spectrum: (M+H)$^+$=297.

B. 2S-(1-Pyrrolidin-2-onyl)-3-methyl-butanoic Acid

To a solution of 1.49 g (5.3 mmole) of the compound from Example 17A in a mixture of DMF/CH$_2$Cl$_2$ cooled to 0° C. was added 0.234 g (1.1 equivalent) of 60% sodium hydride in mineral oil. The mixture was slowly warmed up to RT and stirred overnight. The mixture was poured into satd. ammonium chloride and extracted with ethyl acetate, dried and concentrated in vacuo. The crude product was hydrolyzed using lithuim hydroxide as in Example 1H to provide the desired compound. 300 MHz 1H NMR (CDCl$_3$) δ 0.96 (d, J=7 Hz, 3H), 1.06 (d, J=7 Hz, 3H), 2.10 (m, 2H), 2.40 (m, 1H), 2.50 (t, J=7 Hz, 2H), 3.56 (m, 2H), 4.14 (d, J=10 Hz, 1H). Mass spectrum: (M+H)$^+$=186.

C. (2S,3S,5S)-2-(2,6-Dimethylphenoxyacetyl) amino-3-hydroxy-5-(2S-(1-pyrrolidin-2-onyl)-3-methyl-butanoyl)amino-1,6-diphenylhexane Coupling of the carboxylic acid from Example 17B with the amine from Example 1 N using standard procedure (EDAC in DMF) provided the desired compound. 300 MHz 1H NMR (CDCl$_3$) δ 0.77 (d, J=7 Hz, 3H), 0.83 (d, J=7 Hz, 3H), 1.75 (m, 3H), 2.10 (m, 1H), 2.20 (s, 6H), 2.25 (m, 1H), 2.65 (m, 1H), 2.85 (m, 1H), 3.0 (d, J=7 Hz, 2H), 3.20 (m, 1H), 3.77 (m, 2H), 3.88 (d, J=10 Hz, 1H), 4.20 (m, 3H), 6.30 (d, J=7 Hz, 1H), 6.98 (m, 3H), 7.20 (m, 10H). Mass spectrum: (M+H)$^+$=614.

EXAMPLE 18

(2S,3S,5S)-2-(2,6-Dimethylphenoxyacetyl) amino-3-hydroxy-5-(2S-(1-pyrrolidin-2,5-dionyl)-3-methyl-butanoyl)amino-1,6-diphenylhexane

A. 2S-(1-Pyrrolidin-2.5-dionyl)-3-methyl-butanoic Acid Benzyl Ester

To a solution of 700 mg (3.38 mmole) of L-valine benzyl ester in 6 ml of chloroform was added 1 equivalent of succinic anhydride. After 1 h at RT, the solvent was removed in vacuo and the residue was dissolved in 20 ml of DMF. To this solution was added 0.52 g of N-hydroxy-benzotriazole, 0.68 g of EDAC and 0.52 ml of triethylamine. After 24 h at RT, 20 mg of 4-dimethylaminopyridine was added. The solution was left at RT for 3 days. After standard work-up, the crude product was purified by silica gel column chromatography to provide 0.25 g of desired product (26%). 300 MHz 1H NMR (CDCl$_3$) δ 0.84 (d, J=7 Hz, 3H), 1.12 (d, J=7 Hz, 3H), 2.70 (m, 1H), 2.71 (s, 4H), 4.45 (d, J=9 Hz, 1H), 5.15 (s, 2H), 7.30 (m, 5H).

B. 2S-(1-Pyrrolidin-2,5-dionyl)-3-methyl-butanoic acid.

A mixture of 0.245 of the product from Example 18A, 30 mg of 10% palladium on charcoal in 50 ml of methanol was stirred vigorously under hydrogen atmosphere (balloon filled with hydrogen) for 1 h. The catalyst was filtered off and the solvent was removed under vacuum to provide 168 mg of the desired compound. 300 MHz 1H NMR (CDCl$_3$) δ 0.84 (d, J=6 Hz, 3H), 1.13 (d, J=6 Hz, 3H), 2.65 (m, 1H), 2.80 (s, 4H), 4.45 (d, J=8 Hz, 1H). Mass spectrum: (M+H)$^+$=200.

C. (2S,3S,5S)-2-(2,6-Dimethylphenoxyacetyl) amino-3-hydroxy-5-(2S-(1-pyrrolidin-2,5-dionyl)-3-methyl-butanoyl) amino-1,6-diphenylhexane.

Coupling of the carboxylic acid from Example 18B with the amine from Example 1 N using standard procedure (EDAC in DMF) provided the desired product (75%). 300 MHz 1H NMR (CDCl$_3$) δ 0.70 (d, J=4 Hz, 3H), 0.72 (d, J=4 Hz, 3H), 1.70 (m, 1H), 2.20 (s, 6H), 2.45 (m, 2H), 2.60 (s, 4H), 2.80 (m, 2H), 3.0 (m, 2H), 3.76 (m, 1H), 4.20 (m, 6H), 7.0 (m, 3H), 7.20 (m, 1 OH). Mass spectrum: (M+H)$^+$=628.

EXAMPLE 19

(2S,3S,5S)-2-(Trans-3-(2,6-dimethylphenyl) propenoyl)amino-3-hydroxy-5-(2S-1-tetrahydropyrimidin-2-onyl)-3-methyl-butanoyl) amino-1,6-diphenylhexane

A. 2,6-Dimethyl Benzaldehyde

Oxidation of 2,6-dimethyl benzyl alcohol by standard Swern oxidation procedure (oxalyl chloride/DMSO) provided the desired compound. 300 MHz 1H NMR (CDCl$_3$) δ 2.62 (s, 6H), 7.10 (m, 2H), 7.33 (t, J=7 Hz, 1H), 10.63 (s, 1H), Mass spectrum: (M+H)$^+$=135.

B. Trans-3-(2,6-dimethylphenyl)-progenoic Acid Methyl Ester

To a solution of trimethyl phosphonoacetate (149 mg, 0.82 mmole) in 15 ml of THF was added 36 mg of sodium hydride (60% in oil). After 15 minutes 100 mg of the compound from Example 19A in 2 ml of THF was added. After 2 h, the reaction was quenched carefully with water and extracted with ethyl acetate (70 ml), dried and concentrated. Purification of the crude product by silica gel column chromatography (hexane/EtOAc 95:5) provided the desired compound (75%). 300 MHz 1H NMR (CDCl$_3$) δ 2.35 (s, 6H), 3.82 (s, 3H), 6.07 (d, J=16 Hz, 1H). 7.10 (m, 3H), 7.85 (d, J=16 Hz, 1H). Mass spectrum: (M+NH$_4$)$^+$=191.

C. Trans-3-(2,6-dimethylphenyl)-propenoic Acid

Hydrolysis of the methyl ester from Example 19B using lithium hydroxide in a mixture of methanol and water provided the desired compound (84%). 300 MHz $^1$H NMR (CDCl$_3$) δ 2.38 (s, 6H), 6.13 (d, J=16 Hz,1H), 7.10 (m, 3H), 7.96 (d, J=16 Hz, 1H). Mass spectrum: (M+H)$^+$=194. D. (2S,3S,5S)-2-(Trans-3-(2,6-dimethylphenyl)propenoyl) amino-3-hydroxy-5-(t-butyloxycarbonyl)amino-1,6-diphenylhexane Coupling of the carboxylic acid from Example 19C with the amine from Example 1 F using standard procedure (EDAC/DMF) provided the desired compound (84%). 300 MHz 1H NMR (CDCl$_3$) δ 1.40 (s, 9H), 1.68 (m, 1H), 2.34. (s, 6H), 2.75 (m, 2H), 2.96 (m, 2H), 3.72 (m, 1H), 3.85 (m, 1H), 4.08 (m, 2H), 4.60 (m, 1H), 5.88 (d, J=10 Hz, 1H), 5.94 (d, J=16 Hz,1H), 7.10 (m, 5H), 7.25 (m, 8H), 7.72 (d, J=16 Hz, 1H). Mass spectrum: (M+H)$^+$=543

E. (2S,3S,5S)-2-(Trans-3-(2,6-dimethylphenyl) propenoyl)amino-3-hydroxy-5-(2S-1-tetrahydropyrimidin-2-onyl)-3-methyl-butanoyl) amino-1,6-diphenylhexane Removal of the Boc-protecting group of the compound from Example 19D (TFA/CH$_2$Cl$_2$) and coupling of the resulting amine with the carboxylic acid from Example 2A using standard procedure (EDAC/DMF) provided the desired compound (73%). 300 MHz 1H NMR (CDCl$_3$) δ 0.82 (d, J=6 Hz, 3H), 0.87 (d, J=6 Hz, 3H), 1.50 (m, 1H), 1.70 (m, 2H), 2.20 (m, 1H), 2.33 (s, 6H), 2.68 (m, 1H), 2.78 (m, 1H), 2.85 (m. 1H), 3.05 (m, 5H), 3.73 (m, 1H), 4.17 (m, 1H), 4.30 (d, J=3 Hz, 1H), 4.60 (s, 1H), 5.95 (d, J=15 Hz, 1H),6.0 (d, J=9 Hz, 1H), 6.80 (d, J=7 Hz, 1H), 7.25 (m, 13H), 7.70 (d, J=15 Hz, 1H). Mass spectrum: (M+H)$^+$=625.

EXAMPLE 20

(2S,3S,5S)-2-(3-(2,6-Dimethylphenyl)propanoyl)
amino-3-hydroxy-5-(2S-(1-tetrahydropyrimidin-2-
onyl)-3-methyl-butanoyl) amino-1,6-diphenylhexane

A. 3-(2,6-Dimethylphenyl)propanoic Acid Methyl Ester

A solution of 400 mg of the compound from Example 19B in 25 ml of methanol and 40 mg of 10% Pd/C was stirred vigorously under a hydrogen atmosphere (balloon pressure) for 3 h. The catalyst was filtered off and concentration of the filtrate in vacuo provided the desired compound (98%). 300 MHz 1H NMR (CDCl$_3$) δ 2.35 (s, 6H), 2.45 (m, 2H), 2.98 (m, 2H), 3.22 (s, 3H), 7.02 (s, 3H). Mass spectrum: (M+H)$^+$=210.

B. 3-(2,6-Dimethylphenyl)propanoic Acid

Hydrolysis of the methyl ester from Example 20A, using lithium hydroxide in methanol and water provided the desired compound (93%). 300 MHz 1H NMR (CDCl$_3$) δ 2.36 (s, 6H), 2.50 (m, 2H), 3.0 (m, 2H), 7.03 (s, 3H). Mass spectrum: (M+NH$_4$)$^+$=196.

C. (2S,3S,5S)-2-(3-2,6-Dimethylphenyl)propanoyl) amino-3-hydroxy-5-(t-butyloxycarbonyl)amino-1,6-diphenylhexane Coupling of the carboxylic acid from Example 20B with the amine from Example 1 F using standard coupling procedure (EDAC/DMF) provided the desired compound. 300 MHz 1H NMR (CDCl$_3$) δ 1.40 (s, 9H), 1.55 (m, 2H), 2.20 (m, 2H), 2.30 (s, 6H), 2.74 (m, 2H), 2.85 (m, 4H), 3.66 (m, 1H), 3.82 (m, 1H), 3.95 (m, 2H), 4.57 (br d, 1H), 5.66 (d, J=9 Hz, 1H), 7.0 (s, 3H), 7.22 (m, 1 OH). Mass spectrum: (M+H)$^+$=545.

D. (2S,3S,5S)-2-(3-(2,6-Dimethylphenyl) propanoyl) amino-3-hydroxy-5-(2S-(1-tetrahydropyrimidin-2-onyl)-3-methyl-butanoyl) amino-1,6-diphenylhexane Removal of the Boc-protecting group of the compound from Example 2° C. using trifluoroacetic acid in CH$_2$Cl$_2$ and coupling of the resulting amine with the carboxylic acid from Example 2A using standard coupling procedure (EDAC/DMF) provided the desired compound. 300 MHz 1H NMR (CDCl$_3$) δ0.82 (d, J=6 Hz, 3H), 0.86 (d, J=6 Hz, 3H), 1.55 (m, 2H), 1.65 (m, 1H), 1.70 (s, 3H), 2.20 (m, 3H), 2.30 (s, 6H), 2.65 (m, 1H), 2.75 (m, 1H), 2.86 (m, 5H), 3.10 (m, 3H), 3.68 (m, 1H), 4.10 (m, 4H), 4.63 (s, 1H), 5.75 (d, J=7 Hz, 1H), 6.76 (d, J=7 Hz, 1H), 7.0 (m, 3H), 7.20 (m, 1OH). Mass spectrum: (M+H)$^+$=627.

EXAMPLE 21

(2S,3S,5S)-2-(2,6-Dimethyl-4-hydroxy-
phenoxyacetyl)amino-3-hydroxy-5-(2S-(1-
tetrahydropyrimidin-2-onyl)-3-methyl-butanoyl)
amino-1,6-diphenylhexane

A. 2,6-Dimethyl-4-tert-butyldimethylsilyloxyphenol

To a solution of 2.5 g (14.7 mmole) of 2,6-dimethylquinone in 5 ml of methanol was added 200 mg of Pd/C (20%). The reaction mixture was stirred under 1 atmosphere of hydrogen for overnight. The Pd/C was removed over a celite pad, and the solvent was evaporated to dryness under reduced pressure to give 2.0 g (100%) of 2,6-dimethyldihydroquinone as a light yellow oil.

To a solution of 2.0 g (14.7 mmole) of 2,6-dimethyldihydroquinone in 10 ml of methylene chloride was added 1.2 g (17.6 mmole) of imidazole and 2.2 g (1 4.7 mmol) of tert-butyldimethylsilyl chloride subsequently at 0° C. After the reaction was complete as indicated by TLC, it was partitioned between methylene chloride and 1:1 mixture of 3 N hydrogen chloride and brine. The organic layer was washed with brine, dried over sodium sulfate, filtered and evaporated to dryness under reduced pressure. Silica gel chromatography using 5% ethyl acetate:hexanes gave 1.8 g (49%) of 2,6-dimethyl-4-tert-butyldimethylsilyloxy phenol as a white solid. 300 MHz $^1$H NMR (CDCl$_3$) δ 0.16 (s, 6H), 0.98 (s, 9H), 2.19 (s, 6H), 4.22 (s, 1H), 6.48 (s, 2H). Mass spectrum: (M+H)$^+$=253.

B. Ethyl 2,6-Dimethyl-4-tert-Butyldimethylsilyloxy Phenoxyl Acetate

A solution of 1.8 g (7.1 mmole) of 2,6-dimethyl-4-tert-butyldimethylsilyloxy phenol in 5 ml of dimethylformamide was treated with 2.0 g (1.43 mmole) of potassium carbonate and 830 μl (7.5 mmole) of ethyl bromoacetate. The resulting solution was heated at 70° C. for 4 hr. After cooled to room temperature, the reaction mixture was partitioned between ethyl acetate and 3 N hydrogen chloride. The combined organic layer was washed with diluted brine, dried over magnesium sulfate, filtered, and evaporated in vacuo. Silica gel chromatography using 5% ethyl acetate:hexanes gave 2.03 9 (85%) of ethyl 2,6-dimethyl-4-tert-butyldimethylsilyloxy phenoxyl acetate as a light yellow oil. 300 MHz $^1$H NMR (CDCl$_3$) δ 0.17 (s, 6H), 0.97 s, 9H), 1.33 (t, 3H, J=6.3 Hz), 2.22 (s, 6H), 4.30 (q, 2H, J=6.3 Hz), 4.35 (s, 2H), 6.57 (s, 2H). Mass spectrum: (M+H)$^+$=356.

C. 2,6-Dimethyl-4-Hydroxyl Phenoxyacetic Acid

To a solution of 2.03 g (6.0 mmole) of ethyl 2,6-dimethyl-4-tert-butyldimethysilyloxy phenoxy acetate in 10 ml of methanol was added 4 ml of 3 N sodium hydroxide. After the reaction mixture was stirred at room temperature for 30 minutes it was acidified with 3 N HCl. The reaction was allowed to stir for additional 1 h, and then partitioned between water and methylene chloride. The combined organic extracts were washed with brine and dried over anhydrous sodium sulfate, filtered, and evaporated to dryness under reduced pressure. Trituration with hexanes gave 910 mg (77%) of 2,6-dimethyl-4-hydroxyl phenoxyacetic acid as a white solid. 300 MHz 1H NMR (CD$_3$OD) δ 2.18 (s, 6H), 4.31 (s, 2H), 6.41 (s, 2H). Mass spectrum: (M+H)$^+$= 214.

D. (2S,3S,5S)-2-(2,6-Dimethyl-4-hydroxy-phenoxyacetyl)amino-3-hydroxy-5-(t-butyloxycarbonyl)amino-1,6-diphenylhexane Coupling of the carboxylic acid from Example 21C with the amine from Example 1F using standard coupling procedure (EDAC/DMF) provided the desired compound. 300 MHz 1H NMR (CDCl$_3$) δ 1.40 (s, 9H), 1.68 (m, 2H), 2.07 (s, 6H), 2.77 (d, J=6 Hz, 2H), 2.98 (m, 2H), 3.74 (m, 1H), 3.90 (m, 1H), 4.10 (m, 3H), 4.58 (m, 1H), 5.20 (m, 1H), 6.44 (s, 2H), 7.10–7.30 (m, 1OH).

E. (2S,3S,5S)-2-(2,6-Di methyl-4-hydroxy-phenoxyacetyl)amino-3-hydroxy-5-(2S-(1-tetrahydropyrimidin-2-onyl)-3-methyl-butanoyl) amino-1,6-diphenylhexane Removal of the Boc-protecting group of the compound from Example 21D using TFA/CH$_2$Cl$_2$ and coupling of the resulting amine with the carboxylic acid from Example 2A using standard procedure (EDAC/DMF) provided the desired compound. 300 MHz 1H NMR (CDCl$_3$) δ 0.78 (d, J=5 Hz, 3H), 0.81 (d, J=5 Hz, 3H), 1.47 (m, 1H), 2.03 (s, 6H), 2.18 (m, 1H), 2.62 (m, 1H), 2.80 (m, 2H), 3.05 (m, 6H), 3.78 (m, 1H), 4.12 (M, 6H), 4.37 (M, 1H), 4.71 (s, 1H), 6.47 (s, 2H), 6.94 (br d, 1H), 7.20 (m, 1 OH). Mass spectrum: (M+H)$^+$=645.

EXAMPLE 22

(2S,3S,5S)-2-(cis(+)-1,1-dioxo-2-isopropyl-3-tetrahydrothiophenoxy)amino-3-hydroxy-5-(2S-(1-tetrahydropyrimid-2-onyl)-3-methylbutanoylamino-1,6-diphenylhexane

A. Cis (+)-2-isopropyl-3-hydroxy-tetrahydrothiophene

To a solution of ethyl-3-mercaptopropionate (27.25 ml, 0.246 mole) in 200 ml of ethanol was added carefully sodium ethoxide (16.75 9, 0.246 mole) in several portions. The resulting suspension was then cooled to −20° C. and ethyl-2-bromoisovalerate (50 g, 0.239 mole) in 50 ml of ethanol was added dropwise over 2 h. After addition was complete, the reaction was warmed to ambient temperature and stirred for 3 h. The mixture was poured into 600 ml of ethyl acetate and 600 ml of saturated NH$_4$Cl. The ethyl acetate layer was removed and the aqueous layer extracted (2×200 ml) with ethyl acetate. The combined organic layer was dried over sodium sulfate, filtered and concentrated in vacuo to give an orange oil. The oil was dissolved in 500 ml of toluene and sodium ethoxide (16.75 g, 0.246 mole) was added. The reaction mixture was heated to reflux for 6 h, cooled to RT, and then poured into an ice-cold solution of 1 N HCl (235 ml) and extracted with ethyl acetate (3×150 ml). The combined organic layers were dried over sodium sulfate, filtered and concentrated to an oil that was used in the next step without purification.

The crude product was added to 500 ml of aqueous 10% sulfuric acid and the resulting mixture heated to reflux for several hours, and then cooled to RT and neutralized with 6N sodium hydroxide and extracted with ethyl acetate (3×300 ml). The combined organic layer was dried, filtered and concentrated in vacuo to give a dark burgundy oil. The crude product (ketone) was purified by vacuum distillation at 75°–80° C. 300 MHz 1H NMR (CDCl$_3$) δ 0.93 (d, J=9 Hz, 3H), 1.03 (d, J=9 Hz, 3H), 2.32 (m, 1H), 2.55–2.70 (m, 2H), 2.93 (t, J=7.5 Hz, 2H), 3.38 (d, J=4 Hz, 1H). Mass spectrum: (M+H)$^+$=145.

To a stirred solution of the above ketone in 125 ml of CH$_2$Cl$_2$ at 0° C. was added diisobutylaluminum hydride (86 ml, 1 M in THF) dropwise over 20 minutes. The reaction mixture was allowed to warm to room temperature and then was quenched by cautious addition of 1 N HCl (255 ml). The reaction mixture was extracted with ether (3×150 ml) and the combined ether solution was washed with satd. sodium bicarbonate, brine and dried over magnesium sulfate. The solution was concentrated in vacuo and the resulting oil was purified by silica gel column chromatography (10% EtOAc/hexane). 300 MHz 1H NMR (CDCl$_3$) δ 1.03 (d, J=7 Hz, 3H), 1.08 (d, J=7 Hz, 3H), 1.80 (d, J=9 Hz, 1H), 1.90 (m, 2H), 2.24 (m, 1H), 2.90–3.10 (m, 3H), 4.36 (m, 1H). Mass spectrum: (M+H)$^+$=147.

B. Cis(+)-(2-isopropyl-3-thiophenyl)-2(2-pyridyl) carbonate.

To the product from Example 22A (2.29 g, 15.7 mmole) in 40 ml of CH$_2$Cl$_2$ was added diisopropylethyl amine (4.65 ml, 26.7 mmole) and di-(2-pyridyl)carbonate (5.42 g, 25.1 mmole). After 18 h at RT, the reaction mixture was diluted with chloroform and washed sequentially with 10% citric acid, satd. sodium bicarbonate, brine and then dried over sodium sulfate; filtered and concentrated in vacuo. Purification of the crude product by silica gel column chromatography (20% EtOAc/hexane) provided the desired compound. 300 MHz 1H NMR (CDCl$_3$) δ 1.05 (d, J=7 Hz, 3H), 1.08 (d, J=7 Hz, 3H), 1.90 (m, 1H), 2.05 (m, 2H), 2.58 (dd, J=6,15 Hz, 2H), 3.10 (m, 2H), 3.28 (dd, J=3,12 Hz, 1H), 5.47 (m, 1H), 7.12 (m, 1H), 7.27 (m, 1H), 7.80 (m, 1H), 8.41 (m, 1H). Mass spectrum: (M+H)$^+$=268.

C. (2S,3S,5S)-2-(cis(+)-2-Isopropyl-3-tetrahydrothiophenoxy)amino-3-hydroxy-5-(t-butyloxycarbonyl)amino-1,6-diphenylhexane To a solution of the compound from Example 22B (500 mg, 1.87 mmole) in 5 ml of CH$_2$Cl$_2$ was added the amine from Example 1 F (791 mg, 2.06 mmole). The reaction was stirred at RT until all the compound from Example 22B was consumed. The reaction mixture was diluted with chloroform and washed with 10% citric acid, satd. sodium bicarbonate, brine and then dried with sodium sulfate; filtered and concentrated in vacuo. Purification of the crude product by silica gel column chromatography (2% MeOH/CH$_2$Cl$_2$) provided the desired compound (73%). 300 MHz 1H NMR (CDCl$_3$) δ 0.83–1.05 (m, 6H), 1.40 (s, 9H), 1.90 (m, 3H), 2.20 (m, 1H), 2.75 (m, 2H), 2.85 (m, 4H), 2.95–3.15 (m, 3H), 3.67–3.90 (m, 4H), 4.55 (m, 1H), 5.10 (m, 1H), 5.30 (m, 1H), 7.10–7.26 (m, 1OH). Mass spectrum: (M+H)$^+$=557.

D. (2S,3S,5S)-2-(cis(+)-1.1-Dioxo-2-isopropyl-3-tetrahydrothiophenoxy)amino-3-hydroxy-5-(t-butyloxycarbonyl)amino-1,6-diphenylhexane To the compound from Example 22C (523 mg, 0.91 mmole) in 10 ml of acetone and 0.5 ml of water was added Oxone (539 mg, 1.37 mmole) and sodium bicarbonate (152 mg, 1.82 mmole). The resulting solution was stirred for 2 h, at which time a white precipitate appeared. The reaction was quenched with aqueous sodium bisulfite and extracted with ethyl acetate (2×100 ml), dried with sodium sulfate, filtered and concentrated in vacuo. The crude product was purified by silica gel column chromatography (2% MeOH/CH$_2$Cl$_2$) to provide 422 mg of product. 300 MHz 1H NMR (CDCl$_3$) δ 1.20 (m, 6H), 1.40 (s, 9H), 1.60 (m, 4H), 2.10–2.32 (m, 4H), 2.67 (m, 2H), 2.75 (m, 2H), 2.85 (m, 2H), 3.15 (m, 2H), 3.70–3.90 (m, 3H), 4.56 (m, 1H), 5.30 (m. 2H), 7.10–7.30 (m, 1OH).

E. (2S,3S,5S)-2-(cis(+)-1 .1-Dioxo-2-isopropyl-3-tetrahydrothiophenoxy)amino-3-hydroxy-5-(2S-(1-tetrahydropyrimid-2-onyl)-3-methylbutanoyl)amino-1,6-diphenylhexane Removal of the Boc-protecting group of the compound from Example 22D using TFA/CH$_2$Cl$_2$ and coupling of the resulting amine with the carboxylic acid from Example 2A provided the desired compound (82%). 300 MHz 1H NMR (CDCl$_3$) δ 0.82 (m, 6H), 1.0–1.20 (m, 6H), 1.60 (, 2H), 2.07 (m, 1H), 2.25 (m, 2H), 2.65–3.20 (m, 12H), 3.70 (m, 1H), 3.90 (m, 1H), 4.10–4.20 (m, 2H), 5.07 (m, 1H), 5.37 (m, 1H), 5.87–5.98 (m, 1H), 6.95–7.05 (m, 1H), 7.20 (m, 1OH). Mass spectrum: (M+H)$^+$=671.

EXAMPLE 23

(2S,3S,5S)-2-(2,6-Dimethylphenoxyacetyl)amino-3-hydroxy-5-(2S-(1-dihydropyrimid-2,4-dionyl)-3-methyl-butanoyl)amino-1,6-diphenylhexane

A. N-(2-Ethoxyacryloyl)-N'-(1S-carbomethoxy-2-methyl-propyl)-urea

To 1.74 g (0.013 mole) of 2-ethoxy-acryloyl chloride in 18 ml of toluene was added 3.90 g (0.026 mole) of silver cyanate. The mixture was heated to reflux for 0.75 h. The mixture was allowed to cool to RT and the precipitate allowed to settle. The supernatant (9.6 ml) was withdrawn and added to 18 ml of dry DMF and 5 ml of $Et_2O$, cooled to −15° C. for 45 minutes and left in freezer overnight. The solvent was evaporated in vacuo and the residue was purified by silica gel column chromatography (2% MeOH/$CH_2Cl_2$) to provide 1.59 g of desired compound (90.2%). 300 MHz 1H NMR ($CDCl_3$) δ 0.96 (d, J=7 Hz, 3H), 1.0 (d, J=7 Hz, 3H), 1.37 (t, J=7.5 Hz, 3H), 2.25 (m, 1H), 3.74 (s, 3H), 3.97 (q, J=7.5 Hz, 2H), 4.42 (dd, J=4.5, 8.0 Hz, 1H), 5.25 (d, J=12 Hz, 1H), 7.68 (d, J=12 Hz, 1H), 8.55 (s, 1H), 9.10 (d, J=8 Hz, 1H). Mass spectrum: $(M+H)^+$=273.

B. 2S-(t-Dihydropyrimid-2,4-dionyl)-3-methyl Butanoic Acid

A solution of 174 mg (0.64 mmole) of the compound from Example 23A in 10 ml of 2N sulfuric acid was refluxed for 2 h, cooled to RT and left in freezer overnight. The mixture was concentrated and the residue was extracted with ethyl acetate (2×100 ml), dried and concentrated in vacuo to give 122 mg of desired compound. 300 MHz $^1$H NMR ($CDCl_3$) δ 1.06 (d, J=7 Hz, 3H), 1.13 (d, J=7 Hz, 3H), 2.25 (m, 1H), 5.04 (d, J=10 Hz, 1H), 5.74 (d, J=7 Hz, 1H), 7.50 (d, J=10 Hz, 1H), 8.43 (s, 1H).

C. (2S,3S,5S)-2-(2,6-Dimethylphenoxyacetyl) amino-3-hydroxy-5-(2S-(1-dihydropyrimid-2,4-dionyl)-3-methyl-butanoyl) amino-1,6-diphenylhexane Coupling of the carboxylic acid from Example 23B with the amine from Example 1 N using standard coupling procedure (EDAC in DMF) provided the desired compound. 300 MHz 1H NMR ($CDCl_3$) δ 0.81 (d, J=7 Hz, 3H), 0.92 (d, J=7 Hz, 3H), 2.18 (s, 6H), 2.23 (m, 1H), 2.63 (m, 1H), 2.85 (m, 1H), 3.0 (m, 2H), 3.78 (m, 1H), 4.20 (m, 4H), 4.58 (d, J=10 Hz, 1H), 5.68 (dd, J=1.5, 7.5 Hz, 1H), 7.0–7.25 (m, 1 3H), 7.50 (d, J=7.5 Hz, 1H), 9.50 (s, 1H). Mass spectrum: $(M+H)^+$=640.

EXAMPLE 24

Alternate Preparation of (2S,3S,5S)-2-(2,6-Dimethylphenoxyacetyl)amino-3-hydroxy-5-[2S-(1-tetrahydro-pyrimid-2-onyl)-3-methyl butanoyl] amino-1,6-diphenylhexane

A. 2,6-Dimethylphenoxyacetic Acid 2,6-Dimethylphenol (102.8 g, 0.842 mol) and chloroacetic acid (159.6 g, 1.68 mol) in 1000 ml of $H_2O$ was added to a 3-L, 3-necked round bottom flask with mechanical stirring and a water-cooled condenser. A solution of NaOH (134.9 g, 3.37 mol) dissolved in 500 ml of water was slowly added to the above mixture via addition funnel and heat to reflux. After 2 hours, additional chloroacetic acid (79.4 g, 0.84 mol) and NaOH solution (67.2 g, 1.68 mol in in 200 ml water) was added to the reaction mixture. After 19 hours, additional chloroacetic acid (39.8 g, 0.42 mol) and NaOH solution (33.6 g, .84 mol in in 100 ml water) was added to the reaction mixture and refluxing was continued until starting phenol was consumed. The reaction flask was cooled in and ice-water bath and acidified to pH=1 with conc. HCl, causing a precipitate to form. The resulting slurry was stirred in the ice bath for 1 hour then filtered. The solid was dissolved in hot (100° C.) water and cooled to crystallize the product as white plates, mp=136–137° C., yield =78.8 9, 52%.

B. (2S,3S,5S) -2-(2,6-Dimethylphenoxyacetyl) amino-3-hydroxy-5-(t-butyloxycarbonylamino)-1,6-diphenylhexane Oxallyl chloride (36.3 ml, 0.42 mol) was added to a slurry of 2-6 dimethylphenoxyacetic acid (50 g, 0.28 mol) in 500 ml toluene followed by addition of 5 drops of DMF and stirred at room temperature for 30 min, then at 55° C. for 1.5 hours. The toluene was removed on a rotary evaporator and remaining volatiles were removed in vacuo to afford 2,6-dimethylphenoxyacetyl chloride as an amber oil, 55 grams, 100%. [2S,3S,5S]-2-Amino-3-hydroxy-5-t-butyloxycarbonylamino-1,6-diphenylhexane×0.5 succinate (111.9 g, 0.25 mol) was charged to a 2 L, 3-necked round-bottomed flask with mechanical stirring. $NaHCO_3$ (106 9, 1.26 mol), 600 ml $H_2O$ and 600 ml EtOAc were added and stirred vigorously until all solids were dissolved (15 minutes). Stirring was slowed and a solution of the 2,6-dimethyl-phenoxyacetyl chloride and EtOAc (100 ml) was added in a narrow stream via addition funnel. After 30 min of stirring, starting materials were consumed (HPLC analysis) and the layers were separated. The aqueous layer was extracted with EtOAc, the organic layers were combined and washed with 200 ml of 1 M NaOH, 200 ml of 10% HCl, 200 ml of brine, dried over $MgSO_4$, filtered and concentrated to provide the desired product as a white solid.

C. (2S,3S,5S) -2-(2,6-Dimethylphenoxyacetyl) amino-3-hydroxy-5-amino-1,6-diphenylhexane (2S,3S,5S) -2-(2,6-Dimethylphenoxyacetyl) amino-3-hydroxy-5-(t-butyloxycarbonylamino)-1,6-diphenylhexane (175.1 g, 0.32 mol) and 500 ml $CH_2Cl_2$ were mixed with stirring. $CF_3CO_2H$ (249 ml, 3.2 mol) was added and stirred 20–25 minutes, then the reaction mixture was poured into a separatory funnel containing 1000 ml of water and 200 ml of $CH_2Cl_2$. The resulting mixture was shaken carefully and the layers were separated. The organic layer was washed again with 500 ml of water, then 3×500 ml of $NaHCO_3$ and finally 500 ml of brine. The organic solution was dried over $MgSO_4$, filtered and concentrated to a golden oil that pulled into a foam 300 ml of diethyl ether was added to the crude product and shaken vigorously to dissolve. Within minutes solid began to crystallize and the mixture became thick. Enough diethyl ether was added to make the mixture stirrable and the mixture was stirred at room temperature for 1 hour. The solid was filtered and air dried to give the desired product as 115 g of white needles, 81% yield.

A solution of HCl/diethyl ether was added to the filtrate to precipitate the remaining product as the HCl salt. This pinkish solid was collected by filtration, taking care to keep the solid flooded with $N_2$ while it was wet with ether. When dry, transfered the amine salt to a separatory funnel and extracted with $CH_2Cl_2$ and $NaHCO_3$ (aq). The organic layer was washed with brine, dried over $MgSO_4$, concentrated and treated as above to afford an additional 15 g of the desired product, the total yield is 91%.

D. N-Carbonylbenzyloxy-3-aminopropanol

To a 1 2 L 3-neck round bottom flask was added isopropyl acetate (6.5 L). The solvent was cooled to 0° C. in an ice-water bath and 3-amino-1-propanol (1.14 Kg, 15.1 mol, 2.15 eq) was added in one portion. To this rapidly stirring solution, benzyl chloroformate (1.20 Kg, 7.03 mol, 1.0 eq) was added dropwise over 2 h while maintaining the internal temperature of the flask between 10° C. and 15° C. After the addition was complete, the reaction mixture was allowed to stir between 10° C. and 15° C. for an additional 0.3 h after which time water (3.5 L) was added in one portion. The solution was then partitioned and washed with an additional 2×3.5 L of water. The organic layer was dried over potassium carbonate and concentrated to give a solid that was dissolved in excess isopropyl acetate and precipitated from solution by adding the compound to heptane. The solid was filtered under nitrogen to yield 1.20 Kg (82%) of the desired product as a colorless solid.

E. N-Carbonylbenzyloxy-3-aminopropanal 335 mL of dimethylsulfoxide and 9 L of methylene chloride were combined and chilled to −48° C. 313 mL of oxalyl chloride was added over 25 minutes so that the temperature remained below −40° C. Cooled to −48° C., and added 500 grams of N-Cbz-3-amino-1-propanol dissolved in 1 L of methylene chloride so that the temperature remained below −40° C. Stirred for an additional hour at −45° C. 1325 mL of triethylamine was added at such a rate that the temperature remained below −40° C. After stirring an additional 15 minutes at −40° C., the mixture was allowed to warm to −30° C., then added 2.5 L of 20% aqueous potassium dihydrogen phosphate. Stirred for one hour, then separated the layers, washed the organic layer with brine, and dried with magnesium sulfate. The resulting aldehyde was kept in solution at −20° C. until needed.

F. N-(N-(Benzyloxycarbonyl-3-amino)-propyl)valine Methyl Ester

To a 5 L 3-neck round bottom flask was added the crude (unchromatographed) product of Example 24E (115 g, 0.555 mol, 1.0 eq) followed by addition of water (400 mL) and methanol (1600 mL). The reaction mixture was maintained at 25° C. throughout the course of the reaction. After the solution became homogeneous, (S)-Valine methyl ester hydrochloride (90.2 g, 0.538 mol, 0.97 eq) was added in one portion followed by rapid addition of sodium acetate trihydrate (151 g, 1.11 mol, 2.0 eq) and sodium cycanoborohydride (73.2 g, 1.17 mol, 2.1 eq) in said order. The reaction mixture was allowed to stir at room temperature for 0.5 h and was concentrated in vacuo to remove all methanol present. To this solution, saturated aq sodium bicarbonate (400 mL) was added and the mixture was extracted with isopropyl acetate (1 L). The organic layer was washed with water (2×400 mL), dried over sodium sulfate, and concentrated to yield 150 g of crude product, which was dissolved in isopropyl acetate (300 mL) and heptane (2400 mL). Dry HCl was bubbled in and an oily solid precipitated out of solution. The liquid was decanted away from the solid and was dissolved in dichloromethane (3 L). The solution was washed with water (600 mL) and saturated aq sodium bicarbonate (600 mL) and dried over sodium sulfate. It was concentrated in vacuo to yield 105 g (59%) of the desired product as a light yellow oil.

G. N-(3-amino)-propyl)valine Methyl Ester

To a 3 L flask was added the product of Example 24F (120 g, 0.372 mol) and methanol (1 L). This solution was allowed to stir in the presence of Raney Nickel (180 g) for 1 h . After removal of Raney Nickel by filtration, Pd(OH)2 (24 g) was added and the solution was allowed to stir under 60 psi of a hydrogen atmosphere for 12 h. The solution was purged with nitrogen and repressurized with 60 psi of hydrogen for an additional 1 h. The solution was filtered and concentrated to give 63 g of an oil (90%). To this oil toluene (120 mL) was added and the solution was again concentrated in vacuo to give the desired product.

H. 2S-(1-tetrahydro-pyrimid-2-onyl)-3-methyl Butanoic Acid Methyl Ester

To a 5 L 3-neck round bottom flask with stir bar was added the crude product of Example 24G (150 g, 0.5 mol) and dichloromethane (3.2 L). Carbonyldiimidazole (232 g, 1.44 mol, 1.8eq) was added slowly in portions over 25 min. The solution was allowed to stir at ambient temperature for 40h. Water (200 mL) was added over 1 h with careful stirring until no more gas evolution occurred. A solution of 35% HCl was slowly added to the stirring solution until the solution became acidic. The solution was then partitioned and was washed with water (2×300 mL). The organic layer was dried over sodium sulfate and was concentrated to yield 126 g (74%) of the desired product as a colorless solid.

I. 2S-(1-tetrahydro-pyrimid-2-onyl)-3-methyl Butanoic Acid Methyl Ester

To a 12 L 3-neck round bottom flask with stir bar was added the product of Example 24H (1 26 g, 0.588 mol), water (1.3 L), and THF(3.9 L). The solution was cooled to 0° C. in an ice-water bath and lithium hydroxide monohydrate (74 g, 1.76 mol, 3.0 eq) was added in one portion with rapid stirring. The solution was allowed to stir at 0° C. for 14 h. It was then acidified to pH 11 by slow addition of 50% aq phosphoric acid and the THF was removed in vacuo. The aqueous phase was washed with isopropyl acetate (2 L) and was subsequently acidified to pH by slow addition of 35% aq HCl. The aqueous layer was then extracted with ethyl acetate (5×2.2 L). The combined organic layers were concentrated to give the desired product (105 g) as a white solid. The compound was then purified by addition of isopropyl acetate (500 mL) and ethanol (15 mL) and bringing the solution to a boil with rapid stirring until 50 mL of solvent had evaporated. The solution was cooled to 0° C. and filered to give 92 g (75%) of pure desired product.

J. (2S,3S,5S)-2-(2,6-Dimethylphenoxyacetyl)amino-3-hydroxy-5-[2S-(1-tetrahydro-pyrimid-2-onyl)-3-methylbutanoyl]amino-16-diphenylhexane In a 2 L, 3-necked round-bottomed flask were combined the product of Example 24C (100 g, 0.22 mol), the product of Example 24I (44.8 g, 0.22 mol) and 750 ml DMF and the mixture was cooled in an ice/water bath. HOBT (90.9 g, 0.67 mol), EDAC (86 g, 0.45 mol) and triethylamine (62.5 ml, 0.45 mol) were added and the ice bath was removed, allowing the reaction mixture to stir with warming to room temperature for 5h. The reaction was diluted with 1000 ml of IPAC and quenched with 1000 ml of water. The mixture was shaken and separated, the aq. layer was extracted 1x 400 ml IPAC, the organics were washed with 1×400 ml 10% HCl, 1×500 ml NaHCO₃, diluted with 100 ml hexanes, then washed 4×500 ml water, and 1×500 ml brine, dried over MgSO₄, filtered and concentrated to provide the desired product as a white foam.

EXAMPLE 25

(2S,3S,5S)-2-(2,6-Dimethylphenoxyacetyl)amino-3-hydroxy-5-[2S-(1-tetrahydro-pyrimid-2,4-dionyl)-3-methylbutanoyl]amino-1,6-diphenylhexane

A. N-(2-Carbomethoxy)ethyl-L-Valine t-butyl Ester

To a solution of 1.73 g of L-Valine t-butyl ester in 10 ml of methanol was added 9.0 ml of methyl acrylate. The solution was heated to reflux overnight. Another 9.0 ml of methyl acrylate was added and continued the reflux for 24 h.

The solvent was evaporated in vacuo and the crude product was purified by silica gel column chromatography (20% ethyl acetate in hexane) to provide 2.435 g of desired compound (93.9%). 300 MHz 1H NMR (CDCl$_3$) δ 0.91 (d, J=3.5 Hz, 3H), 0.93 (d, J=3.5 Hz, 3H), 1.47 (s, 9H), 1.85 (m, 1H), 2.47 (t, J=7 Hz, 2H), 2.68 (m, 1H), 2.81 (d, J=6 Hz, 1H), 2.95 (m, 1H), 3.68 (s, 3H). Mass spectrum: (M+H)$^+$=260.

B. N-(2-Carboxamido)ethyl-L-Valine t-butyl Ester

To a solution of 1.86 g of the product from Example 25A in 5 ml of THF was added 0.415 g of lithium hydroxide monohydrate in 10.8 ml of water. After 40 min, 10.8 ml of 1 N HCl was added. The reaction mixture was evaporated to dryness and dry pyridine was added and evaporated to dryness two times. The residue was dissolved in 25 ml of acetonitrile and 0.62 ml of dry pyridine added. To this solution was added 2.02 g of N,N'-disuccinimidyl carbonate. The reaction mixture was stirred for 3.5 h. The solvent was removed in vacuo and 90 ml of THF added followed by 1.43 ml of conc. ammonium hydroxide. The reaction was allowed to go overnight. The reaction mixture was filtered and the filtrate concentrated in vacuo. The residue was dissolved in ethyl acetate and washed with sodium bicarbonate, brine and dried with anhy. sodium sulfate. After filtering off the drying agent, the filtrate was conc. in vacuo and the crude product was purified by silica gel column chromatography (5% MeOH in CH$_2$Cl$_2$) to give 1.19 g (68%) of desired compound. 300 MHz $^1$H NMR (CDCl$_3$) δ 0.95 (d, J=7 Hz, 3H), 0.97 (d, J=7 Hz, 3H), 1.48 (s, 9H), 1.93 (m, 1H), 2.37 (m, 2H), 2.65 (m, 1 HI, 2.95 (m, 2H), 5.30 (br s, 1H), 7.85 (br s, 1H). Mass spectrum: (M+H)$^+$=245.

C. 2S-(1-Tetrahydro-pyrimid-2,4-dionyl)-3-methylbutanoic Acid t-butyl Ester

A solution of 0.92 g of the product from Example 25B in 10 ml of THF and 1.83 g of carbonyldiimidazole (CDI) was refluxed for 26 h. Then 1.83 g of CDI was again added and the solution was refluxed for 72 h more. The solvent was evaporated in vacuo and the residue was dissolved in ethyl acetate and washed with water, satd. sodium bicarbonate, dilute hydrochloric acid and then brine. The organic layer was dried, filtered and conc. in vacuo. The crude product was purified by silica gel column chromatography (2% to 5% MeOH in CH$_2$Cl$_2$) to give 0.54 g (52%) of desired compound. 300 MHz $^1$H NMR (CDCl$_3$) δ 0.96 (d, J=7 Hz, 3H), 1.05 (d, J=7 Hz, 3H), 1.48 (s, 9H), 2.20 (m, 1H), 2.66 (m, 2H), 3.43 (m, 1H), 3.75 (m, 1H), 4.63 (d, J=9 Hz, 1H), 7.35 (br s, 1H). Mass spectrum: (M+H)$^+$=271.

D. 2S-(1-Tetrahydro-pyrimid-2,4-dionyl)-3-methylbutanoic Acid

A solution of 0.53 g of the compound from Example 25C in 5 ml of trifluoroacetic acid was stirred at 0° C. for 1.25 h. Solvent was evaporated in vacuo, dried and purified by silica gel column chromatography (2% MeOH/4% HOAc in CH$_2$Cl$_2$) to give 0.36 9 of desired compound. 300 MHz $^1$H NMR (DMSO-d$_6$) 50.86 (d, J=7 Hz, 3H), 0.97 (d, J=7 Hz, 3H), 2.15 (m, 1H), 3.40 (m, 4H), 4.39 (d, J=10 Hz, 1H). Mass spectrum: (M+H)$^+$=215.

E. (2S,3S,5S)-2-(2,6-Dimethylphenoxyacetyl)amino-3-hydroxy-5-[2S-(1-tetrahydro-pyrimid-2,4-dionyl)-3-methylbutanoyl]amino-1,6-diphenylhexane Coupling of the amino compound from Example 1 N with the acid from Example 25D using standard coupling procedure (EDAC in DMF) provided the desired compound (68%). 300 MHz 1H NMR (CDCl$_3$) δ 0.83 (d, J=7 Hz, 3H), 0.88 (d, J=7 Hz, 3H), 1.80 (m, 2H), 2.20 (s, 6H), 2.40 (m, 1H), 2.58 (m, 1H), 2.80 (m, 1H), 2.92 (m, 1H), 3.05 (m, 3H), 3.65 (d, J=5 Hz, 1H), 3.83 (m, 1H), 4.20 (m, 5H), 6.18 (d, J=9 Hz, 1H), 7.0–7.38 (m, 14H). Mass spectrum: (M+H)$^+$=643.

EXAMPLE 26

(2S,3S,5S)-2-(2,6-Dimethylphenoxyacetyl)amino-3-hydroxy-5[2S-(4-aza-1-tetrahydro-pyrimid-2-onyl)-3-methyl-butanoyl]amino-1,6-diphenylhexane

A. N(1)-t-butyloxycarbonyl-N(2)-allyl Hydrazine

To a solution of 18.18 g of t-butyloxycarbonyl protected hydrazine in 50 ml of acetonitrile was added 19.0 g of potassium carbonate, followed by 11.9 ml of allyl bromide. The reaction mixture was heated at reflux for a total of 3 h, filtered and conc. in vacuo. The residue was dissolved in ethyl acetate and washed with satd. sodium bicarbonate and dried with anhydrous sodium sulfate and filtered. After concentration in vacuo, the crude product was purified by silica gel column chromatography (20% EtOAc/hexane) to give 4.47 g of desired compound. 300 MHz 1H NMR (CDCl$_3$) δ 1.45 (s, 9H), 3.46 (m, 2H), 4.0 (br s, 1H), 5.10 (m, 2H), 5.83 (m, 1H), 6.0 (br s, 1H). Mass spectrum: (M+H)$^+$=173.

B. N(1)-t-butyloxycarbonyl-N(2)-allyl-N(2)-benzyloxycarbonyl Hydrazine

To a solution of 4.8 g of the compound from Example 26A in 15 ml of DMF was added 4.69 g of benzyloxycarbonyloxy-succinimide. The reaction mixture was stirred at RT for 72 h and the solvent was evaporated in vacuo. The residue was dissolved in ethyl acetate, washed with satd. sodium bicarbonate and dried with anhydrous sodium sulfate. The crude product obtained after concentration was purified by silica gel column chromatography (20% to 50% EtOAc in hexane) and provided 5.27 g of desired compound. 300 MHz $^1$H NMR (CDCl$_3$) δ 1.43 (brs, 9H), 4.15 (brs, 2H), 5.18 (s, 2H), 5.20 (m, 2H), 5.82 (m, 1H), 6.39 (br s, 1H), 7.36 (m, 5H). Mass spectrum: (M+H)$^+$=307.

C. N(1)-t-butyloxycarbonyl-N(2)-formylmethyl-N(2)-benzyloxycarbonyl Hydrazine A solution of 6.5 g of the compound from Example 26B in 100 ml of methanol was cooled with a dry ice/acetone bath. Ozone was bubbled in for 1.75 h until a pale blue color persisted. Air was passed through the solution for 10 min and then 15.6 ml of dimethyl sulfide was added and the reaction mixture was allowed to warm gradually to RT overnight. Solvent was evaporated in vacuo and the residue was dissolved in ethyl acetate and washed with water, then brine several times. The organic layer was dried with anhydrous sodium sulfate, filtered and conc. in vacuo to provide 7.2 g of the desired compound. 300 MHz 1H NMR (CDCl$_3$) δ 1.40 (br s, 9H), 4.35 (m, 2H), 5.20 (s, 2H), 6.65 (br s, 1H), 7.36 (s, 5H), 9.70 (br s, 1H). Mass spectrum: (M+N H$_4$)$^+$=326.

D. N-[2-(N-(2)-benxyloxycarbonyl-N-(1)-t-butyloxycarbonylhydrazinyl]ethy-L-Valine Methyl Ester To a solution of 7.2 g of the compound from Example 26C in 100 ml of methanol was added 3.55 g of L-valine methyl ester hydrochloride, followed by 3.48 g of sodium acetate and 1.33 g of sodium cyanoborohydride. The reaction mixture was stirred at RT overnight. The mixture was filtered and concentrated in vacuo. The crude product was purified by silica gel column chromatography (2% MeOH in $CH_2Cl_2$) to provide 5.8 g of desired compound. 300 MHz $^1H$ NMR ($CDCl_3$) δ 0.90 (d, J=6 Hz, 6H), 1.43 (br s, 9H), 1.87 (m, 1H), 2.60–3.0 (m, 4H), 3.72 (s, 3H), 5.18 (s, 2H), 7.37 (m, 5H). Mass spectrum: $(M+H)^+=424$.

E. 2S-[4-benzyloxycarbonylaza-1-tetrahydro-pyrimid-2-onyl)-3-methyl-butanoic Acid Methyl Ester A solution of 2.4 g of the compound from Example 26D in 20 ml of HCl in dioxane was stirred at RT under argon for 1 h. Solvent was evaporated in vacuo and the residue was washed with satd. sodium bicarbonate and extracted with ethyl acetate. The organic layer was dried, filtered and concentrated in vacuo. The crude product was dissolved in 28 ml of $CH_2Cl_2$ and 0.56 g of carbonyldiimidazole was added. The solution was left at RT for 48 h. The solvent was removed and the residue was purified by silica gel column chromatography (10% to 30% EtOAc in $CH_2Cl_2$) to give 0.78 g of desired compound. 300 MHz 1H NMR ($CDCl_3$) δ 0.90 (d, J=7 Hz, 3H), 0.98 (d, J=7 Hz, 3H), 2.17 (m, 1H), 3.34 (m, 1H), 3.61 (m, 2H), 3.72 (s, 3H), 3.98 (m, 1H), 4.71 (d, J=10 Hz, 1H), 5.20 (s, 2H), 6.72 (br s, 1H), 7.38 (m, 5H). Mass spectrum: $(M+H)^+=350$.

F. 2S-(4-Benzyloxycarbonylaza-1-tetrahydro-pyrimid-2-onyl)-3-methyl-butanoic Hydrolysis of 0.78 g of the compound from Example 26E using lithium hydroxide in aqueous dioxane provided 0.35 g of desired compound. 300 MHz 1H NMR ($CDCl_3$) δ 0.85 (d, J=7 Hz, 3H), 1.04 (d, J=7 Hz, 3H), 2.40 (m, 1H), 3.40 (m, 1H), 3.50 (m, 1H), 3.80 (m, 2H), 3.95 (d, J=10 Hz, 1H), 5.20 (s, 2H), 7.30 (s, 1H), 7.36 (s, 5H). Mass spectrum: $(M+H)^+=336$.

G. (2S,3S,5S)-2-(2,6-Dimethylphenoxyacetyl) amino-3-hydroxy-5[2S-(benzyloxycarbonylaza-1-tetrahydro-pyrimid-2-onyl)-3-methyl-butanyl]amino-1,6-diphenylhexane Coupling of the amino compound from Example 1N with the acid from Example 26F using standard coupling procedure (EDAC/DMF) provided the desired compound (36%). 300 MHz 1H NMR ($CDCl_3$) δ 0.72 (d, J=7 Hz, 3H), 0.83 (d, J=7 Hz, 3H), 2.20 (s, 6H), 2.65 (m, 1H), 2.83 (m, 1H), 3.0–3.10 (m, 4H), 3.90 (m, 1H), 6.65 (m, 1H), 7.0–7.35 (m, 1 8H). Mass spectrum: $(M+H)^+=764$.

H. (2S,3S,5S)-2-(2,6-Dimethylphenoxyacetyl) amino-3-hydroxy-5[2S-(4-aza-1-tetrahydro-pyrimid-2-oxyl)-3-methyl-butanoyl]amino-1,6-diphenylhexane Removal of the benzyloxycarbonyl protecting group of the compound from Example 26G by hydrogenolysis using 10% palladium on carbon as catalyst provided the desired compound. 300 MHz $^1H$ NMR ($CDCl_3$) δ 0.83 (d, J=4.5 Hz, 3H), 0.86 (d, J=4.5 Hz, 3H), 1.80 (m, 1H), 2.20 (s, 6H), 2.58 (m, 1H), 2.67 (m, 1H), 2.90 (m, 2H), 3.0 (m, 2H), 3.80 (m, 1H), 4.20 (m, 3H), 6.72 (m, 1H), 7.0 (m, 2H), 7.20 (m, 11H). Mass spectrum: $(M+H)^+=630$.

EXAMPLE 27

(2S,3S,5S)-2-(2,6-Dimethylphenoxyacetyl)amino-3-hydroxy-5-[2S-(1-tetrahydro-pyrimid-2-onyl)-3-methylbutanoyl]amino-1-phenyl-6-methylheptane

A. (2S,3S,5S)-2-Amino-3-hydroxy-5-(t-butyloxycarbonylamino)-1-phenyl-6-methylheptane Following the procedures described in Example 1A to Example 1F-1, but substituting isopropylmagnesium chloride for benzylmagnesium chloride in Example 1C provided the desired compound. 300 MHz $^1H$ NMR ($CDCl_3$) δ 0.88 (d, J=7 Hz, 3H), 0.92 (d, J=7 Hz, 3H), 1.43 (s, 9H), 1.50–1.80 (m, 4H), 2.55 (m, 1H), 2.90 (m, 1H), 3.0 (m, 1H), 3.54 (m, 2H), 4.62 (m, 1H), 7.30 (m, 5H). Mass spectrum: $(M+H)^+=337$.

B. (2S,3S,5S)-2-(2,6-Dimethylphenoxyacetyl) amino-3-hydroxy-5-(t-butyloxycarbonylamino)-1-phenyl-6-methylheptane Coupling of the amino compound from Example 27A with the acid from Example 1H using standard EDAC coupling procedure provided the desired compound. 300 MHz 1H NMR ($CDCl_3$) δ 0.85 (d, J=7 Hz, 3H), 0.90 (d, J=7 Hz, 3H), 1.43 (s, 9H), 1.70 (m, 2H), 2.20 (s, 6H), 3.03 (d, J=BHz, 2H), 3.42 (m, 1H), 3.80 (m, 1H), 4.20 (m, 2H), 4.22 (s, 2H), 4.55 (m, 1H), 7.0 (m, 3H), 7.30 (m, 5H). Mass spectrum: $(M+H)^+=499$.

C. (2S,3S,5S)-2-(2,6-Dimethylphenoxyacetyl) amino-3-hydroxy-5-amino-1-phenyl-6-methylheptane Removal of the t-butyloxycarbonyl protecting group of the compound from Example 27B using the procedure of Example 1 N provided the desired compound. 300 MHz 1H NMR ($CDCl_3$) δ 0.90 (d, J=3 Hz, 3H), 0.94 (d, J=3 Hz, 3H), 1.60 (m, 4H), 2.20 (s, 6H), 2.85 (m, 2H), 3.0 (m, 1H), 3.85 (m, 1H), 4.20 (m, 2H), 7.0 (m, 2H), 7.35 (m, 6H). Mass spectrum: $(M+H)^+=399$.

D. (2S,3S,5S)-2-(2,6-Dimethylphenoxyacetyl) amino-3-hydroxy-5-,2S,(1-tetrahydro-pyrimid-2-onyl)-3-methylbutanoyl]amino-1-phenyl-6-methylheptane Coupling of the amino compound from Example 27C with the acid from Example 2A using standard coupling procedure (EDAC/DMF) provided the desired compound. 300 MHz 1H NMR ($CDCl_3$) δ 0.88 (m, 12H), 1.67 (m, 2H), 1.90 (m, 1H), 2.20 (s, 6H), 3.0 (d, J=8 Hz, 2H), 3.22 (m, 4H), 3.67 (m, 1H), 3.77 (m, 1H), 4.20 (s, 2H), 4.40 (m, 1H), 4.76 (m, 1H), 7.0 (m, 3H), 7.30 (m, 5H). Mass spectrum: $(M+H)^+=581$.

EXAMPLE 28

(2S,3S,5S)-2-(2,6-Dimethylphenoxyacetyl)amino-3-hydroxy-5-[2S-(1-tetrahydro-pyrimid-2,4-dionyl)-3-methylbutanoyl]amino-1-phenyl-6-methylheptane Coupling of the amino compound from Example 27C with the acid from Example 25D using standard coupling procedure (EDAC/DMF) provided the desired compound. 300 MHz 1H NMR ($CDCl_3$) δ 0.83 (d, J=7 Hz, 6H), 0.92 (t, J=7 Hz, 6H), 1.73 (m, 2H), 2.18 (s, 6H), 2.30 (m, 1H), 2.62 (m, 2H), 3.03 (m, 2H), 3.45 (m, 1H), 3.55 (m, 1H), 4.72 (m, 2H), 4.20 (m, 4H), 6.40 (br d, J=9 Hz, 1H), 7.0 (m, 3H), 7.30 (m, 5H), 7.62 (br s, 1H). Mass spectrum: $(M+H)^+=595$.

EXAMPLE 29.

(2S,3S,5S)-2-(2,6-Dimethylphenoxyacetyl)amino-3-hydroxy-5-[2S-(1-piperazin-2,3-dionyl)-3-methylbutanoyl]amino-1,6-diphenylhexane

A. 2S-(4-benzyloxycarbonyl-1-piperazin-2,3-dionyl)-3-methylbutanoic Acid Methyl Ester To a solution of 0.77 g of N-(benzyloxycarbonylamino)-ethyl-L-Valine methyl ester in 20 ml of toluene and 10 ml of acetonitrile was added 0.79 g of oxalyl diimidazole. The reaction mixture was kept at 50° C. for 24 h and 0.2 g of oxalyl diimidazole was added. The reaction mixture was kept at 50° C. for another 72 h. Evaporation of solvent in vacuo and purification of the crude product by silica gel column chromatography (10% EtOAc in $CH_2Cl_2$) provided the desired compound. 300 MHz 1H NMR ($CDCl_3$) δ 0.95 (d, J=7 Hz, 3H), 1.03 (d, J=7 Hz, 3H), 2.20 (m, 1H), 3.60 (m, 1H), 3.73 (s, 3H), 3.85 (m, 1H), 4.0 (m, 1H), 4.10 (m, 1H), 4.90 (d, J=10 Hz, 1H), 5.36 (s, 2H), 7.20 (m, 5H). Mass spectrum: $(M+NH_4)^+$=380.

B. 2S-(1-piperazin-2,3-dionyl)-3-methylbutanoic Acid Methyl Ester

Removal of the benzyloxycarbonyl protecting group of the compound from Example 29A by hydrogenolysis using 10% Pd/C as catalyst provided the desired compound. 300 MHz 1H NMR ($CDCl_3$) δ 0.95 (d, J=7 Hz, 3H), 1.03 (d, J=7 Hz, 3H), 2.20 (m, 1H), 3.50 (m, 3H), 3.74 (s, 3H), 3.83 (m, 1H), 5.0 (d, J=10 Jz, 1H), 7.30 (br s, 1H). Mass spectrum: $(M+H)^+$=229.

C. (2S,3S,5S)-2-(2,6-Dimethylphenoxyacetyl) amino-3-hydroxy-5[2S-(1-piperazin-2,3-dionyl)-3-methylbutanoyl]amino-1,6-diphenylhexane The methyl ester from Example 29B was hydrolyzed using the procedure of Example 1 M and the resulting acid was coupled to the amino compound from Example 1 N using standard EDAC coupling procedure to provide the desired compound. 300 MHz 1H NMR ($CDCl_3$) δ 0.82 (d, J=6 Hz, 3H), 0.85 (d, J=6 Hz, 3H), 1.80 (m, 2H), 2.18 (m, 1H), 2.20 (s, 6H), 2.65 (m, 1H), 2.82–3.0 (m, 4H), 3.30 (m, 3H), 3.70 (m, 1H), 3.82 (m, 1H), 4.22 (m, 3H), 4.54 (d, J=10 Hz, 1H), 6.30 (br s, 1H), 6.65 (br d, 1H), 7.0–7.30 (m, 13H). Mass spectrum: $(M+H)^+$=643.

EXAMPLE 30

(2S,3S,5S)-2-(2,6-Dimethylphenoxyacetyl)amino-3-hydroxy-5[2S-(4-aza-4,5-dehydro-1-pyrimid-2-onyl)-3-methyl-butanoyl]amino-1,6-diphenylhexane A. 2S-(4-Aza-4,5-dehydro-1-pyrimid-2-onyl)-3-methyl-butanoic Acid From the hydroysis product mixture of Example 26F, the desired product was isolated after column chromatography (5% MeOH/5% AcOH in $CH_2Cl_2$) in 12.5% yield. 300 MHz $^1$H NMR ($CD_3OD$) δ 0.93 (d, J=7 Hz, 3H), 1.04 (d, J=7 Hz, 3H), 2.20 (m, 1H), 3.92 (dd, J=15, 3 Hz, 1H), 4.09 (dd, J=15, 3 Hz, 1H), 4.50 (d, J=1 0 Hz, 1H), 6.95 (t, J=3 Hz, 1H). Mass spectrum: $(M+H)^+$=334.

B. (2S,3S,5S)-2-(2,6-Dimethylphenoxyacetyl) amino-3-hydroxy-5[2S-(4-aza-4,5-dehydro-1-pyrimid-2-oxyl)-3-methyl-butanoyl]amino-1,6-diphenylhexane Coupling of the compound from Example 1N with the acid from Example 30A using standard coupling procedure (EDAC/DMF) provided the desired compound (70%). 300 MHz 1H NMR ($CDCl_3$) δ 0.80 (d, J=7 Hz, 3H), 0.85 (d, J=7 Hz, 3H), 1.75 (m, 2H), 2.15 (m, 1H), 2.20 (s, 6H), 2.62 (m, 1H), 2.85 (m, 1H), 3.02 (m, 2H), 3.55 (m, 2H), 3.80 (m, 1H), 4.20 (m, 4H), 6.38 (br d, 1H), 6.72 (t, J=3 Hz, 1H), 7.0 (m, 3H), 7.22 (m, 1OH), 7.63 (s, 1H). Mass spectrum: $(M+H)^+$= 628.

EXAMPLE 31 cis-N-tert-butyl-decahydro-2-[2(R)-hydroxy-4-phenyl-3(S)-(2S-(1-tetrahydropyrimid-2-onyl)-3-methylbutanoyl)aminobutyl]-(4aS,8aS)-isoquinoline-3(S)-carboxamide The title compound can be prepared by coupling the product of Example 2A with cis-N-tert-butyl-decahydro-2-[2(R)-hydroxy-4-phenyl-3(S)-aminobutyl]-(4aS,8aS)-isoquinoline-3(S)-carboxamide (disclosed in PCT Patent Application No. WO9426749 and U.S. Pat. No. 5,196,438, issued Mar. 23, 1993, both of which are incorporated herein by reference) using a standard coupling procedure (EDAC in DMF).

EXAMPLE 32 cis-N-tert-butyl-decahydro-2-[2(R)-hydroxy-4-thiophenyl-3(S)-(2S-(1-tetrahydropyrimid-2-onyl)-3-methylbutanoyl)aminobutyl]-(4aS,8aS)-isoquinoline-3(S)-carboxamide The title compound can be prepared by coupling the product of Example 2A with cis-N-tert-butyl-decahydro-2-[2(R)-hydroxy-4-thiophenyl-3(S)-aminobutyl]-(4aS,8aS)-isoquinoline-3(S)-carboxamide (disclosed in PCT Patent Application No. WO95/09843, published Apr. 13, 1995 and U.S. Pat. No. 5,484,926, issued Jan. 16, 1996, both of which are incorporated herein by reference) using a standard coupling procedure (EDAC in DMF).

EXAMPLE 33

4-Amino-N-((2syn. 3S)-2-hydroxy-4-phenyl-3-(2S-(1-tetrahydropyrimid-2-onyl)-3-methylbutanoylamino)-butyl)-N-isobutyl-benzenesulfonamide The title compound can be prepared by coupling the product of Example 2A with 4-Amino-N-((2syn, 3S)-2-hydroxy-4-phenyl-3-amino)-butyl)-N-isobutyl-benzenesulfonamide (disclosed in PCT Patent Application No. WO94/05639, published Mar. 17, 1994, which is incorporated herein by reference) using a standard coupling procedure (EDAC in DMF).

EXAMPLE 34

A. Alternative Preparation of (2S,3S,5S) -2-(2,6-Dimethylphenoxyacetyl)amino-3-hydroxy-5-amino-1,6-diphenylhexane To a 1 liter 3-necked flask equipped with a mechanical stirrer, J-Kem® temperature probe, dropping addition funnel, and dry nitrogen line was charged 30.0 g (54.87 mmol) of the product of Example 11 and 120 mL of acetonitrile. The resultant slurry was cooled to 0–5° C. and 54.1 g (549 mmol) of 37% aqueous hydrochloric acid was slowly added, maintaining an internal temperature of not more than +5° C. during the addition. The reaction mixture was stirred at 0–5° C. and samples were taken periodically to analyze for consumption of starting material by HPLC (Zorbax C-8 column, mobile phase =1:1 acetonitile/0.1% aqueous phosphoric acid, flow rate =1.5 mL/minute, detection at 205 nm).

After stirring for 3 hours the reaction was complete. The reaction was quenched by the slow addition of 105 mL of 20% aqueous sodium hydroxide, again maintaining an internal temperature of not more than +5° C. during the addition. Once the pH of the reaction mixture was confirmed to be basic, the solution was warmed to room temperature. Ethyl acetate (180 mL) was added with mixing and, after settling, the lower aqueous phase was separated and discarded. The organic phase was then washed once with 105 mL of 10% aqueous sodium chloride.

The title compound was crystallized from 12 mL/g of 1:2 ethyl acetate/heptane (yield 80–85%).

B. Alternative Preparation of (2S,3S,5S)-2-(2,6-Dimethylphenoxyacetyl)amino-3-hydroxy-5-amino-1,6-diphenylhexane To a round-bottom 3-neck 1 L flask with attached mechanical stirbar and thermometer was added the product of Example 11 (51.6 g, 0.095 mol) and 100 mL of glacial acetic acid. To the resulting suspension was added 35% aqueous HCl (10.5 mL, 0.103 mol) in 1 portion. The solution was allowed to stir under a $N_2$ atmosphere for 3h, at which time an additional 10.5 mL of 35% aqueous HCl was added. After an additional 1.5 h, the reaction flask was immersed in an ice bath and a NaOH solution (16 mL, 0.198 mol) was added at a rate to maintain the internal temperature of the flask below 30° C. Water (200 mL) was added and the mixture extracted with 4×200 mL of Isopropyl Acetate. The combined organic layers were washed with 2.5M NaOH (2×200 mL), 100 mL $H_2O$, brine, dried over $Na_2SO_4$, filtered and evaporated in vacuo to yield 39.7 g (94% crude) of product as a colorless solid in greater than 95% purity by HPLC. The product could be further purified by dissolving in 200 mL isopropanol heated over a steam bath, allowed to cool with stirring to 0–5° C. to yield 32.2 g (76%) of the desired product, m.p. =131° C.

EXAMPLE 35

Alternative Preparation of 2S-(1-Tetrahydro-pyrimid-2-onyl)-3-methyl Butanoic Acid

A. N-phenoxycarbonyl-L-valine

N-phenoxycarbonyl-L-valine may be prepared according to the procedures disclosed in U.S. patent application No. 08/08/671,893, filed Jun. 28, 1996, which is incorporated herein by reference, and which include the following method.

Into a reactor equipped with an overhead stirrer, chiller, pH probe and thermocouple was added lithium chloride (15.6 kg, 368 moles), L-valine (26.0 kg, 222 moles), neutral alumina (8.1 kg, 150 mesh, Aldrich) and 156 kg of distilled water. The heterogeneous mixture was stirred and cooled to -14° C. +5° C. The pH was adjusted to 10.1 with 10% aqueous lithium hydroxide. Precooled (-20° C.) phenylchloroformate (36.6 kg, 234 moles) was added while maintaining a temperature of not more than −9° C. and the pH was controlled during the reaction (maintaining a pH within the range of 9.5 to 10.5 with a target of 10.0) using a continuous addition of 10% aqueous lithium hydroxide.

The reaction was stirred for 2 hours at about −14° C. The reaction mixture was filtered through Celite and the filter cake was washed with 42 kg of distilled water. The aqueous filtrate was extracted with methyl t-butyl ether (65 kg) to remove residual phenol. The aqueous phase was then cooled to 0–5° C. and mixed with 200 kg of toluene. The stirred biphasic solution was adjusted to pH 1.8–2.0 with 25% (w/w) sulfuric acid. The toluene layer was concentrated at not more than 40° C. to approximately 120 L, filtered (30 kg rinse of toluene) and then concentrated again at not more than 40° C. to approximately 120 L.

To the resulting solution was added 44.2 kg of heptane and the resulting solution was heated to 40° C.±10° C. for 15 minutes. The heat was removed and the solution was seeded and stirred overnight. The product crystallized on the walls of the reactor and was resuspended in 80 kg of toluene, reconcentrated at not more than 50° C. to approximately 130 L, then 45.2 kg of heptane was added. The resulting solution was then heated to 40° C.+1° C. for not less than 15 minutes and then cooled at not more than 20° C./hour to 18° C.±5° C. After not less than 12 hours, the resulting white slurry was cooled to 14° C.±5° C. and stirred for not less than 3 hours. The white slurry was filtered and the solid washed with 41 kg of 1:1 toluene/heptane. The solid product was dried at not more than 50° C. to provide the desired product (47.8 kg) as a white powder.

B. 2S-(1-Tetrahydro-pyrimid-2-onyl)-3-methyl butanoic acid

A mixture of N-phenoxycarbonyl-L-valine (25 g, 0.106 mol) and 3-chloropropylamine hydrochloride (15.2 g, 0.116 mol) in THF (250 mL) was cooled to 2° C. Sodium hydroxide (12.7 g, 0.318 mol) was added to the stirring suspension. After about 35 minutes, a slow exotherm to 1° C. occurred. The reaction was stirred at less than 1 0° C. for 2 hours. A solution of potassium t-butoxide (29.6 g, 0.265 mol) in 125 mL of THF was added over 10 minutes, followed by a 20 mL THF rinse. The temperature of the reaction mixture was allowed to rise to 20° C. during the addition. The reaction mixture was stirred at room temperature for 19 hours.

The reaction mixture was quenched with 200 mL of distilled water and then acidified to pH 9 using 26.2 g of concentrated hydrochloric acid, keeping the temperature below 30° C. The aqueous layer was separated and washed with another 125 mL of THF. Ethanol 3A (75 mL) was added to the separated aqueous layer and the mixture was acidified to pH <3 with 12.3 g of concentrated hydrochloric acid, keeping the temperature below 25° C. The acidified mixture was extracted twice with ethyl acetate (250 mL and 150 mL). The combined organic layers were evaporated to dryness on a rotary evaporator at a temperature below 50° C. The residual solids were flushed with 250 mL of ethyl acetate. The residual solid was dissolved in 150 mL of ethanol 3A at reflux temperature and filtered through a 5 g Darco-G60 bed over filteraid, followed by a 50 mL hot ethanol rinse. The filtrate was evaporated to dryness on a rotary evaporator at a temperature below 50° C. Ethyl acetate (75 mL) was added to the residue and refluxed for 30 minutes. The suspension was cooled to below 1° C. for 2 hours. The solid was collected by filtration and washed with 20 mL of cold ethyl acetate (5–8° C.). After drying at 40° C. for 72 hours the desired product was obtained as a white solid (15.6 g, 74%).

EXAMPLE 36

Alternative Preparation of 2S-(1-Tetrahydro-pyrimid-2-onyl)-3-methyl Butanoic Acid A mixture of phenoxycarbonyl-L-valine (250 g, 1.05 mol; prepared according to the procedure disclosed in U.S. patent application Ser. No. 08/671,893, filed Jun 28, 1996, which is incorporated herein by reference) and 3-chloropropylamine hydrochloride (151 g, 1.16 mol) in THF (2.5 L) is cooled to 2° C. Sodium hydroxide (127 g, 3.2 mol) is added to the stirring suspension. After about 45 minutes, a rapid exotherm to 10° C. occurrs. The reaction is stirred at 1–5° C. for 2 hours. Additional 3-chloropropylamine (10 g, 0.08 mol) is added and stirring is continued for 1 hour. A solution of potassium t-butoxide (296 g, 2.6 mol) in 1.25 L of THF is then added over 30 minutes, followed by a 100 mL THF rinse. The temperature of the reaction mixture was allowed to rise to 20° C. during the addition. The reaction mixture is stirred at room temperature for 12–16 hours.

The reaction mixture is quenched with 2 L of distilled water and cooled to 1 2° C. and then acidified to pH 9 using 258 g (2.6 mol) of concentrated hydrochloric acid, keeping the temperature below 30° C. The aqueous layer is separated. Ethanol 3A (625 mL) is added to the separated aqueous layer and the mixture was acidified to pH <3 with 116 g (1.2 mol) of concentrated hydrochloric acid, keeping the temperature below 25° C. The acidified mixture is extracted twice with ethyl acetate (2.5 L and 1.5 L). The combined organic layers are evaproated to dryness on a rotary evaporator at a temperature below 50° C. The residual solids are dried by repeated distillation with ethyl acetate (4 ×1 L). The residual solid is dissolved in 750 mL of methanol and treated with decolorizing carbon (10 g Darco-G60 bed) at room temperature overnight. The carbon is removed by filtration through diatomaceous earth. The filtrate is evaporated to dryness on a rotary evaporator at a temperature below 50° C. Ethyl acetate (1.5 L) is added to the residue and approximately 500 mL is removed on the rotary evaporator. The suspension is cooled to below 1° C. for >1 hour. The solid is collected by filtration and washed with 2×100 mL of cold ethyl acetate (5–8° C.). After drying at 50° C. for 72 hours the desired product is obtained.

EXAMPLE 37

Alternative Preparation of 2S-(1-Tetrahydro-pyrimid-2-onyl)-3-methyl Butanoic Acid A. (S)-(–)-N-carboxymethyl-N(β)cyanoethyl Valine To a 5 L 3-neck round bottom flask with a mechanical stirrer was added (S)-valine (170.1 g, 1.45 mol) and water 145 mL. The solution was cooled to 0° C. with an ice-water bath and a solution of 1.0 eq of KOH (93 g of 88% solid KOH) in 180 mL water was added dropwise over 20 minutes. After the addition was complete, acrylonitrile 1.0 eq (95.5mL) was added dropwise with vigorous stirring while maintaining the internal temperature of the flask below 5° C. The solution was allowed to stir between 0–5° C. for 4.5 h. Water (600 mL) was added and a pH meter was inserted into the solution. Methyl chloroformate 1.0 eq (112 mL) was added dropwise while maintaining the pH of the solution between 9.5 and 10.5, with solution of 10% aq KOH. The addition took place over 0.5 h. The solution was then acidified with conc. HCl and phosphoric acid to pH 2 and was subsequently extracted with 2 L of isopropyl acetate. The organic layer was concentrated under vacuum to give 201 g (60%) of a colorless oil that solidified on standing. mp 65–66° C. Optical rotation sodium D line at 25° C.–0.44 (c=4.3, ethanol). IR (cm$^{-1}$, CDCl$_3$) 2960, 1740, 1710, 1470. 1H NMR (300 MHz, CDCl$_3$); (δ TMS, 0.00) ppm 0.93 (d, 3H J=7 Hz); 1.07 (d, 3H J=6 Hz); 2.16–2.36 (m, 1H); 2.62–2.86 (m, 2H); 3.62 (t, 2H, J=7.5 Hz); 3.77 (s, 1.2H rotamer); 3.82 (s, 1 .8H rotamer); 4.15–4.30 (m, l H); 9.76–9.96 (brs, l H). ms (DCI/NH$_3$) 246, 185, 146, 125. FAB hrms: cal for (M+H$^+$): 229.1188; found: 229.1185.

B. 2S-(1-Tetrahydro-pyrimid-2-onyl)-3-methyl Butanoic Acid

To a 2 L pressure vial was added the product of Example 37A (190 g, 0.833 mol), water (900 mL) and KOH (3eq, 140 g). To this solution at ambient temperature was added Nickel Aluminum alloy (Raney-Type) 75 g. Note that this is the unactivated form. The solution was sealed in a pressure bomb and was placed under 60 psi of hydrogen. The resulting solution was heated to 100° C. for 4 h. After cooling the solution to ambient temperature, it was filtered, washed with 900 mL of dichloromethane and subsequently acidified to pH 1. The aqueous solution was extracted with 2×900 mL of dichloromethane. The combined organic layers were concentrated to give 120 g of crude product which was slurried in isopropyl acetate to give 70 g of the title compound.

EXAMPLE 38

Alternative Preparation of (2S,3S,5S)-2-(2,6-Dimethylphenoxyacetyl)amino-3-hydroxy-5-[2S-(1-tetrahydro-pyrimid-2-onyl)-3-methyl butanoyl] amino-1,6-diphenylhexane A-1. 2S-(1-Tetrahydro-pyrimid-2-onyl)-3-methyl Butanoyl Chloride 2S-(1-Tetrahydro-pyrimid-2-onyl)-3-methyl butanoic acid (17.6 g, 87.9 mmole) was slurried in THF (240 mL) and cooled to <5° C. Thionyl chloride (14.3 g, 120 mmole) was added over 5 minutes (exothermic). The slurry was stirred at 20° C. for 70 min. until complete by HPLC (samples quenched into methanol). THF was removed by rotary evaporation; heptane (90 mL) was added and removed by rotary evaporation, yielding a wet solid mass. The material was slurried in DMF (85 mL).

A-2. Alternative Preparation of 2S-(1-Tetrahydro-pyrimid-2-onyl)-3-methyl Butanoyl Chloride 2S-(1-Tetrahydro-pyrimid-2-onyl)-3-methyl butanoic acid (39.6 g, 198 mmole) was slurried in THF (590 mL) and cooled to 1° C. Thionyl chloride (28.3 g, 238 mmole) was added over 5 minutes (exothermic). The slurry was stirred at 20° C. for 2 hours. THF was removed on the rotary evaporator; THF (200 mL) was added and removed on the rotary evaporator, yielding a wet solid mass. The material was slurried in DMF (225 mL).

B-1. (2S,3S,5S)-2-N,N-dibenzylamino-3-hydroxy-5-[2S-(1-tetrahydro-pyrimid-2-onyl)-3-methylbutanoyl]amino-1,6-diphenylhexane (2S,3S,5S)-2-N,N-dibenzylamino-3-hydroxy-5-amino-1,6-diphenylhexane (ca. 83 mmole; U.S. Pat. No. 5,491,253, issued Feb. 13, 1996, which is incorporated herein by reference) and imidazole (8.2 g, 120 mmole) were dissolved in ethyl acetate (350 mL, KF <0.1 %) and cooled to 2° C. The slurried product of Example 38A-1 was added (exothermic, maximum temp. was 10° C.), followed by a DMF rinse (15 mL). The reaction was stirred cold initially then allowed to slowly warm to room temperature and stirred overnight.

The reaction was quenched with 100 mL water and stirred 30 minutes. The organic layer was separated and washed with 3×125 mL 5% NaCl. The organic solution was filtered and concentrated on rotary evaporator to a thick syrup, 62 g. HPLC purity approx. 85% (peak area). Isomer content approx. 11.2%.

CIMS (NH$_3$) m/z 647 (M +H)$^+$.

$^1$H NMR (300 MHz, CDCl$_3$) 57.35–7.13 (m, 1OH), 7.13–7.06 (m, 1H), 6.87. (brd, 1H), 5.22 (br s, 1H), 4.28 (d, 1H), 4.20–4.05 (m, 1H), 3.95 (d, 2H), 3.65–3.56 (m, 1H), 3.37, (d, 2H), 3.12–2.89 (m, 5H), 2.83–2.53 (m, 4H), 2.23–2.08 (m, 1H), 1.74–1.40 (m, 4H), 0.87–0.75 (m, 6H).

$^{13}$C NMR (75 MHz, CDCl$_3$) δ 170.0, 156.6, 140.2, 139.1, 138.4,129.3, 129.1, 128.9, 128.4, 128.3, 128.0, 127.1, 126.0, 125.8, 69.1, 64.0, 63.1 (br), 54.2, 49.2, 41.2, 40.5, 40.0, 39.7, 31.5, 25.4, 21.6, 19.5, 18.6.

B-2. Alternative Preparation of (2S,3S,5S)-2-N,N-dibenzylamino-3-hydroxy-5-[2S-(1-tetrahydro-pyrimid-2-onyl)-3-methyl butanoyl]amino-1,6-diphenylhexane (2S,3S,5S)-2-N,N-dibenzylamino-3-hydroxy-5-amino-1, 6-diphenylhexane (ca. 180 mmole; U.S. Pat. No. 5,491,253, issued Feb. 13, 1996, which is incorporated herein by reference) and imidazole (38.1 g, 560 mmole) were dissolved in ethyl acetate (675 mL, KF<0.1%) and cooled to 1° C. The slurried product of Example 38A-2 was added slowly over 30 minutes (exothermic, maximum temp. was 6° C.), followed by an ethyl acetate rinse (225 mL). The reaction was stirred cold for 1. 5 hours, then allowed to slowly warm to about 27° C. and stirred for about 20 hours.

The reaction was quenched with a dilute solution of HCl (36.75 g concentrated HCl in 225 mL of water) and stirred 20 minutes. The biphasic mixture was filtered with a 100 mL ethyl acetate rinse. The organic layer was separated and washed with 3×125 mL 5% NaCl. The organic layer was separated and washed with 3×225 mL 5% NaCl and 2×225 mL 5% NaHCO$_3$. The organic solution was concentrated by rotary evaporation to provide the desired product as a thick syrup.

C. (2S,3S,5S)-2-Amino-3-hydroxy-5-[2S-(1-tetrahydro-pyrimid-2-onyl)-3-methylbutanoyl] amino-1,6-diphenylhexane The crude product of Example 38B (ca. 83 mmole) was dissolved in methanol (260 mL). Pd/C (50% wet Pearleman's catalyst, 10.4 g wet weight) and ammonium formate (15.1 g, 239 mmole) were added and the mixture was warmed to 50° C. After 2.5 hours the reaction was complete by TLC. The mixture was cooled to 35° C. and catalyst was removed by filtration through diatomaceous earth, followed by a methanol rinse (250 mL). The combined filtrate was concentrated on the rotary evaporator. The residue was dissolved in dioxane (150 mL) with warming. Dioxane was removed on the rotary evaporator to yield 60 g of yellow oil. HPLC purity approx. 88.2% (peak area). Isomer content ≧7.9% (however, one isomer does not separate from the main peak).

CIMS (NH$_3$) m/z 467 (M+H)$^+$

1H NMR (300 MHz, CD$_3$OD) δ 7.35–7.10 (m, 1 OH), 4.40–4.20 (m, 1H), 4.25 (d, 1H), 3.68–3.57 (m, 1H), 3.20–3.09 (m, 2H), 3.08–2.90 (m, 3H), 2.90–2.74 (m, 2H), 2.65–2.49 (m, 2H), 2.20–2.04 (m, 1H), 1.92–1.78 (m, 1H), 1.78–1.60 (m, 2H), 1.60–1.45 (m, 1H), 0.88–0.77 (m, 6H)

$^{13}$C NMR (75 MHz, CD$_3$OD) 3171.3, 158.4, 140.5, 139.8, 130.6, 130.4, 129.5, 129.3, 127.3, 127.0, 71.5, 63.9, 57.1, 49.1, 41.8, 41.6, 41.4, 40.7, 40.5, 26.9, 22.5, 20.0, 18.9

$^1$H NMR (300 MHz, CDCl$_3$) δ 7.35–7.13 (m, 1OH), 5.35 (s, 1H), 4.40–4.23 (m, 2H), 3.60–3.52 (m, 1H), 3.25–2.65 (m, 8H), 2.58–2.45 (dd, 1H), 2.30–2.10 (m, 1H), 1.90–1.65 (m, 3H), 1.65–1.50 (m, 1H), 0. 91 (d, 3H), 0.84 (d, 3H)

$^{13}$C NMR (75 MHz, CDCl$_3$) 8171.2, 156.6, 139.1, 138.5, 129.3, 129.2, 128.5, 128.2, 126.3, 126.0, 71.6, 63.1 (br), 56.3, 48.7, 41.6, 41.0, 40.6, 40.0, 39.6, 25.5, 21.7,19.7,18.7

D. (2S,3S,5S)-2-Amino-3-hydroxy-5-[2S-(1-tetrahydro-pyrimid-2-onyl)-3-methylbutanoyl] amino-1,6-diphenylhexane (S)-Pyroglutamic Acid Salt The crude product of Example 38C was dissolved in dioxane (370 mL, KF=0.07% moisture). S-Pyroglutamic acid (10.3 g, 80 mmole) was added and the suspension was warmed to 50° C. to give a clear solution. After stirring 1 hour the solution was seeded with a few crystals of the product salt. The salt slowly precipitated. The slurry was slowly cooled and stirred overnight at room temperature. The product was isolated by filtration and washed with dioxane (100 mL). Wet cake weight was 120 g. Product was dried at 60° C. in a vacuum oven with nitrogen purge. Yield 35.2 g off-white powder. HPLC purity: >98% (peak area including pyroglutamic acid). Isomer content approx. 1 % (however, one isomer does not separate from the main peak).

mp=135–141° C.

[a]D$^{25}$=–21.9° (c=2.5, CH$_{3OH}$)

CIMS (NH$_3$) mlz 467 (M +H for base)+, 147 (M+NH$_4$ for pyroglutamic acid)$^+$, 130 (M +H for pyroglutamic acid)$^+$ IR (KBr) 1586, 1655, 1682 cm$^{-1}$ $^1$H NMR (400 MHz, DMSO-d$_6$) δ 7.62 (s, 1H), 7.54 (d, 1H), 7.32–7.06 (m, 10H), 6.33 (s, 1H), 4.26 (d, 1H), 4.11–3.99 (m, 1H), 3.82 (dd, 1H), 3.57–3.48 (m, 1H), 3.27–3.19 (m, 1H), 3.08–2.95 (m, 2H), 2.92–2.70 (m, 5H), 2.53–2.43 (m, 1H), 2.26–2.14 (m, 1H), 2.13–1.99 (m, 2H), 1.99–1.87 (m, 2H), 1.72–1.61 (m, 2H), 1.61–1.49 (m, 1H), 1.46–1.35 (m, 1H), 0.70 (d, 3H), 0.64 (d, 3H).

13C NMR (100 MHz, DMSO-d$_6$) 6176.9, 176.1, 169.2, 155.5, 138.8, 137.7, 129.3, 129.3, 128.3, 127.8, 126.4, 125.5, 66.9, 61.5, 56.9, 55.3, 46.8, 40.2, 39.6, 39.4, 38.8, 37.4, 29.8, 25.4, 25.3, 21.6, 19.6,18.7.

$^1$H NMR (300 MHz, CD$_3$OD) δ 7.32–7.03 (m, 1 OH), 4.23–4.12 (m, 1H), 4.12 (d, 1H), 3.98 (dd, 1H), 3.71–3.63 (m, 1H), 3.46–3.37 (m, 1H), 3.11–2.98 (m, 2H), 2.97–2.80 (m, 4H), 2.70–2.59 (m, 1H), 2.49–2.38 (m, 1H), 2.38–2.12 (m, 3H), 2.07–1.92 (m, 2H), 1.75–1.63 (m, 2H), 1.63–1.50 (m, 1H), 1.45–1.32 (m, 1H), 0.74–0.65 (m, 6H).

13C NMR (75 MHz, CD$_3$OD) δ 181.0, 179.6, 171.6, 158.4, 139.5, 137.3, 130.5, 130.0, 129.4, 128.3, 127.2, 68.1, 64.0, 59.6, 57.7, 48.8, 41.7, 41.1, 40.7, 40.6, 37.9, 31.1, 26.9, 26.9, 22.5, 20.1, 18.9. $^1$H NMR (300 MHz, D$_2$0) δ 67.30–6.97 (m, 1OH), 4.16–4.03 (m, 1H), 3.99–3.91 (m, 2H), 3.71–3.63 (m, 1H), 3.43–3.35 (m, 1H), 3.00–2.68 (m, 6H), 2.40–2.13 (m, 5H), 1.88–1.72 (m, 3H), 1.68–1.56 (m, 1H), 1.52–1.37 (m, 1H), 1.32–1.18 (m, 1H), 0.60–0.52 (m, 6H).

$^{13}$C NMR (75 MHz, D$_2$0) 3181. 6,180.1, 171.0, 157.3, 137.9, 135.2, 129.3, 129.2, 129.1, 128.4, 127.6, 126.4, 67.3, 62.6, 58.2, 56.7, 47.5, 40.1, 39.4, 39.2, 38.7, 35.7, 29.6, 25.3, 25.2, 20.5,18.5, 17.6.

E. (2S,3S,5S)-2-(2,6-Dimethylphenoxyacetyl) amino-3-hydroxy-5-[2S-(1-tetrahydro-pyrimid-2-onyl)-3-methylbutanoyl]amino-1,6-diphenylhexane The product of Example 1H (7.26 g, 40.3 mmole) was slurried in ethyl acetate (22 mL) and thionyl chloride (5.75 g, 48.3 mmole) was added, followed by 1 drop DMF. The mixture was warmed to 50° C. and stirred 5 hours. The solution of the resulting acid chloride was cooled to 22° C. and held for the subsequent coupling reaction.

The product of Example 38D (20 g, 31.7 mmole, corrected for dioxane content), sodium bicarbonate (16.5 g, 197 mmole), ethyl acetate (150 mL) and water (150 mL) were combined in a flask and stirred until the product of Example 38D had dissolved (some salt remains undissolved). The solution of acid chloride prepared above was added over 5 minutes, followed by an ethyl acetate rinse (5 mL). Addition was mildly exothermic (maximum temperature 23° C.). The mixture was stirred overnight.

The organic layer was separated and washed with 5% sodium bicarbonate (100 mL) and water (100 mL). Solvent was removed on the rotary evaporator. The residue was dissolved in ethyl acetate (100 mL) and filtered, rinsing with ethyl acetate (50 mL). The solvent was removed from the combined filtrate on the rotary evaporator. The residue was dissolved in hot ethyl acetate (105 mL) and heptane (105 mL) was added; product began to crystallize rapidly. The slurry was cooled and stirred at 20–23° C. for 5 hours. Product was collected by filtration and washed with 1/1 (v/v) ethyl acetate/heptane (30 mL). Product was dried under vacuum oven at 70° C. to provide 18.8 g of the desired product as a white powder.

EXAMPLE 39

Preparation of Amorphous (2S,3S,5S)-2-(2,6-Dimethylphenoxyacetyl)amino-3-hydroxy-5-[2S-(1-tetrahydro-pyrimid-2-onyl)-3-methylbutanoyl] amino-1,6-diphenylhexane A. The product of Example 38E (2.5 g) was dissolved in 8 mL of absolute ethanol. This solution was added slowly dropwise to 250 mL of chilled water at 9° C. with vigorous stirring. A white solid immediately appeared. The stirring was continued for 15 minutes and the solids were collected by filtration. Vacuum drying at 50° C. for 12 hours provided 2.32 g of the desired product as an amorphous solid.

B. The product of Example 38E (2.5 9) was dissolved in 6 mL of absolute ethanol. This solution was added slowly dropwise to 31 mL of chilled water at 7–9° C. with vigorous stirring. A white solid appeared. The stirring was continued for 20 minutes and the solids were collected by filtration. Vacuum drying at 50° C. for 12 hours provided 2.24 g of the desired product as an amorphous solid.

C. The product of Example 38E (0.5 g) was dissolved in 8 mL of isopropanol. This solution was added slowly dropwise to 100 mL of chilled water at 10–15° C. with vigorous stirring. A white solid appeared. The stirring was continued for 20 minutes and the solids were collected by filtration. Air drying provided 0.48 g of the desired product as an amorphous solid.

D. The product of Example 38E (0.5 g) was dissolved in 8 mL of acetone and 0.2 mL of absolute ethanol. This solution was added slowly dropwise to 100 mL of chilled water at 10–1 5° C. with vigorous stirring. A white solid appeared. The stirring was continued for 10 minutes and the solids were collected by filtration. Air drying provided 0.46 g of the desired product as an amorphous solid.

E. The product of Example 38E (0.5 g) was dissolved in 2 mL of acetonitrile. This solution was added slowly dropwise to 100 mL of chilled water at 10–15° C. with vigorous stirring. A white solid appeared. The stirring was continued for 20 minutes and the solids were collected by filtration. Air drying provided 0.46 g of the desired product as an amorphous solid.

EXAMPLE 40

N-(3-Chlorogropylaminocarbonyl)-valine Methyl Ester

3-Chloropropylisocyanate (0.31 mL, 3.0 mmol) was added to a slurry of L-valine methyl ester hydrochloride (0.5 g, 3.0 mmol) and triethylamine (0.42 mL, 3.0 mmol) in THF (10 mL). The reaction mixture was stirred for 4 hours at room temperature and was then quenched with the addition of aqueous sodium bicarbonate. The quenched reaction mixture was extracted with ethyl acetate. The organic layer was separated, dried and evaporated to give the desired product.

EXAMPLE 41

(2S,3S,5S)-2-(2,6-Dimethylphenoxyacetyl)amino-3-hydroxy-5-[2S-(1-tetrahydro-4-hydroxy-pyrimid-2-onyl)-3-methyl butanoyl]amino-1,6-diphenylhexane Reaction of a solution of the product of Example 25E in methylene chloride with sodium borohydride provides the desired product.

EXAMPLE 42

(2S,3S,5S)-2-(2,6-Dimethylphenoxyacetyl)amino-3-hydroxy-5-[2S-(1-tetrahydro-6-hydroxy-pyrimid-2-onyl)-3-methylbutanoyl]amino-1,6-diphenylhexane A 300-mL incubation of (2S,3S,5S)-2-(2,6-Dimethylphenoxyacetyl) amino-3-hydroxy-5-[2S-(1-tetrahydro-6-hydroxy-pyrimid-2-onyl)-3-methyl butanoyl] amino-1,6-diphenylhexane labelled with $^{14}C$ in the carbonyl group of the acetyl moiety (50 ,M, 6.0 µCi) was performed with rat liver microsomes (0.5 mg/mL microsomal protein) and an NADPH-generating system for 60 minutes at 37° C. The metabolic reaction was stopped by adding 300 mL of acetonitrile. The supernatant obtained after centrifugation at 3000 RPM for 10 minutes was evaporated to dryness in vacuo. The residue was reconstituted in 2 mL of HPLC mobile phase. Isolation of the desired product was achieved at ambient temperature with a Beckman Ultrasphere 5 tm 10×150 mm $C_{18}$ column connected to an Alitech Ultrasphere 5 µm $C_{18}$ cartridge guard column. A linear gradient oh 25–55% acetonitrile in buffer (25 mM ammonium acetate, pH adjusted to 4.8 with formic acid) over 57 minutes was used as column eluent at a flow rate of 2.8 mL/minute.

Fluorogenic Assay for Screening Inhibitors of HIV Protease

The inhibitory potency of the compound of the invention can be determined by the following method.

The compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1 M sodium chloride, 5 mM dithiothreitol, 0.5 mg/ml bovine serum albumin, 1.3 IM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100×(1–(rate in presence of inhibitor)/(rate in absence of inhibitor)).

Fluorogenic substrate: Dabcyl-Gaba-Ser-Gln-Asn-Tyr-Pro-lle-Val-Gln-EDANS wherein DABCYL=4-(4-dimethylamino-phenyl)azobenzoic Acid, Gaba=γ-aminobutyric acid, and EDANS=5-((2-aminoethyl)amino)-naphthalene-1-sulfonic acid.

TABLE 1

| Compound of Example | Percent Inhibition | Inhibitor Concentration (nanomolar) |
|---|---|---|
| 1P | 92.6 | 0.5 |
| 2B | 93.2 | 0.5 |
| 3C | 86.9 | 0.5 |
| 4F | 49.7 | 0.5 |
| 5 | 80.8 | 0.5 |
| 6F | 61.4 | 0.5 |
| 7B | 67.1 | 0.5 |
| 8 | 55.6 | 0.5 |
| 9B | 62.6 | 0.5 |
| 10F | 81.0 | 0.5 |
| 11B | 91.1 | 0.5 |

TABLE 1-continued

| Compound of Example | Percent Inhibition | Inhibitor Concentration (nanomolar) |
|---|---|---|
| 12B | 76.8 | 0.5 |
| 13B | 56.2 | 1.0 |
| 14D | 52.7 | 0.5 |
| 15 | 48 | 0.5 |
| 17C | 87.2 | 0.5 |
| 18C | 57.8 | 0.5 |
| 19E | 68.5 | 0.5 |
| 22E | 71.8 | 0.5 |
| 23C | 86.0 | 0.5 |
| 25E | 100 | 0.5 |
| 26H | 94.6 | 0.5 |
| 27D | 92.9 | 0.5 |
| 28 | 86.6 | 0.5 |
| 29C | 72.6 | 0.5 |
| 30B | 91.0 | 0.5 |

Antiviral Activity

The anti-HIV activity of the compound of the invention can be determined in MT4 cells according to the following procedure. MT4 cells were infected with cell-free supernatant of HIVIIIB (previously frozen with known 50% tissue culture infectious dose ($TCID_{50}$) at 0.003 multiplicity of infection (MOI) for one hour. After one hour infection, cells were washed twice to remove residual viruses, resuspended in culture media and seeded into 96-well tissue culture plates at 1×10^4 cells per well with various half-log dilutions of compounds. Uninfected cells are included as toxicity and cell controls. RPMI 1640 media (Gibco ) with 10% fetal bovine serum were used as culture media. Various concentrations of human serum (Sigma) 50%, 25% and 12.5% were added to culture media resulting in final concentration of 60%, 35% and 22.5% total serum. All assay plates were incubated in 37 deg. cent. incubator for 5 days. MTT (sigma, 5 mg/ml stock in PBS) was added to all wells at 25 ul per well, incubate for 4 hours. 20%SDS with 0.02 N HCl in water was added at 50 ul per well to lyse cells. Plates incubated overnight for complete lyses were read on a microtitre plate reader at 5701650 nm wavelengths to determine cell optical density (O.D.). Raw data were analysed for percent inhibition by the following formula:

$$\frac{O.D. \text{ test well} - O.D. \text{ virus control}}{O.D. \text{ cell control} - O.D. \text{ virus control}} \times 100$$

The 50% effective concentration ($EC_{50}$) was calculated by the median effect equation (Chou, 1975,Proc. Int. Cong. Pharmacol. 6th p. 619) to determine the efficacy of compound. The 50% lethal concentration ($LC_{50}$) was calculated using uninfected MT4 cells.

Under these conditions, the following data were obtained (n =4 duplicate determinations:

TABLE 2

| Compound of Example | $IC_{50}$ ($\mu$M, 0% plasma) | $LC_{50}$ ($\mu$M) |
|---|---|---|
| 1P | 0.01 | 41.32 |
| 2B | 0.016 | 17.78 |
| 3C | 0.025 | 49.5 |
| 4F | 0.101 | >100 |
| 5 | 0.368 | >100 |
| 6F | 0.193 | >100 |
| 7B | 0.204 | >100 |
| 8 | 0.019 | 17.78 |
| 9B | 0.272 | 19.33 |
| 10F | 0.047 | 91.97 |
| 11B | 0.19 | 18.16 |
| 12B | 0.093 | 19.11 |
| 14D | 0.053 | >100 |
| 15 | 0.119 | >100 |
| 17C | 0.051 | 18.96 |
| 18C | 0.329 | 19.1 |
| 19E | 0.395 | 17.95 |
| 20D | 0.283 | 24.08 |
| 25E | 0.012 | 22.88 |
| 26H | 0.015 | 33.0 |
| 27D | 0.03 | 56.23 |
| 28 | 0.011 | 72.2 |
| 29C | 0.427 | 56 |
| 30B | 0.003 | 18 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include compounds wherein a hydroxyl group in the compound of this invention has been acylated with an N-protected or unprotected amino acid residue, a phosphate function, a hemisuccinate residue, an acyl residue of the formula R*C(O)— or R*C(S)— wherein R* is hydrogen, loweralkyl, haloalkyl, alkoxy, thioalkoxy, alkoxyalkyl, thioalkoxyalkyl or haloalkoxy, or an acyl residue of the formula Ra—C(Rb)(Rd)—C(O)— or Ra—C($R_b$)($R_d$)—C(S)— wherein $R_b$ and $R_d$ are independently selected from hydrogen or loweralkyl and $R_a$ is —N(Re)(Rf), $OR_e$ or —$SR_e$ wherein $R_e$ and $R_f$ are independently selected from hydrogen, loweralkyl and haloalkyl, or an amino-acyl residue of the formula $R_{180}NH(CH_2)_2NHCH_2C(O)$— or $R_{180}NH(CH_2)_2OCH_2C(O)$— wherein $R_{180}$ is hydrogen, loweralkyl, arylalkyl, cycloalkylalkyl, alkanoyl, benzoyl or an α-amino acyl group. The amino acid esters of particular interest are glycine and lysine; however, other amino acid residues can also be used, including those wherein the amino acyl group is —$C(O)CH_2NR_{200}R_{201}$ wherein $R_{200}$ and $R_{201}$ are independently selected from hydrogen and loweralkyl or the group —$NR_{200}R_{201}$ forms a nitrogen containing heterocyclic ring. These esters serve as pro-drugs of the compound of the present invention and serve to increase the solubility of these substances in the gastrointestinal tract. These esters also serve to increase solubility for intravenous administration of the compound. Other prodrugs include compounds wherein a hydroxyl group in the compound of this invention is functionalized with a substituent of the formula —$CH(R_g)OC(O)R_{181}$ or —$CH(R_g)OC(S)R_{181}$ wherein $R_{181}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in vivo to provide the compound of this invention. The preparation of the prodrug esters is carried out by reacting the compound of the invention with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl) esters, transacetalization with bis-(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 20 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology,* Volume XIV, Academic Press, New York, N.Y. (1976), p. 33 et seq.

Some preferred dosage forms for the compounds of this invention are disclosed in U.S. patent application Ser. No. 08/754,390, filed Nov. 21, 1996, in the names of J. Lipari, L. A. Al-Razzak, S. Ghosh and R. Gao and which is entitled Pharmaceutical Composition, which is incorporated herein by reference.

A preferred dosage form for the compounds of this invention comprises a solution of (a) a compound of the formula I in the amount of from about 1% to about 50% (preferably, from about 5% to about 30%) by weight of the total solution and (b) polyoxyl 35 castor oil in the amount of from about 0% to about 20% (preferably, from about 5% to about 10%) by weight of the total solution, in a pharmaceutically acceptable organic solvent which comprises (i) oleic acid in the amount of from about 20% to about 99% (preferably, from about 30% to about 70%; more preferably, from about 40% to about 65%) by weight of the total solution or (ii) a mixture of (1) oleic acid in the amount of from about 20% to about 99% (preferably, from about 30% to about 70%; more preferably, from about 40% to about 65%) by weight of the total solution and (2) ethanol or propylene glycol or a mixture thereof in the amount of from about 0% to about 12% (preferably, about 10%) by weight of the total solution. In an even more preferred embodiment of the invention, the solution is encapsulated in a soft elastic gelatin capsule (SEC) or a hard gelatin capsule.

A most preferred composition of the invention comprises a solution of (a) a compound of the formula I in the amount of about 30% by weight of the total solution and (b) polyoxyl 35 castor oil in the amount of about 10% by weight of the total solution, in a pharmaceutically acceptable organic solvent which comprises a mixture of (1) oleic acid in the amount of about 50% by weight of the total solution and (2) ethanol in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

An example of such a composition and its preparation is provided below.

| Component | % By Weight |
| --- | --- |
| compound of Example 2B (free base) | 30 |
| Ethanol (USP, 200 proof) | 10 |
| polyoxyl 35 castor oil (Cremophor ® EL) | 10 |
| Oleic acid, 6321, NF | 50 |
| Butylated hydroxy toluene (BHT), NF | 0.01 |

Preparation of the above composition:

The mixing tank was purged with nitrogen. Oleic acid (499.9 g) and ethanol (1 00 g) were mixed in the tank. The butylated hydroxytoluene (0.1 g) was charged into the tank and mixed until the solution was clear. The Compound of Example 2B (300 g) was slowly charged into the tank and mixed until the solution was clear. The polyoxyl 35 castor oil (100 g)was added to the tank and mixed. The resulting solution was filled into soft elastic capsules (0.333 g of solution/SEC) to provide a dosage of 100 mg of compound of Example 2B/SEC or 0.667 g/SEC to provide a dosage of 200 mg of compound of Example 2B/SEC.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, dideoxycytidine (ddC; zalcitabine), dideoxyinosine (ddI; didanosine), BCH-189, AzdU, carbovir, ddA, d4C, d4T (stavudine), 3TC (lamivudine) DP-AZT, FLT (fluorothymidine), BCH-189, 5-halo-3'-thiadideoxycytidine, PMEA, bis-POMPMEA, zidovudine (AZT), nevirapine, delavirdine, MSA-300, trovirdine and the like), non-nucleoside reverse transcriptase inhibitors (for example, R82193, L-697,661, Bl-RG-587 (nevirapine), retroviral protease inhibitors (for example, HIV protease inhibitors such as ritonavir, Ro 31-8959 (saquinavir), SC-52151, VX-478, AG1343 (nelfinavir), BMS 186,318, SC-55389a, BILA 1096 BS, DMP-323, DMP-450, KNI-227, KNI-272, U-1 40690, N-(2(R)-hydroxy-1 (S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (MK-639; indinavir), 5(S)-Boc-amino-4(S)-hydroxy-6-phenyl-2(R)-phenylmethylhexanoyl-(L)-Val-(L)-Phe-morpholin-4-ylamide, 1-Naphthoxyacetyl-beta-methylthio-Ala-(2S,3S)-3-amino-2-hydroxy-4-butanoyl-1,3-thiazolidine-4-t-butylamide (i.e., 1-Naphthoxyacetyl-Mta-(2S,3S)-AHPBA-Thz-NH-tBu), 5-isoquinolinoxyacetyl-beta-methylthio-Ala-(2S,3S)-3-amino-2-hydroxy-4-butanoyl-1,3-thiazolidine-4-t-butylamide (i.e., iQoa-Mta-Apns-Thz-NHtBu) and the like), HEPT compounds, L,697,639, R821 50, U-87201 E and the like), HIV integrase inhibitors (Zintevir and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-lgG, CD4-PE40, butyl-DNJ, hypericin, oxamyristic acid, dextran sulfate and pentosan polysulfate. Immunomodulators that can be administered in combination with the compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, cyclosporin, rapamycin, FK-565, FK-506, G-CSF, GM-CSF, hyperthermia, isopinosine, IVIG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with the compound of the present invention.

Other agents that can be used in combination with the compound of this invention are ansamycin LM 427, apurinic acid, ABPP, AI-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B1 2 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenytoin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for inhibition or treatment of HIV or AIDS in combination with the compound of this invention are reverse transcriptase inhibitors, especially, AZT (zidovudine), ddl (didanosine), ddC (zalcitabine), d4T (stavudine), 3TC (lamivudine), nevirapine, delavirdine, trovirdine, PMEA, bis-POMPMEA and MSA-300.

Other preferred agents for inhibition or treatment of HIV or AIDS in combination with the compound of this invention are HIV protease inhibitors, especially, ABT-538 (ritonavir) and related compounds, disclosed in U.S. Pat. No. 5,541,206, issued Jul. 30, 1996 and U.S. Pat. No. 5,491,253, issued February 13, 1996 which are both incorporated by reference herein, N-(2(R)-hydroxy-1 (S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (i.e., indinavir) and related compounds, disclosed in European Patent Application No. EP541168, published May 12, 1993, and U.S. Pat. No. 5,413,999, issued May 9, 1995 which are both incorporated herein by reference; N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (i.e., saquinavir) and related compounds, disclosed in U.S. Pat. No. 5,196,438, issued March 23, 1993, which is incorporated herein by reference; 5(S)-Boc-amino-4(S)-hydroxy-6-phenyl-2(R)-phenylmethylhexanoyl-(L)-Val-(L)-Phe-morpholin-4-ylamide and related compounds, disclosed in European Patent Application No. EP532466, published Mar. 17, 1993, which is incorporated herein by reference; 1-Naphthoxyacetyl-beta-methylthio-Ala-(2S,3S)-3-amino-2-hydroxy-4-butanoyl-1,3-thiazolidine-4-t-butylamide (i.e., 1-Naphthoxyacetyl-Mta-(2S,3S)-AHPBA-Thz-NH-tBu), 5-isoquinolinoxyacetyl-beta-methylthio-Ala-(2S,3S)-3-amino-2-hydroxy-4-butanoyl-1,3-thiazolidine-4-t-butylamide (i.e., iQoa-Mta-Apns-Thz-NHtBu) and related compounds, disclosed in European Patent Application No. EP490667, published Jun. 17,1992 and Chem. Pharm. Bull. 40 (8) 2251 (1992), which are both incorporated herein by reference; [1S[1R*(R*),2S*]]-$N^1$[3-[[[(1,1-dimethylethyl)amino]carbonyl]($^2$-methylpropyl)amino]-2-hydroxy-1-(phenylmethyl)propyl]-2-[($^2$-quinolinylcarbonyl)amino]-butanediamide (i.e., SC-52151) and related compounds, disclosed in PCT Patent Application No. WO92/08701, published May 29, 1992 and PCT Patent Application No. WO93/23368, published Nov. 25, 1993, both of which are incorporated herein by reference;

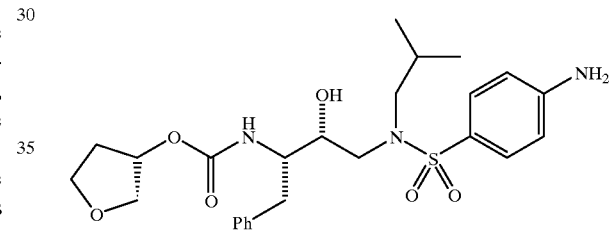

(i.e., VX-478) and related compounds, disclosed in PCT Patent Application No. WO94/05639, published Mar. 17, 1994, which is incorporated herein by reference

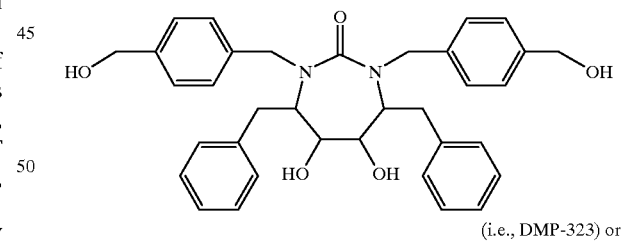

(i.e., DMP-323) or

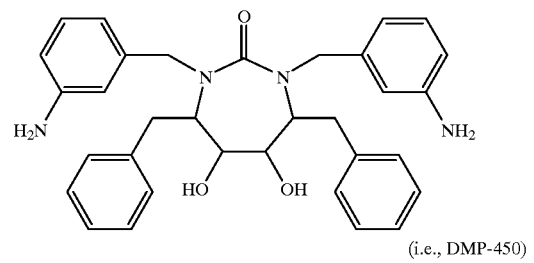

(i.e., DMP-450)

and related compounds, disclosed in PCT Patent Application No. WO93/07128, published Apr. 15, 1993, which is incorporated herein by reference;

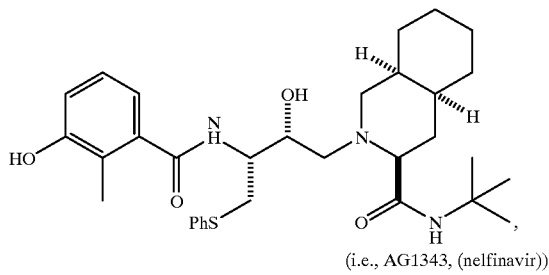

(i.e., AG1343, (nelfinavir))

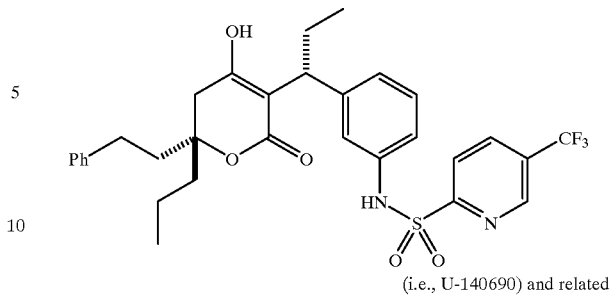

(i.e., U-140690) and related disclosed in PCT Patent Application No. WO95/09843, published Apr. 13, 1995 and U.S. Pat. No. 5,484,926, issued Jan. 16, 1996, which are both incorporated herein by reference;

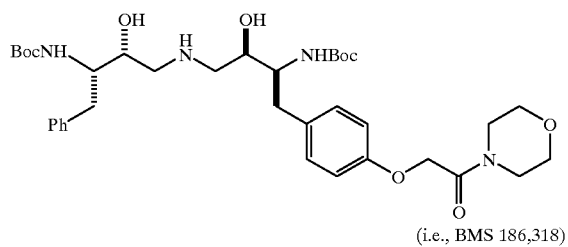

(i.e., BMS 186,318)

disclosed in European Patent Application No. EP580402, published Jan. 26, 1994, which is incorporated herein by reference;

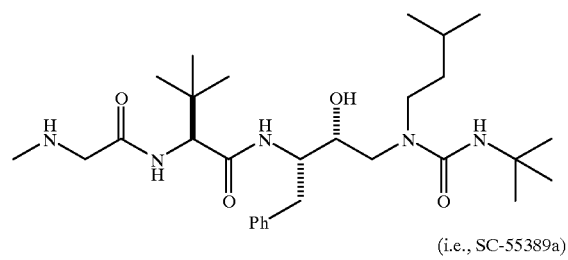

(i.e., SC-55389a)

disclosed at 2nd National Conference on Human Retroviruses and Related Infections, (Washington, D.C., Jan. 29–Feb. 2, 1995), Session 88; and

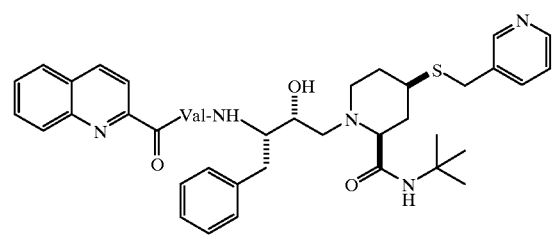

(i.e., BILA 1096 BS) and related compounds disclosed in European Patent Application No. EP560268, published Sep. 15, 1993, which is incorporated herein by reference; and compounds disclosed in PCT Patent Application No. WO 9530670, published Nov. 16, 1995, which is incorporated herein by reference; or a pharmaceutically acceptable salt of any of the above.

In a most preferred combination, a compound of this invention is administered in combination with ritonavir. Such a combination is especially useful for inhibiting HIV protease in a human. Such a combination is also especially useful for inhibiting or treating an HIV infection in a human. When used in such a combination the compound of this invention and ritonavir can be administered as separate agents at the same or different times or they can be formulated as a single composition comprising both compounds.

When administered in combination with a compound of this invention, ritonavir causes an improvement in the pharmacokinetics (i.e., increases half-life, increases the time to peak plasma concentration, increases blood levels) of the compound of this invention.

Preferred dosage forms for ritonavir include (a) a liquid dosage form for oral administration as disclosed in U.S. Pat. No. 5,484,801, issued Jan. 19, 1996, which is incorporated herein by reference, (b) an encapsulated solid or semi-solid dosage form as disclosed in PCT Patent Application No. WO95/07696, published Mar. 23, 1995 and U.S. Ser. No. 08/402,690, filed Mar. 13,1995, both of which are incorporated herein by reference and (c) an encapsulated solid dosage form as disclosed in PCT Patent Application No. WO95/09614, published Apr. 13, 1995 and U.S. Pat. No. 5,559,158, issued Sep. 24, 1996, both of which are incorporated herein by reference.

Other examples of preferred dosage forms for ritonavir are disclosed in U.S. patent application Ser. No. 08/754,390, filed Nov. 21, 1996, in the names of J. Lipari, L. A. Al-Razzak, S. Ghosh and R. Gao and which is entitled Pharmaceutical Composition, which is incorporated herein by reference.

A preferred composition for ritonavir comprises a solution of (a) ritonavir in the amount of from about 1% to about 30% (preferably, from about 5% to about 25%) by weight of the total solution and (b) polyoxyl 35 castor oil in the amount of from about 0% to about 20% (preferably, from about 5% to about 10%) by weight of the total solution, in a pharmaceutically acceptable organic solvent which comprises (i) oleic acid in the amount of from about 15% to abo.'t 99% (preferably, from about 30% to about 70%; more preferably, from about 40% to about 65%) by weight of the total solution or (ii) a mixture of (1) oleic acid in the amount of from about 15% to about 99% (preferably, from about 30% to about 70%; more preferably, from about 40% to about 65%) by weight of the total solution and (2) ethanol or propylene glycol or a mixture thereof in the amount of from about 0% to about 12% (preferably, about 10%) by weight of the total solution. In an even more preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01% to about 0.08% by weight of the total solution (preferably, from about 0.01% to about 0.05% by weight of the total solution).

Examples of such a composition and its preparation are provided below.

| Component | % By Weight |
| --- | --- |
| ritonavir (free base) | 20 |
| Ethanol (USP, 200 proof) | 10 |
| polyoxyl 35 castor oil (Cremophor ® EL) | 5 |
| Oleic acid, 6321, NF | 65 |
| Butylated hydroxy toluene (BHT), NF | 0.01 |

Preparation of the above composition:

The mixing tank was purged with nitrogen. Oleic acid (649.9 g) and ethanol (100 g) were mixed in the tank. This solution was warmed to about 33° C. (29–37° C.) and maintained at that temperature. The butylated hydroxytoluene (0.1 g) was charged into the tank and mixed until the solution was clear. The ritonavir (200 g) was slowly charged into the tank and mixed until the solution was clear. The polyoxyl 35 castor oil (50 g) was added to the tank and mixed. Heating was discontinued and the solution allowed to cool to amibient temperature (20–30° C.). The resulting solution was filled into soft elastic capsules (0.5 g of solution/SEC) to provide a dosage of 100 mg of ritonavir/SEC or 1.0 g/SEC to provide a dosage of 200 mg of ritonavir/SEC.

| Component | % By Weight |
| --- | --- |
| ritonavir (free base) | 20 |
| Ethanol (USP, 200 proof) | 10 |
| polyoxyl 35 castor oil (Cremophor ® EL) | 10 |
| Oleic acid, 6321, NF | 60 |
| Butylated hydroxy toluene (BHT), NF | 0.01 |

Preparation of the above composition:

The mixing tank was purged with nitrogen. Oleic acid (599.9 g) and ethanol (100 g) were mixed in the tank. This solution was warmed to about 33° C. (29–37° C.) and maintained at that temperature. The butylated hydroxytoluene (0.1 g) was charged into the tank and mixed until the solution was clear. The ritonavir (200 g) was slowly charged into the tank and mixed until the solution was clear. The polyoxyl 35 castor oil (100 g)was added to the tank and mixed. Heating was discontinued and the solution allowed to cool to amibient temperature (20–30° C.). The resulting solution was filled into soft elastic capsules (0.5 g of solution/SEC) to provide a dosage of 100 mg of ritonavir/SEC or 1.0 g/SEC to provide a dosage of 200 mg of ritonavir/SEC.

Examples of preferred single dosage forms comprising both ritonavir and a compound of the formula I are also disclosed in U.S. Patent Application No. 08/754,390, filed November 21, 1996, in the names of J. Lipari, L. A. Al-Razzak, S. Ghosh and R. Gao and which is entitled Pharmaceutical Composition, which is incorporated herein by reference.

A preferred composition for a single dosage form comprising both ritonavir and a compound of the formula I comprises a solution of (a) a mixture of ritonavir in the amount of from about 1% to about 30% (preferably, from about 5% to about 25%) by weight of the total solution and a compound of the formula I in the amount of from about 1% to about 50% (preferably, from about 5% to about 43%) by weight of the total solution and (b) polyoxyl 35 castor oil in the amount of about 10% by weight of the total solution, in a pharmaceutically acceptable organic solvent which comprises a mixture of (1) oleic acid in the amount of from about 10% to about 88% (preferably, from about 40% to about 65%) by weight of the total solution and (2) ethanol in the amount of about 10% by weight of the total solution. In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of from about 0.01 % to about 0.08% by weight of the total solution (preferably, from about 0.01% to about 0.05% by weight of the total solution).

Examples of such a composition and its preparation are provided below.

| Component | % By Weight |
| --- | --- |
| ritonavir (free base) | 5 |
| compound of Example 2B (free base) | 30 |
| Ethanol (USP, 200 proof) | 10 |
| polyoxyl 35 castor oil (Cremophor ® EL) | 10 |
| Oleic acid, 6321, NF | 45 |
| Butylated hydroxy toluene (BHT), NF | 0.01 |
| ritonavir (free base) | 15 |
| compound of Example 2B (free base) | 15 |
| Ethanol (USP, 200 proof) | 10 |
| polyoxyl 35 castor oil (Cremophor ® EL) | 10 |
| Oleic acid, 6321, NF | 10 |
| Butylated hydroxy toluene (BHT), NF | 0.01 |
| ritonavir (free base) | 15 |
| compound of Example 2B (free base) | 15 |
| Ethanol (USP, 200 proof) | 10 |
| polyoxyl 35 castor oil (Cremophor ® EL) | 5 |
| Oleic acid, 6321, NF | 55 |
| Butylated hydroxy toluene (BHT), NF | 0.01 |

Preparation of the above composition:

The mixing tank was purged with nitrogen. Oleic acid (549.9 9) and ethanol (100 g) were mixed in the tank. The butylated hydroxytoluene (0.1 g) was charged into the tank and mixed until the solution was clear. The ritonavir (150 g) was slowly charged into the tank and mixed until the solution was clear. Compound Example 2B (150 g) was slowly charged into the tank and mixed until the solution was clear. The polyoxyl 35 castor oil (100 g) was added to the tank and mixed. The resulting solution was filled into soft elastic capsules (1.0 g of solution/SEC) to provide a dosage of 150 mg each of ritonavir and compound Example 2B/SEC.

| Component | % By Weight |
| --- | --- |
| ritonavir (free base) | 15 |
| compound of Example 2B (free base) | 5 |
| Ethanol (USP, 200 proof) | 10 |
| polyoxyl 35 castor oil (Cremophor ® EL) | 10 |

-continued

| Component | % By Weight |
|---|---|
| Oleic acid, 6321, NF | 60 |
| Butylated hydroxy toluene (BHT), NF | 0.01 |

Total daily dose of ritonavir (administered in combination with a compound of this invention) to be administered to a human or other mammal host in single or divided doses may be in amounts, for example, from 0.001 to 300 mg/kg body weight daily and more usually 0.1 to 10 mg of ritonavir. Dosage unit compositions may contain such amounts of submultiples thereof to make up the daily dose.

In the compositions which comprise a mixture of ritonavir and the compound of Example 2B, the ratio (w/w) of ritonavir to the compound of Example 2B ranges from about 1:16 to about 5:1 (preferably, from about 1:6 to about 3:1).

In another most preferred combination, a compound of this invention is administered in combination with ritonavir and one or more reverse transcriptase inhibitors (preferably, one or more compounds selected from the group consisting of AZT (zidovudine), ddI (didanosine), ddC (zalcitabine), d4T (stavudine) and 3TC (lamivudine)). Such a combination is especially useful for inhibiting or treating an HIV infection in a human. When used in such a combination the compound of this invention and ritonavir and one or more reverse transcriptase inhibitors can be administered as separate agents at the same or different times or they can be formulated as compositions comprising two or more of the compounds. A particularly preferred therapeutic combination comprises a compound of the formula I (especially, the compound of Example 2B) in combination with ritonavir, AZT and 3TC.

It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for inhibiting an HIV infection comprising administering to a human in need of such treatment a therapeutically effective combination of a compound of the formula:

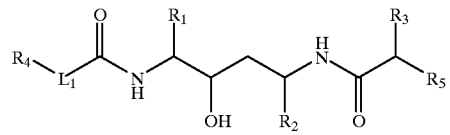

wherein $R_1$ and $R_2$ are independently selected from the group consisting of loweralkyl, cycloalkylalkyl and arylalkyl;

$R_3$ is loweralkyl, hydroxyalkyl or cycloalkylalkyl;

$R_4$ is aryl or heterocyclic;

$R_5$ is a) 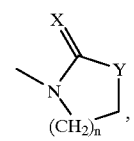

b) 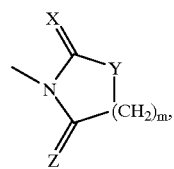

c) 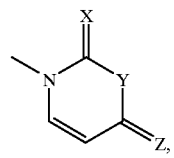

d) 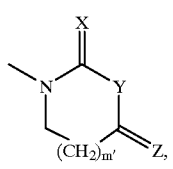

e) 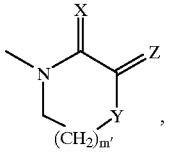

f) 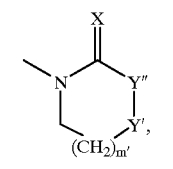

g) 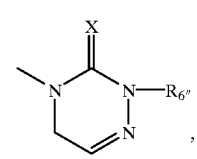

-continued h)

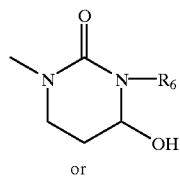

or i)

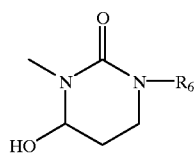

wherein n is 1, 2 or 3, m is 1, 2 or 3, m' is 1 or 2, X is O, S or NH, Y is —$CH_2$—, —O—, —S—or —N($R_6$)— wherein $R_6$ is hydrogen, loweralkyl, cycloalkyl, cycloalkylalkyl, aryl or arylalkyl, Y" is —$CH_2$— or —N($R_{6''}$)— wherein $R_{6''}$ is hydrogen, loweralkyl, cycloalkyl, cycloalkylalkyl, aryl or arylalkyl, Y' is —N($R_{6'}$)— wherein $R_{6'}$ is hydrogen, loweralkyl, cycloalkyl, cycloalkylalkyl, aryl or arylalkyl, and Z is O, S or NH; and $L_1$ is
a) —O—,
b) —S—,
c) —N($R_7$)— wherein $R_7$ is hydrogen, loweralkyl, cycloalkyl or cycloalkylalkyl,
d) —O-alkylenyl-,
e) —S-alkylenyl-,
f) —S(O)-alkyleneyl-,
g) —S(O)$_2$-alkylenyl-,
h) —N($R_7$)-alkylenyl- wherein $R_7$ is defined as above,
i) -alkylenyl—O—,
j) -alkylenyl—S—,
k) -alkylenyl-N($R_7$)— wherein $R_7$ is defined as above,
l) alkylenyl or
m) alkenylenyl;
or a pharmaceutically acceptable salt, ester or prodrug thereof, and a reverse transcriptase inhibitor or a combination of reverse transcriptase inhibitors.

2. The method of claim 1 wherein the reverse transcriptase inhibitor is selected from the group consisting of 5-halo-3'-thia-dideoxycytidine, AZT (zidovudine), ddI (didanosine), ddC (zalcitabine), d4T (stavudine), 3TC (lamivudine), nevirapine, delavirdine, trovirdine, PMEA, bis-POMPMEA, MSA-300 and combinations of two or more thereof.

3. A method for inhibiting an HIV infection comprising administering to a human in need of such treatment a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane, or a pharmaceutically acceptable salt, ester or prodrug thereof and a reverse transcriptase inhibitor or a combination of reverse transcriptase inhibitors.

4. The method of claim 3 wherein the reverse transcriptase inhibitor is selected from the group consisting of 5-halo-3'-thia-dideoxycytidine, AZT (zidovudine), ddI (didanosine), ddC (zalcitabine), d4T (stavudine), 3TC (lamivudine), nevirapine, delavirdine , trovirdine, PMEA, bis-POMPMEA, MSA-300 and combinations of two or more thereof.

5. A method for inhibiting an HIV infection comprising administering to a human in need of such treatment a therapeutically effective combination of a compound of the formula:

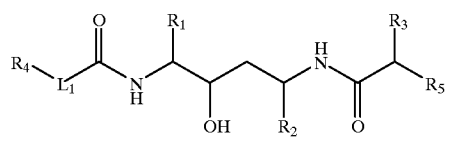

I wherein $R_1$ and $R_2$ are independently selected from the group consisting of loweralkyl, cycloalkylalkyl and arylalkyl;
$R_3$ is loweralkyl, hydroxyalkyl or cycloalkylalkyl;
$R_4$ is aryl or heterocyclic;
$R_5$ is a)

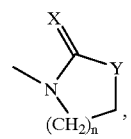

b)

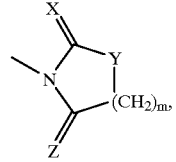

c)

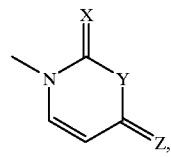

d)

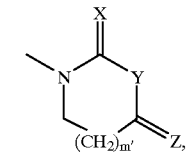

e)

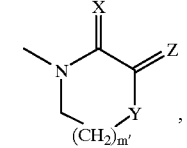

f)

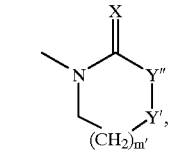

-continued g) 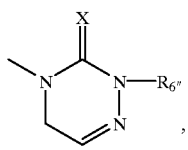, h) 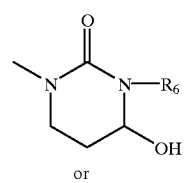 or i) 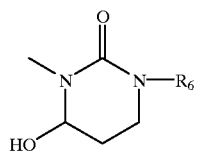

wherein n is 1, 2 or 3, m is 1, 2 or 3, m' is 1 or 2, X is O, S or NH, Y is —CH$_2$—, —O—, —S— or —N(R$_6$)— wherein R$_6$ is hydrogen, loweralkyl, cycloalkyl, cycloalkylalkyl, aryl or arylalkyl, Y" is —CH$_2$— or —N(R$_{6''}$)— wherein R$_6$ is hydrogen, loweralkyl, cycloalkyl, cycloalkylalkyl, aryl or arylalkyl, Y' is —N(R$_{6'}$)— wherein R$_6$ is hydrogen, loweralkyl, cycloalkyl, cycloalkylalkyl, aryl or arylalkyl, and Z is O, S or NH; and L$_1$ is
a) —O—,
b) —S—,
c) —N(R$_7$)— wherein R$_7$ is hydrogen, loweralkyl, cycloalkyl or cycloalkylalkyl,
d) —O-alkylenyl-,
e) —S—alkylenyl-,
f) —S(O)-alkyleneyl-,
g) —S(O)$_2$-alkylenyl-,
h) —N(R$_7$)-alkylenyl- wherein R$_7$ is defined as above,
i) -alkylenyl-O—,
j) -alkylenyl-S—,
k) -alkylenyl-N(R$_7$)— wherein R$_7$ is defined as above,
l) alkylenyl or
m) alkenylenyl;

or a pharmaceutically acceptable salt, ester or prodrug thereof, and another HIV protease inhibitor or a combination of other HIV protease inhibitors.

6. The method of claim 5 wherein the other HIV protease inhibitor is selected from the group consisting of ritonavir, saquinavir, indinavir, 5(S)-Boc-amino-4(S)-hydroxy-6-phenyl-2(R)-phenylmethylhexanoyl-(L)-Val-(L)-Phe-morpholin-4-ylamide;

1-Naphthoxyacetyl-beta-methylthio-Ala-(2S,3S)-3-amino-2-hydroxy-4-butanoyl-1,3-thiazolidine-4-t-butyiamide;

5-isoquinolinoxyacetyl-beta-methylthio-Ala-(2S,3S)-3-amino-2-hydroxy-4-butanoyl-1,3-thiazolidine-4-t-butylamide;

(1S-(1R*(R*),2S*)}-N$^1$(3-((((1,1-dimethylethyl)amino) carbonyl)(2-methyipropyl)amino)-2-hydroxy-1-(phenylmethyl)propyl)-2-((2-quinolinylcarbonyl)amino)-butanediamide;

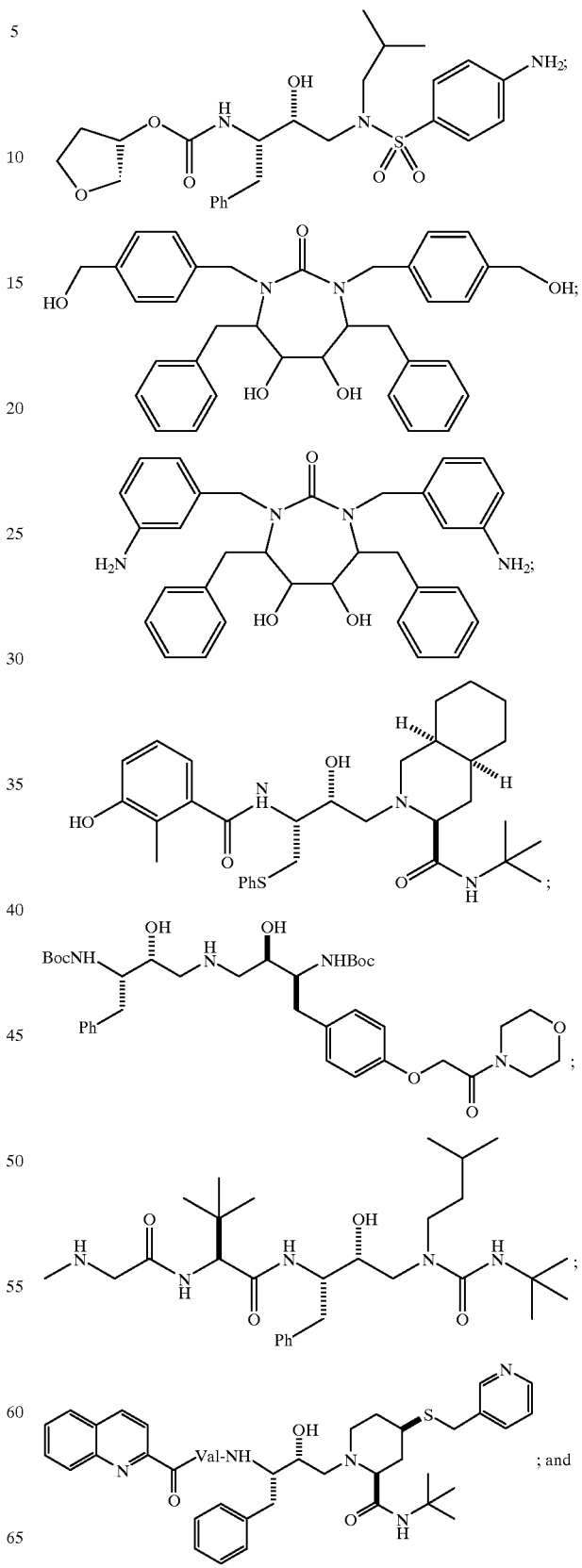

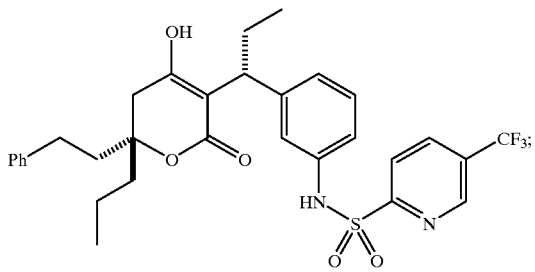

or a pharmaceutically acceptable salt thereof, or a combination of two or more of these HIV protease inhibitors.

7. A method for inhibiting an HIV infection comprising administering to a human in need of such treatment a therapeutically effective combination of the compound (2S, 3S,5S)-2-(2,6-dimethylphenoxyacetyl)amino-3-hydroxy-5-(2S-(1-tetrahydro-pyrimid-2-onyl)-3-methylbutanoyl) amino-1,6-diphenylhexane, or a pharmaceutically acceptable salt, ester or prodrug thereof and another HIV protease inhibitor or a combination of other HIV protease inhibitors.

8. The method of claim 7 wherein the other HIV protease inhibitor is selected from the group consisting of ritonavir, saquinavir, indinavir, 5(S)-Boc-amino-4(S)-hydroxy-6-phenyl-2(R)-phenylmethylhexanoyl-(L)-Val-(L)-Phe-morpholin-4-ylamide;
1-Naphthoxyacetyl-beta-methylthio-Ala-(2S,3S)-3-amino-2-hydroxy-4-butanoyl-1,3-thiazolidine-4-t-butylamide;
5-isoquinolinoxyacetyl-beta-methylthio-Ala-(2S,3S)-3-amino-2-hydroxy-4-butanoyl-1,3-thiazolidine-4-t-butylamide;
(1S-(1R*(R*),2S*)}-N$^1$(3-((((1,1-dimethylethyl)amino) carbonyl)(2-methylpropyl)amino)-2-hydroxy-1-(phenylmethyl)propyl)-2-((2-quinolinylcarbonyl)amino)-butanediamide;

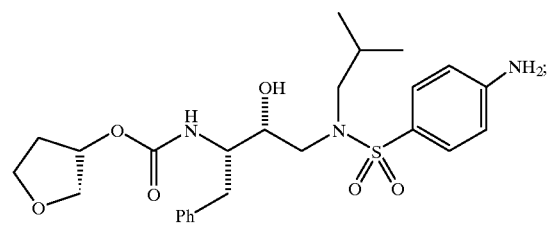

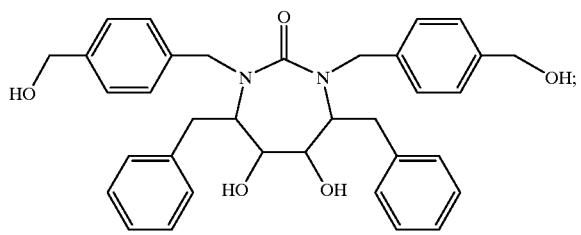

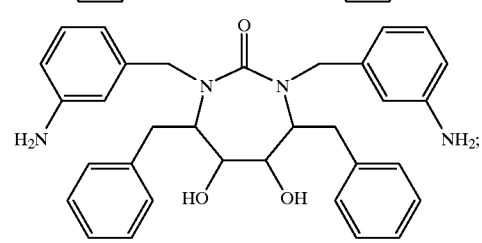

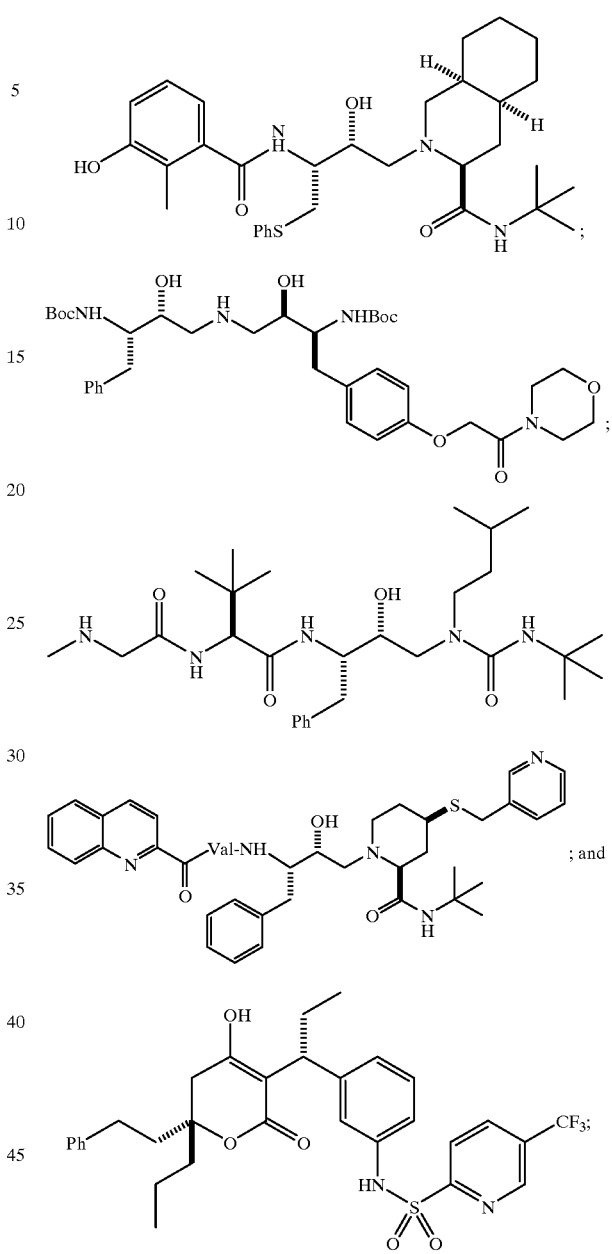

or a pharmaceutically acceptable salt thereof, or a combination of two or more of these HIV protease inhibitors.

9. A method for inhibiting an HIV infection comprising administering to a human in need of such treatment a therapeutically effective combination of the compound (2S, 3S,5S)-2-(2,6-dimethylphenoxyacetyl)amino-3-hydroxy-5-(2S-(1-tetrahydro-pyrimid-2-onyl)-3-methylbutanoyl) amino-1,6-diphenylhexane, or a pharmaceutically acceptable salt, ester or prodrug thereof and ritonavir or a pharmaceutically acceptable salt thereof.

10. A method for inhibiting an HIV infection comprising administering to a human in need of such treatment a therapeutically effective combination of a compound of the formula:

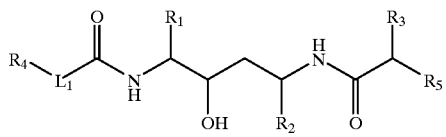

wherein $R_1$ and $R_2$ are independently selected from the group consisting of loweralkyl, cycloalkylalkyl and arylalkyl;

$R_3$ is loweralkyl, hydroxyalkyl or cycloalkylalkyl;
$R_4$ is aryl or heterocyclic;
$R_5$ is a) 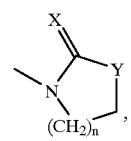

b) 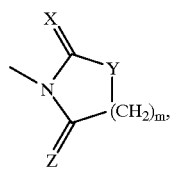

c) 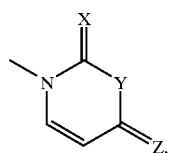

d) 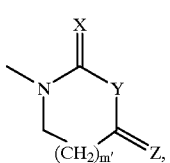

e) 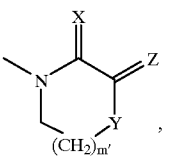

f) 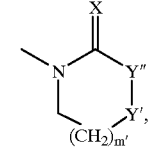

g) 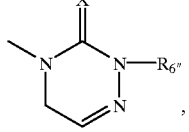

h) 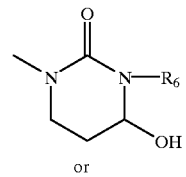

or i) 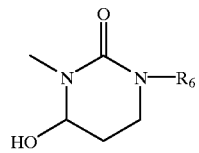

wherein n is 1, 2 or 3, m is 1, 2 or 3, m' is 1 or 2, X is O, S or NH, Y is —$CH_2$—, —O—, —S— or —N($R_6$)— wherein $R_6$ is hydrogen, loweralkyl, cycloalkyl, cycloalkylalkyl, aryl or arylalkyl, Y" is —$CH_2$— or —N($R_{6"}$)— wherein $R_{6"}$ is hydrogen, loweralkyl, cycloalkyl, cycloalkylalkyl, aryl or arylalkyl, Y' is —N($R_{6"}$)— wherein $R_{6"}$ is hydrogen, loweralkyl, cycloalkyl, cycloalkylalkyl, aryl or arylalkyl, and Z is O, S or NH; and $L_1$ is
a) —O—,
b) —S—,
c) —N($R_7$)— wherein $R_7$ is hydrogen, loweralkyl, cycloalkyl or cycloalkylalkyl,
d) —O-alkylenyl-,
e) —S-alkylenyl-,
f) —S(O)-alkyleneyl-,
g) —S(O)$_2$-alkylenyl-,
h) —N($R_7$)-alkylenyl- wherein $R_7$ is defined as above,
i) -alkylenyl-O—,
j) -alkylenyl-S—,
k) -alkylenyl-N($R_7$)— wherein $R_7$ is defined as above,
l) alkylenyl or
m) alkenylenyl;

or a pharmaceutically acceptable salt, ester or prodrug thereof, and another HIV protease inhibitor or a combination of other HIV protease inhibitors and a reverse transcriptase inhibitor or a combination of reverse transcriptase inhibitors.

11. The method according to claim 10 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl)amino-1,6-diphenylhexane;
or a pharmaceutically acceptable salt, ester or prodrug thereof.

12. The method according to claim 10 wherein said compound of formula I is (2S,3S,5S)-2-(2,6-dimethylphenoxyacetyl) amino-3-hydroxy-5-(2S-(1-tetrahydro-pyrimid-2-onyl) -3-methyl butanoyl)amino-1,6-diphenylhexane.

13. The method according to claim 10 wherein said other HIV protease inhibitor is selected from the group consisting of ritonavir, saquinavir, VX-478, U-140690, nelfinavir and combinations of two or more thereof, or a pharmaceutically acceptable salt thereof.

14. The method according to claim 12 wherein said other HIV protease inhibitor is ritonavir.

15. The method according to claim 10 wherein said reverse transcriptase inhibitor is selected from the group consisting of 5-halo-3'-thia-dideoxycytidine, AZT (zidovudine), ddI (didanosine), ddC (zalcitabine), d4T (stavudine), 3TC (lamivudine), nevirapine, delavirdine, trovirdine, PMEA, bis-POMPMEA, MSA-300, and combinations of two or more thereof.

16. The method according to claim 15 wherein said reverse transcriptase inhibitor is selected from the group consisting of 5-halo-3'-thia-dideoxycytidine, AZT (zidovudine), 3TC (lamivudine), and d4T (stavudine).

17. The method according to claim 15 wherein said reverse transcriptase inhibitor is 5-halo-3'-thia-dideoxycytidine.

18. The method according to claim 15 wherein said reverse transcriptase inhibitor is 3TC (lamivudine).

19. The method according to claim 15 wherein said reverse transcriptase inhibitor is d4T (stavudine).

20. The method according to claim 15 wherein said reverse transcriptase inhibitor is nevirapine.

21. The method according to claim 15 wherein said reverse transcriptase inhibitor is delavirdine.

22. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane,
or a pharmaceutically acceptable salt, ester or prodrug thereof, said other HIV protease inhibitor is ritonavir, and said reverse transcriptase inhibitor is 5-halo-3'-thia-dideoxycytidine.

23. The method according to claim 15 wherein said compound of formula I is (2S,3S,5S)-2-(2,6-dimethylphenoxyacetyl) amino-3-hydroxy-5-(2S-(l-tetrahydro-pyrimid-2-onyl)-3-methyl butanoyl)amino-1,6-diphenylhexane,
or a pharmaceutically acceptable salt, ester or prodrug thereof, said other HIV protease inhibitor is ritonavir, and said reverse transcriptase inhibitor is 3TC (lamivudine).

24. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane,
or a pharmaceutically acceptable salt, ester or prodrug thereof, said other HIV protease inhibitor is ritonavir, and said reverse transcriptase inhibitor is d4T (stavudine).

25. The method according to claim 15 wherein said compound of formula I is (2S,3S,5S)-2-(2,6-dimethylphenoxyacetyl) amino-3-hydroxy-5-(2S-(l-tetrahydro-pyrimid-2-onyl)-3-methyl butanoyl)amino-1,6-diphenylhexane,
or a pharmaceutically acceptable salt, ester or prodrug thereof, said other HIV protease inhibitor is ritonavir, and said reverse transcriptase inhibitor is nevirapine.

26. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl)amino-1,6-diphenylhexane,
or a pharmaceutically acceptable salt, ester or prodrug thereof, said other HIV protease inhibitor is ritonavir, and said reverse transcriptase inhibitor is delavirdine.

27. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl)amino-1,6-diphenylhexane,
said other HIV protease inhibitor is ritonavir, and said reverse transcriptase inhibitor is 5-halo-3'-thia-dideoxycytidine.

28. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane,
said other HIV protease inhibitor is ritonavir, and said reverse transcriptase inhibitor is 3TC (lamivudine).

29. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane,
said other HIV protease inhibitor is ritonavir, and said reverse transcriptase inhibitor is d4T (stavudine).

30. The method according to claim 15 wherein said compound of formula I is (2S,3S,5S)-2-(2,6-dimethylphenoxyacetyl) amino-3-hydroxy-5-(2S-(l-tetrahydro-pyrimid-2-onyl)-3-methyl butanoyl)amino-1,6-diphenylhexane,
said other HIV protease inhibitor is ritonavir, and said reverse transcriptase inhibitor is nevirapine.

31. The method according to claim 15 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl)amino-1,6-diphenylhexane,
said additional HIV protease inhibitor is ritonavir, and said reverse transcriptase inhibitor is delavirdine.

32. A pharmaceutical composition comprising a pharmaceutical carrier and therapeutically effective combination of a compound of the formula:

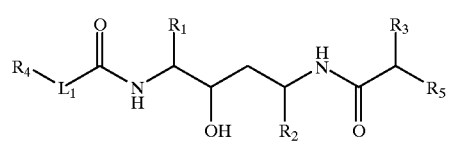

I wherein $R_1$ and $R_2$ are independently selected from the group consisting of loweralkyl, cycloalkylalkyl and arylalkyl;

$R_3$ is loweralkyl, hydroxyalkyl or cycloalkylalkyl;

$R_4$ is aryl or heterocyclic;

a)

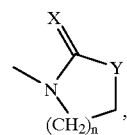

b)

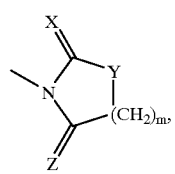

c) 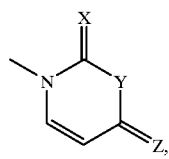

d) 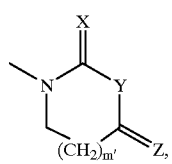

e) 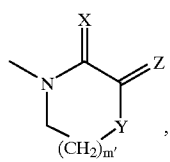

f) 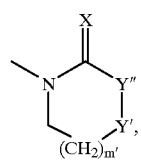

g) 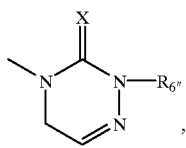

h) 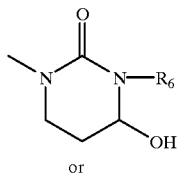

or i) 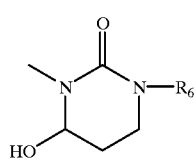

wherein n is 1, 2 or 3, m is 1, 2 or 3, m' is 1 or 2, X is O, S or NH, Y is —$CH_2$—, —O—, —S— or —N($R_6$)— wherein $R_6$ is hydrogen, loweralkyl, cycloalkyl, cycloalkylalkyl, aryl or arylalkyl, Y" is —$CH_2$— or —N($R_{6"}$)— wherein $R_{6"}$ is hydrogen, loweralkyl, cycloalkyl, cycloalkylalkyl, aryl or arylalkyl, Y' is —N($R_{6'}$)— wherein $R_{6'}$ is hydrogen, loweralkyl, cycloalkyl, cycloalkylalkyl, aryl or arylalkyl, and Z is O, S or NH; and $L_1$ is a) —O—,
b) —S—,
c) —N($R_7$)— wherein $R_7$ is hydrogen, loweralkyl, cycloalkyl or cycloalkylalkyl,
d) —O-alkylenyl-,
e) —S-alkylenyl-,
f) —S(O)-alkyleneyl-,
g) —S(O)$_2$-alkylenyl-,
h) —N($R_7$)-alkylenyl- wherein $R_7$ is defined as above,
i) -alkylenyl-O—,
j) -alkylenyl-S—,
k) -alkylenyl-N($R_7$)— wherein $R_7$ is defined as above,
l) alkylenyl or
m) alkenylenyl;

or a pharmaceutically acceptable salt, ester or prodrug thereof, and another HIV protease inhibitor or a combination of other HIV protease inhibitors.

33. A pharmaceutical composition comprising a pharmaceutical carrier and therapeutically effective combination of a compound of the formula:

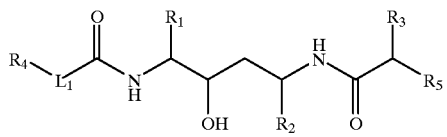

I wherein $R_1$ and $R_2$ are independently selected from the group consisting of loweralkyl, cycloalkylalkyl and arylalkyl;

$R_3$ is loweralkyl, hydroxyalkyl or cycloalkylalkyl;
$R_4$ is aryl or heterocyclic;
$R_5$ is a) 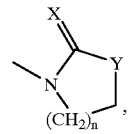

b) 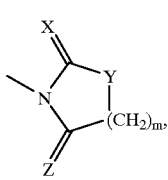

c) 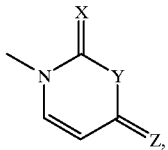

d) 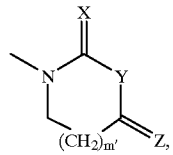

-continued e) 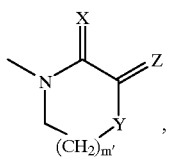

f) 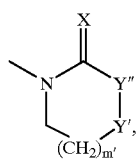

g) 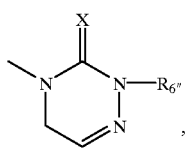

h) 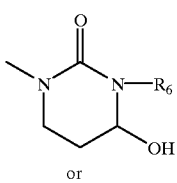

or i) 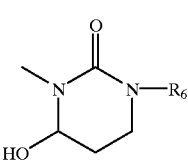

wherein n is 1, 2 or 3, m is 1, 2 or 3, m' is 1 or 2, X is O, S or NH, Y is —CH$_2$—, —O—, —S— or —N(R$_6$)— wherein R$_6$ is hydrogen, loweralkyl, cycloalkyl, cycloalkylalkyl, aryl or arylalkyl, Y" is —CH$_2$— or —N(R$_{6''}$)— wherein R$_{6''}$ is hydrogen, loweralkyl, cycloalkyl, cycloalkylalkyl, aryl or arylalkyl, Y' is —N(R$_{6'}$)— wherein R$_{6'}$ is hydrogen, loweralkyl, cycloalkyl, cycloalkylalkyl, aryl or arylalkyl, and Z is O, S or NH; and L$_1$ is a) —O—,
b) —S—, 1
c) —N(R$_7$)— wherein R$_7$ is hydrogen, loweralkyl, cycloalkyl or cycloalkylalkyl,
d) —O-alkylenyl-,
e) —S-alkylenyl-,
f) —S(O)-alkyleneyl-,
g) —S(O)$_2$-alkylenyl-,
h) —N(R$_7$)-alkylenyl- wherein R$_7$ is defined as above,
i) -alkylenyl-O—,
j) -alkylenyl—S—,
k) -alkylenyl-N(R$_7$)— wherein R$_7$ is defined as above,
l) alkylenyl or
m) alkenylenyl;

or a pharmaceutically acceptable salt, ester or prodrug thereof, and a reverse transcriptase inhibitor or a combination of reverse transcriptase inhibitors.

34. The pharmaceutical composition according to claim 32 which further comprises a reverse transcriptase inhibitor or a combination of reverse transcriptase inhibitors.

35. The pharmaceutical composition according to claim 32 wherein said compound of formula I is (2S,3S,5S)-2-(2,6-dimethylphenoxyacetyl)amino-3-hydroxy-5-(2S-(1-tetrahydro-pyrimid-2-onyl)-3-methyl butanoyl) amino-1,6-diphenylhexane, or a pharmaceutically acceptable salt, ester or prodrug thereof.

36. The pharmaceutical composition according to claim 32 wherein said compound of formula I is (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane.

37. The pharmaceutical composition according to claim 34 wherein said other HIV protease inhibitor is ritonavir.

38. The pharmaceutical composition according to claim 34 wherein said reverse transcriptase inhibitor is 5-halo-3'-thia-dideoxycytidine.

39. The pharmaceutical composition according to claim 34 wherein said reverse transcriptase inhibitor is 3TC (lamivudine).

40. The pharmaceutical composition according to claim 34 wherein said reverse transcriptase inhibitor is d4T (stavudine).

41. The pharmaceutical composition according to claim 34 wherein said reverse transcriptase inhibitor is nevirapine.

42. The pharmaceutical composition according to claim 34 wherein said reverse transcriptase inhibitor is delavirdine.

43. The pharmaceutical composition according to claim 37 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane, or a pharmaceutically acceptable salt, ester, or prodrug thereof.

44. The pharmaceutical composition according to claim 37 wherein said compound of formula I is (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane.

45. The pharmaceutical composition according to claim 32 wherein said other HIV protease inhibitor is selected from the group consisting of ritonavir, saquinavir, VX-478, U-140690, indinavir, nelfinavir and combinations of two or more thereof, or a pharmaceutically acceptable salt thereof.

46. The pharmaceutical composition according to claim 45 wherein said additional HIV protease inhibitor is ritonavir.

47. The pharmaceutical composition according to claim 32 wherein said compound of formula I is present in the amount of from about 1% to about 50% by weight of the total composition.

48. The pharmaceutical composition according to claim 32 wherein said compound of formula I is present in the amount of from about 5% to about 30% by weight of the total composition.

49. The pharmaceutical composition according to claim 46 wherein said compound of formula I is present in the amount of from about 1% to about 50% by weight of the total composition.

50. The pharmaceutical composition according to claim 46 wherein said compound of formula I is present in the amount of from about 5% to about 30% by weight of the total composition.

51. The pharmaceutical composition according to claim 46 wherein said compound of formula I is (2S,3S,5S)-2-(2, 6-dimethylphenoxyacetyl)amino-3-hydroxy-5-(2S-(1-tetrahydro-pyrimid-2-onyl)-3-methyl butanoyl) amino-1,6-diphenylhexane, or a pharmaceutically acceptable salt, ester or prodrug thereof.

52. The pharmaceutical composition according to claim 46 wherein said compound of formula I is (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane.

53. The pharmaceutical composition according to claim 33 wherein said reverse transcriptase inhibitor is 5-halo-31-thia-dideoxycytidine.

54. The pharmaceutical composition according to claim 33 wherein said reverse transcriptase inhibitor is 3TC (lamivudine).

55. The pharmaceutical composition according to claim 33 wherein said reverse transcriptase inhibitor is d4T (stavudine).

56. The pharmaceutical composition according to claim 33 wherein said reverse transcriptase inhibitor is nevirapine.

57. The pharmaceutical formulation according to claim 33 wherein said reverse transcriptase inhibitor is delavirdine.

58. The pharmaceutical composition according to claim 33 wherein said compound of formula I is present in the amount of from about 1% to about 50% by weight of the total composition.

59. The pharmaceutical composition according to claim 33 wherein said compound of formula I is present in the amount of from about 5% to about 30% by weight of the total composition.

60. The pharmaceutical composition according to claim 33 wherein said compound of formula I is (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane, or a pharmaceutically acceptable salt, ester or prodrug thereof.

61. The pharmaceutical composition according to claim 33 wherein said compound of formula I is (2S,3S,5S)-2-(2,6-dimethylphenoxyacetyl)amino-3-hydroxy-5-(2S-(1-tetrahydro-pyrimid-2-onyl)-3-methyl butanoyl)amino-1,6-diphenylhexane.

62. The pharmaceutical composition according to claim 60 wherein said additional HIV protease inhibitor is ritonavir.

63. The pharmaceutical composition according to claim 60 wherein said reverse transcriptase inhibitor is 5-halo-3$^1$-thia-dideoxycytidine.

64. The pharmaceutical composition according to claim 60 wherein said reverse transcriptase inhibitor is 3TC (lamivudine).

65. The pharmaceutical composition according to claim 60 wherein said reverse transcriptase inhibitor is d4T (stavudine).

66. The pharmaceutical composition according to claim 60 wherein said reverse transcriptase inhibitor is nevirapine.

67. The pharmaceutical formulation according to claim 60 wherein said reverse transcriptase inhibitor is delavirdine.

68. The pharmaceutical composition according to claim 60 wherein said compound of formula I is present in the amount of from about 1d to about 50% by weight of the total composition.

69. The pharmaceutical composition according to claim 60 wherein said compound of formula I is present in the amount of from about 5% to about 30% by weight of the total composition.

70. The pharmaceutical composition according to claim 43 wherein said compound of formula I is present in the amount of from about 1% to about 50% by weight of the total composition, and ritonavir is present in the amount of from about 1% to about 30% by weight of the total composition.

71. The pharmaceutical composition according to claim 43 wherein said compound of formula I is present in the amount of from about 5% to about 30% by weight of the total composition, and ritonavir is present in the amount of from about 1% to about 30% by weight of the total composition.

72. The pharmaceutical composition according to claim 51 wherein said compound of formula I is present in the amount of from about 1% to about 50% by weight of the total composition, and ritonavir is present in the amount of from about 1% to about 30% by weight of the total composition.

73. The pharmaceutical composition according to claim 51 wherein said compound of formula I is present in the amount of from about 5% to about 30% by weight of the total composition, and ritonavir is present in the amount of from about 1% to about 30% by weight of the total composition.

74. The pharmaceutical composition according to claim 62 wherein said compound of formula I is present in the amount of from about 1% to about 50% by weight of the total composition, and ritonavir is present in the amount of from about 1% to about 30% by weight of the total composition.

75. The pharmaceutical composition according to claim 62 wherein said compound of formula I is present in the amount of from about 5% to about 30% by weight of the total composition, and ritonavir is present in the amount of from about 1% to about 30% by weight of the total composition.

76. A method for inhibiting an HIV infection comprising administering to a human in need of such treatment a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl) amino-1,6-diphenylhexane, and a reverse transcriptase inhibitor or a combination of reverse transcriptase inhibitors.

77. A method for inhibiting an HIV infection comprising administering to a human in need of such treatment a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl) amino-1,6-diphenylhexane and another HIV protease inhibitor or a combination of other HIV protease inhibitors.

78. A method for inhibiting an HIV infection comprising administering to a human in need of such treatment a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl) amino-1,6-diphenylhexane and ritonavir or a pharmaceutically acceptable salt thereof.

79. A pharmaceutical composition comprising (2S,3S,5S)-2-(2,6-dimethylphenoxyacetyl) amino-3-hydroxy-5-(2S-(1-tetrahydro-pyrimid-2-onyl)-3-methylbutanoyl) amino-1,6-diphenylhexane and ritonavir in a ratio (w/w) of from about 16:1 to about 1:5.

80. A pharmaceutical composition comprising (2S,3S,5S)-2-(2,6-dimethylphenoxyacetyl) amino-3-hydroxy-5-(2S-(1-tetrahydro-pyrimid-2-onyl)-3-methyl butanoyl) amino-1,6-diphenylhexane and ritonavir in a ratio (w/w) of from about 6:1 to about 1:3.

81. The pharmaceutical composition according to claim 61 wherein said other HIV protease inhibitor is ritonavir.

82. The pharmaceutical composition according to claim 61 wherein said reverse transcriptase inhibitor is 5-halo-3'-thia-dideoxycytidine.

83. The pharmaceutical composition according to claim 61 wherein said reverse transcriptase inhibitor is 3TC (lamivudine).

84. The pharmaceutical composition according to claim 61 wherein said reverse transcriptase inhibitor is d4T (stavudine).

85. The pharmaceutical composition according to claim 61 wherein said reverse transcriptase inhibitor is nevirapine.

86. The pharmaceutical composition according to claim 61 wherein said reverse transcriptase inhibitor is delavirdine.

87. The pharmaceutical composition according to claim 61 wherein said compound of formula I is present in the amount of from about 1% to about 50% by weight of the total composition.

88. The pharmaceutical composition according to claim 61 wherein said compound of formula I is present in the amount of from about 5% to about 30% by weight of the total composition.

89. The pharmaceutical composition according to claim 44 wherein said compound of formula I is present in the amount of from about 1% to about 50% by weight of the total composition, and ritonavir is present in the amount of from about 1% to about 30% by weight of the total composition.

90. The pharmaceutical composition according to claim 44 wherein said compound of formula I is present in the amount of from about 5% to about 30% by weight of the total composition, and ritonavir is present in the amount of from about 1% to about 30% by weight of the total composition.

91. The pharmaceutical composition according to claim 52 wherein said compound of formula I is present in the amount of from about 1% to about 50% by weight of the total composition, and ritonavir is present in the amount of from about 1% to about 30% by weight of the total composition.

92. The pharmaceutical composition according to claim 52 wherein said compound of formula I is present in the amount of from about 5% to about 30% by weight of the total composition, and ritonavir is present in the amount of from about 1% to about 30% by weight of the total composition.

93. The pharmaceutical composition according to claim 61 wherein said compound of formula I is present in the amount of from about 1% to about 50% by weight of the total composition, and ritonavir is present in the amount of from about 1% to about 30% by weight of the total composition.

94. The pharmaceutical composition according to claim 61 wherein said compound of formula I is present in the amount of from about 5% to about 30% by weight of the total composition, and ritonavir is present in the amount of from about 1% to about 30% by weight of the total composition.

95. The method of claim 76 wherein the reverse transcriptase inhibitor is selected from the group consisting of 5-halo-3'-thia-dideoxycytidine, AZT (zidovudine), ddI (didanosine), ddC (zalcitabine), d4T (stavudine), 3TC (lamivudine), nevirapine, delavirdine, trovirdine, PMEA, bis-POMPMEA, MSA-300 and combinations of two or more thereof.

96. The method of claim 77 wherein the other HIV protease inhibitor is selected from the group consisting of ritonavir, saquinavir, indinavir, nelfinavir, VX-478, DMP-323, DMP-450, BMS 186,318, SC-55389a, BILA 1096 BS, U-140690, 5-(S)-Boc-amino-4(S)-hydroxy-6-phenyl-2(R)-phenylmethylhexanoyl-(L)-Val-(L)-Phe-morpholin-4-ylamide, 1-Naphthoxyacetyl-beta-methylthio-Ala-(2S,3S)-3-amino-2-hydroxy-4-butanoyl-1,3-thiazolidine-4-t-butylamide, 5-isoquinolinoxyacetyl-beta-methylthio-Ala-(2S,3S)-3-amino-2-hydroxy-4-butanoyl-1,3-thiazolidine-4-t-butylamide, (1S-(1R*(R*),2S*))—N$^1$(3-((((1,1-dimethylethyl)amino)carbonyl)(2-methylpropyl)amino)-2-hydroxy-1-(phenylmethyl)propyl)-2-((2-quinolinylcarbonyl)amino)-butanediamide and combinations of two or more thereof; or a pharmaceutically acceptable salt thereof.

97. A method for inhibiting an HIV infection comprising administering to a human in need of such treatment a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane and ritonavir.

98. A pharmaceutical composition comprising a pharmaceutical carrier and a therapeutically effective combination of the compound (2S,3S,5S)-2-(2,6-dimethylphenoxyacetyl)amino-3-hydroxy-5-(2S-(1-tetrahydro-pyrimid-2-onyl)-3-methylbutanoyl)amino-1,6-diphenylhexane and ritonavir.

* * * * *

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 1,
Line 43, replace "high blood pressure in v." with -- high blood pressure in vivo. --
Line 48, replace "such as the and a gene products" with -- such as the pol and gag gene products. --
Line 51, replace "process the poi" with -- process the pol --

Column 19,
Line 24, replace "refers to $R_1C(O)$-" with -- refers to $R_{19}C(O)$- --
Line 33, replace "$R^{15}O$-" with -- $R_{15}O$- --
Line 63, replace "benzoxazolyi" with -- benzoxazolyl --

Column 21,
Line 38, replace "and the like to give." with -- and the like to give 3. --
Line 55, replace "compound x" with -- compound 3 --
Line 58, replace "10 liters/kilogram of compound 1 ." with -- 10 liters/kilogram of compound 3. --

Column 22,
Line 57-58, replace "to provide compound." with -- to provide compound 6. --
Line 60, replace "intermediate compound a has the formula" with -- intermediate compound 5 has the formula --

Column 24,
Line 7, replace "Hydrogenation of 1" with -- Hydrogenation of 19 --
Line 16, replace "KOH or NaCH" with -- KOH or "NaOH --

Column 30,
Line 11, replace "Z is N" with -- Z is O --

Column 34,
Line 5, replace "CDC13)37.2" with -- CDC13) $\delta$7.2 --

Column 35,
Line 41, replace "Example of G" with -- Example 1G --
Line 51, replace "-6-" with -- 1.6- --
Line 57, replace "3.75(m, 2H)" with -- 3.75(m, 1H) --

Column 36,
Line 24, replace "dried with any" with -- dried with anhy. --

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 37,
Line 6, replace "(1-imidazolidin-2-onyl-" with -- (1-imidazolidin-2onyl-) --

Column 38,
Line 19, replace "C.(2S,3S, 5S-2" with -- C.(2S,3S, 5S)-2 --

Column 39,
Line 37, replace "31.27" with -- δ 1.27 --

Column 40,
Line 40, replace "C.5-(Hydroxymethylthiazole" with -- C.5(Hydroxymethyl)thiazole --

Column 41,
Line 4, replace "5 5.53" with -- δ 5.53 --
Line 4, replace "31.3" with -- δ 1.3 --
Line replace "(m, 1 OH)" with -- (m, 10H) --

Column 43,
Line 4, replace "recduced" with -- reduced --
Line 28, replace "Example 1°" with -- Example 10C --
Line 33, replace "(m, 1 OH)" with -- (m, 10H) --
Line 40, replace "Example 1D" with -- Example l0D --

Column 44,
Line 56, replace "(m, 1 OH)." with -- (m, 10H). --

Column 45,
Line 61, replace "dimethylbutanoyl" with -- dimethyl butanoyl --
Line 67, replace "61.0" with -- δ 1.0 --

Column 46,
Line 33, replace "62.56" with -- δ 2.56 --
Line 57, replace "1.55 9" with -- 1.55g --

Column 48,
Line 5, replace "(m, 1 OH)." with -- (m, 10H). --
Line 20, replace "progenoic" with -- propenoic --

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 49,
Line 36, replace "(m, 1 OH)" with -- (m, 10H) --
Line 44, replace "2°" with -- 20C. --
Line 61, replace "butyldimethylsilyloxyphenyl" with -- butyldimethylsilyloxy phenyl --

Column 50,
Line 28, replace "2.03 9" with -- 2.03g --

Column 51,
Line 7, replace "(m, 1 OH)." with -- (m, 10H). --
Line 11, replace "(+)" with -- (±) --
Line 13, replace "-3-methylbutanoylamino-" with -- -3-methyl butanoyl)amino- --
Line 20, replace "16.75 9" with -- 16.75g --

Column 52,
Line 13, replace "(+)" with -- (±) --
Line 35, replace "(539)" with -- (839) --
Line 46, replace "(+)" with -- (±) --

Column 53,
Line 67, replace "78.8 9" with -- 78.8g --

Column 54,
Line 14, replace "106 9" with -- 106g --

Column 56,
Line 20, replace "1 26g" with -- 126g --
Line 40, replace "methylbutanoyl" with -- methyl butanoyl --
Line 40, replace "16" with -- l, 6 --
Line 43, replace "241" with -- 24I --
Line 52, replace "HC1"with -- HCI --

Column 57,
Line 31, replace "m, lHI" with -- m, lH --
Line 57, replace "0.36 9" with -- 0.36g --
Line 58, replace "50.86" with -- δ0.86 --

Column 59,
Line 28, replace "butanoic" with -- butanoic acid --
Line 46, replace "1 8H)." with -- 18H). --

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 60,
Line 16, replace "J=BHz," with -- J=8Hz, --

Column 61,
Line 45, replace "J=1 0Hz," with -- J=10Hz, --

Column 62,
Line 46, replace "11" with -- 1I --

Column 63,
Line 7, replace "11" with -- 1I --
Line 42, replace "+5°"with -- ±5° --
Line 67, replace "C. +1°C" with -- C ±10°C --

Column 64,
Line 13, replace "1°" with -- 10° --
Line 14, replace "1°" with -- 10° --
Line 39, replace "1°" with -- 10° --
Line 57, replace "occurrs" with -- occurs --
Line 66, replace "1 2°" with -- 12° --

Column 65,
Line 17, replace "1° C" with -- 10° C --

Column 66,
Line 34, replace "methylbutanoyl" with -- methyl butanoyl --
Line 52, replace "57.35" with -- δ7.35 --

Column 67,
Line 20, replace "methylbutanoyl" with -- methyl butanoyl --
Line 35, replace "≧"with -- ≥ --
Line 38, replace "m, 1 OH" with -- m, 10H --
Line 43, replace "CD$_3$0D" with -- CD$_3$OD --
Line 43, replace "3171.3" with -- δ171.3 --
Line 46, replace "m, 1 OH" with -- m, 10H --
Line 50, replace "8171.2" with -- δ171.2 --
Line 55, replace "methyl]butanoyl]" with -- methyl butanoyl] --

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 68,
Line 6, replace "$CH_{30H}$" with -- $CH_3OH$ --
Line 7, replace "mlz" with -- *m/z* --
Line 18, replace "6176.9" with -- $\delta$176.9 --
Line 19, replace "128.3,127.8" with -- 128.3, 127.8 --
Line 21, replace "19.6,18.7" with -- 19.6, 18.7 --
Line 22, replace "m, 1 OH" with -- m, 10H --
Line 33, replace "67.30" with -- 7.30 --
Line 37, replace "$D_20$ " with -- $D_2O$ --
Line 38, replace "3181. 6180.1," with $\delta$181.6, 180.1, --
Line 44, replace "methylbutanoyl" with -- methyl butanoyl --

Column 69,
Line 36, replace "10-1 5°" with -- 10-15° --
Line 48, replace "chlorogropylaminocarbonyl" with -- chloropropylaminocarbonyl --

Column 70,
Line 5, replace "methylbutanoyl" with -- methyl butanoyl --
Line 10, replace "$^1$4Cl" with -- $^{14}C$ --
Line 11, replace "50 , M" with -- 50$\mu$M, --
Line 19, replace "5, tm" with -- 5$\mu$m --
Line 20, replace "Alitech" with -- Alltech --
Line 36, replace "13IM" with -- 1.3$\mu$M --

Column 71,
Line 42, replace "5701650" with -- 570/650 --

Column 72,
Line 63, replace "Ra-C(Rb)" with -- $R_a$-C($R_b$) --
Line 63, replace "Rd" with -- $R_d$ --
Line 64, replace "Ra" with -- $R_a$ --
Line 66, replace "(Re)(Rf)" with -- ($R_e$)($R_f$) --

UNITED STATES PATENT AND TRADEMARK OFFICE
CERTIFICATE OF CORRECTION

PATENT NO. : 6,284,767 B1
DATED : September 4, 2001
INVENTOR(S) : Hing Leung Sham et al.

It is certified that error appears in the above-identified patent and that said Letters Patent is hereby corrected as shown below:

Column 73,
Line 26, replace "in vivo" with -- in vivo --
Line 38-39, replace "in vitro or in vivo" with -- in vitro or in vivo --

Column 74,
Line 52, replace "aceptable" with -- acceptable --

Column 75,
Line 50, replace "1 00g" with -- 100g --

Column 76,
Line 7, replace "B1" with -- BI --
Line 24, replace "R821 50, U-87201 E" with -- R82150, U-87201E --

Column 78,
Line 21, replace "$^2$-methypropy" with -- 2-methypropyl --
Line 21, replace "$^2$-quinolinylcarbonyl" with -- 2-quinolinylcarbonyl --

Column 79,
Line 10, REMOVE the comma from the diagram

Column 80,
Line 57, replace "a bo.'t" with -- about --

Column 82,
Line 7, replace "43%" with -- 40% --
Line 38, replace "10" with -- 50 --
Line 48, replace "549.9 9" with -- 549.9g --

Column 87,
Line 67, replace "methipropyl" with -- methylpropyl --
Line 67, replace "methipropyl" with -- methylpropyl --

UNITED STATES PATENT AND TRADEMARK OFFICE
CERTIFICATE OF CORRECTION

PATENT NO.    : 6,284,767 B1
DATED         : September 4, 2001
INVENTOR(S)   : Hing Leung Sham et al.

It is certified that error appears in the above-identified patent and that said Letters Patent is hereby corrected as shown below:

Column 92,
Line 63, replace "U-140690, nelfinavir" with -- U-140690, indinavir nelfinavir --

Column 94,
Line 53, add -- $R_5$ is: --

Column 98,
Line 13, replace "methylbutanoyl" with -- methyl butanoyl --
Line 40, replace "methylbutanoyl" with -- methyl butanoyl --

Column 99,
Line 8, replace "methylbutanoyl" with -- methyl butanoyl --
Line 43, replace "additional" with -- other --
Line 60, replace "1d" with -- 1% --

Column 100,
Line 39, replace "methylbutanoyl" with -- methyl butanoyl --
Line 46, replace "methylbutanoyl" with -- methyl butanoyl --
Line 53, replace "methylbutanoyl" with -- methyl butanoyl --
Line 58, replace "methylbutanoyl" with -- methyl butanoyl --

Signed and Sealed this

Twenty-seventh Day of May, 2003

JAMES E. ROGAN
*Director of the United States Patent and Trademark Office*